US007468254B2

(12) United States Patent
Young et al.

(10) Patent No.: US 7,468,254 B2
(45) Date of Patent: Dec. 23, 2008

(54) CYTOTOXICITY MEDIATION OF CELLS EVIDENCING SURFACE EXPRESSION OF MCSP

(75) Inventors: David S. F. Young, Toronto (CA); Susan E. Hahn, Toronto (CA); Helen P. Findlay, Toronto (CA); Alison L. Ferry, Toronto (CA)

(73) Assignee: Arius Research Inc., Toronto, Ontario (CA)

( * ) Notice: Subject to any disclaimer, the term of this patent is extended or adjusted under 35 U.S.C. 154(b) by 275 days.

(21) Appl. No.: 10/949,846

(22) Filed: Sep. 24, 2004

(65) Prior Publication Data

US 2005/0063967 A1  Mar. 24, 2005

Related U.S. Application Data

(63) Continuation-in-part of application No. 10/810,744, filed on Mar. 26, 2004, now Pat. No. 7,393,531, which is a continuation-in-part of application No. 10/762,129, filed on Jan. 20, 2004, now Pat. No. 7,361,342, which is a continuation-in-part of application No. 10/743,451, filed on Dec. 19, 2003, now abandoned, which is a continuation of application No. 10/348,231, filed on Jan. 21, 2003, now Pat. No. 7,009,040.

(51) Int. Cl.
G01N 33/53 (2006.01)
G01N 33/574 (2006.01)
C07K 16/00 (2006.01)

(52) U.S. Cl. ............... 435/7.1; 435/7.23; 530/387.1; 530/388.1; 530/388.8

(58) Field of Classification Search .................. None
See application file for complete search history.

(56) References Cited

U.S. PATENT DOCUMENTS

| 4,861,581 | A | 8/1989 | Epstein et al. |
| 4,879,225 | A | 11/1989 | Morgan et al. |
| 5,017,693 | A | 5/1991 | Hylarides et al. |
| 5,034,223 | A | 7/1991 | Abrams et al. |
| 5,112,954 | A | 5/1992 | Abrams et al. |
| 5,171,665 | A | 12/1992 | Hellstrom et al. |
| 5,270,202 | A | 12/1993 | Raychaudhuri |
| 5,484,596 | A | 1/1996 | Hanna, Jr. et al. |
| 5,493,009 | A | 2/1996 | Ferrone |
| 5,580,774 | A | 12/1996 | Beavers et al. |
| 5,693,763 | A | 12/1997 | Codington et al. |
| 5,707,603 | A | 1/1998 | Toner et al. |
| 5,750,102 | A | 5/1998 | Eisenbach et al. |
| 5,780,029 | A | 7/1998 | Ferrone |
| 5,780,033 | A | 7/1998 | Torchilin et al. |
| 5,783,186 | A | 7/1998 | Arakawa et al. |
| 5,817,774 | A | 10/1998 | Delecki et al. |
| 5,849,876 | A | 12/1998 | Linsley et al. |
| 5,869,045 | A | 2/1999 | Hellstrom et al. |
| 5,869,268 | A | 2/1999 | Kudo et al. |
| 6,180,357 | B1 | 1/2001 | Young et al. |
| 6,238,667 | B1 | 5/2001 | Kohler |
| 6,248,870 | B1 | 6/2001 | Delecki et al. |
| 2004/0141913 | A1 | 7/2004 | Young et al. |
| 2004/0141979 | A1 | 7/2004 | Young et al. |
| 2004/0151665 | A1 | 8/2004 | Young et al. |
| 2004/0197328 | A1 | 10/2004 | Young et al. |
| 2006/0019256 | A1* | 1/2006 | Clarke et al. .................. 435/6 |

FOREIGN PATENT DOCUMENTS

| EP | 380607 | 12/1994 |
| WO | WO92/16646 | 10/1992 |
| WO | WO03/086456 | 10/2003 |

OTHER PUBLICATIONS

Li et al. (Proc. Natl. Acad. Sci. USA, 1980 77:3211-3214).*
Rudikoff et al, (PNAS, USA, 1982, 79: 1979).*
Jiang et al (JBC, 2003, 278(7) 4763-4769).*
Matsushita et al (FEBS Letters, 1999, vol. 443, pp. 348-352).*
Singh et al (Glycobiology, 2001, vol. 11, pp. 587-592).*
Freshney (Culture of Animal Cells, A Manual of Basic Technique, Alan R. Liss, Inc., 1983, New York, p. 4).*
Dermer (Bio/Technology, 1994, 12:320).*
Drexler et al (Leukemia and Lymphoma, 1993, 9:1-25).*
Zellner et al (Clin. Can. Res., 1998, 4:1797-17802).*
Embleton et al (Immunol Ser, 1984, 23:181-207).*
Taber's Cyclopedic Medical Dictionary (1985, F.A. Davis Company, Philadelphia, p. 274).*
Busken, C et al, (Digestive Disease Week Abstracts and Itinerary Planner, 2003, abstract No. 850.*
Kaiser (Science, 2006, 313, 1370).*
T. Karpanen et al, "Vascular endothelial growth factor C promotes tumor lymphangiogenesis and intralymphatic tumor growth", Cancer Research, 61:1786-1790 (Mar. 2001).
W. Waud et al, "Characterization of in vivo mammary and prostate tumor xenograft models for growth and response to clinical anticancer agents", Contrib Oncol Basel Karger, 54:305-315 (1999).
G. Klement et al, "Differences in therapeutic indexes of combination metronomic chemotherapy and an anti-VEGFR-2 antibody in multidrug-resistant human breast cancer xenografts", Clinical Cancer Research, 8:221-232 (Jan. 2002).
D. Blakey et al, "Antitumor activity of the novel vascular targeting agent ZD6126 in a panel of tumor models", Clinical Cancer Research, 8:1974-1983 (Jun. 2002).
Z. Xiao et al, "Generation of a baculovirus recombinant prostate-specific membrane antigen and its use in the development of a novel protein biochip quantitative immunoassay", Protein Expresion and Purification, 19:12-21 (2000).

(Continued)

*Primary Examiner*—Karen A. Canella
*Assistant Examiner*—Peter J Reddig
(74) *Attorney, Agent, or Firm*—McHale & Slavin, P.A.

(57) ABSTRACT

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays which utilize the CDMABs of the instant invention.

4 Claims, 16 Drawing Sheets
(6 of 16 Drawing Sheet(s) Filed in Color)

OTHER PUBLICATIONS

S. Guichard et al, "Schedule-dependent activity of topotecan in OVCAR-3 ovarian carcinoma xenograft: pharmacokinetic and pharmacodynamic evaluation", Clinical Cancer Research, 7:3222-3228 (Oct. 2001).

V. Von Gruenigen et al, "Efficacy of intraperitoneal adenovirus-mediated p53 gene therapy in ovarian cancer", Int. J. Gynecol. Cancer, 9:365-372 (1999).

N. Guilbaud et al, "Marked antitumor activity of a new potent acronycine derivative in orthotopic models of human solid tumors", Clinical Cancer Research, 7:2573-2580 (Aug. 2001).

K. Olson et al, "Inhibition of prostate carcinoma establishment and metastatic growth in mice by an antiangiogenin monoclonal antibody", Int. J. Cancer, 98:923-929 (2002).

S. Hirschfeld et al, "Oncology drug development: United States Food and Drug Administration perspective", Critical Reviews in Oncology/Hematology, 42:137-143 (2002).

P. Therasse et al, "New guidelines to evaluate the response to treatment in solid tumors", Journal of the National Cancer Institute, 92(3):205-216 (Feb. 2000).

G. Eckhardt et al, "Developmental therapeutics: successes and failures of clinical trial designs of targeted compounds", in American Society of Clinical Oncology, pp. 209-219 (2003).

P. Smith et al, "Anti-interleukin-6 monoclonal antibody induces regression of human prostate cancer xenografts in nude mice", The Prostate, 48:47-53 (2001).

T. Bumol et al, "Unique glycoprotein-proteoglycan complex defined by monoclonal antibody on human melanoma cells", Proc. Natl. Acad. Sci. USA, 79(4):1245-1249 (Feb. 1982).

P. Chattopadhyay et al, "Murine monoclonal anti-idiotope antibody breaks unresponsiveness and induces a specific antibody response to human melanoma-associated proteoglycan antigen in cynomolgus monkeys", Proc. Natl. Acad. Sci. USA, 89:2684-2688 (Apr. 1992).

T. Bumol et al, "Monoclonal antibody and an antibody-toxin conjugate to a cell surface proteoglycan of melanoma cells suppress in vivo tumor growth", Proc. Natl. Acad. Sci. USA, 80(2):529-533 (Jan. 1983).

G. Pluschke et al, "Molecular cloning of a human melanoma-associated chondroitin sulfate proteoglycan", Proc. Natl. Acad. Sci. USA, 93:9710-9715 (Sep. 1996).

J. Iida et al, "Melanoma chondroitin sulfate proteoglycan regulates matrix metalloproteinase-dependent human melanoma invasion into type I collagen", J. Biol. Chem., 276(22):18786-18794 (Jun. 2001).

K. Eisenmann et al, "Melanoma chondroitin sulphate proteoglycan regulates cell spreading through Cdc42, Ack-1 and p130cas", Nature Cell Biology, 1:507-513 (Dec. 1999).

S. Ferrone et al, "Human high molecular weight-melanoma asociated antigen mimicry by mouse antri-idiotypic monoclonal antibodies MK2-23 experimental studies and clinical trials in patients with malignant melanoma", Pharmac. Ther., 57:259-290 (1993).

A. Mittelman et al, "Human high molecular weight melanoma-associated antigen (HMW-MAA) mimicry by mouse anti-idiotypic monoclonal antibody MK2-23: induction of humoral anti-HMW-MAA immunity and prolongation of survival in patients with stage IV melanoma", Proc. Natl. Acad. Sci. USA, 89:466-470 (Jan. 1992).

H. Ming Yang et al, "Doxorubicin conjugated with a monoclonal antibody directed to a human melanoma-associated proteoglycan suppresses the growth of established tumor xenografts in nude mice", Proc. Natl. Acad. Sci. USA, 85:1189-1193 (Feb. 1988).

M. Kusama et al, "Characterization of syngeneic antiidiotypic monoclonal antibodies to murine anti-human high molecular weight melanoma-associated antigen monoclonal antibodies", J. Immunol., 143(11):3844-3852 (Dec. 1989).

T. Bumol et al, "Biosynthetic studies of proteoglycans in human melanoma cells with a monoclonal antibody to a core glycoprotein of chondroitin sulfate proteoglycans", J. Biol. Chem., 259(20):12733-12741 (Oct. 1984).

D. Demetrick et al, "ME491 melanoma-associated glycoprotein family: antigenic identity of ME491, NKI/C-3, neuroglandular antigen (NGA), and CD63 proteins", J. Natl Cancer Inst, 84(6):422-429 (Mar. 1992).

C. Vennegoor et al, "Circulating melanoma-associated antigen detected by monoclonal antibody NKI/C-3", Cancer Immunol Immunother, 23:93-100 (1986).

M. Wang et al, "An ocular melanoma-associated antigen", Arch Ophthalmol., 110:399-404 (Mar. 1992).

B. Ulbricht et al, "Influence of 12(S)-hydroxyeicosatetraenoic acid (12(S)-HETE) on the localization of cathepsin B and cathepsin L in human lung tumor cells", European Journal of Cell Biology, 74:294-301 (Nov. 1997).

J. Harper et al, "Inhibition of anchorage-independent growth of human melanoma cells by a monoclonal antibody to a chondroitin sulfate proteoglycan", JNCI, 71(2):259-263 (Aug. 1983).

R. Oldham et al, "Monoclonal antibody therapy of malignant melanoma: in vivo localization in cutaneous metastasis after intravenous administration", J. Clin Oncol, 2(11):1235-1244 (Nov. 1984).

K. Imai et al, "Higher cytolytic efficiency of an IgG2a than of an IgG1 monoclonal antibody reacting with the same (or spatially close) determinant on a human high-molecular-weight melanoma-associated antigen", Cellular Immunology, 72:239-247 (1982).

M. Matsui et al, "Suppression of human melanoma growth in nude mice injected with anti high-molecular-weight melanoma-associated antigen monoclonal antibody 225.28S conjugated to purothionin", Jpn. J. Cancer Res., 76:119-123 (Feb. 1985).

B. Wilson et al, "Distribution and molecular characterization of a cell-surface and a cytoplasmic antigen detectable in human melanoma cells with monoclonal antibodies", Int. J. Cancer, 28:293-300 (1981).

M. Schrappe et al, "Long-term growth suppression of human glioma xenografts by chemoimmunoconjugates of 4-desacetylvinblastine-3-carboxyhydrazide and monoclonal antibody 9.2.27", Cancer Research, 52:3838-3844 (Jul. 1992).

T. Ghose et al, "Regression of human melanoma xenografts in nude mice injected with methotrexate linked to monclonal antibody 225.28 to human high molecular weight-melanoma associated antigen", Cancer Immunol Immunother, 34:90-96 (1991).

N. Cascinelli et al, "Anti-melanoma monoclonal antibody 225-28S: evaluation of toxicity in man", Tumori, 74:35-40 (1988).

E. Neuwelt et al, "Increased delivery of tumor-specific monoclonal antibodies to brain after osmotic blod-brain barrier modification in patients with melanoma metastatic to the central nervous system", Neurosurgery, 20 (6):885-895 (Jun. 1987).

G. Goodman et al, "Pilot trial of murine monoclonal antibodies in patients with advanced melanoma", J. Clin Oncol, 3(3):340-352 (Mar. 1985).

R. Reisfeld, "Immunochemical characterization of human tumor antigens", Seminars in Oncology, 13(2):153-164 (Jun. 1986).

P. Garin-Chesa et al, "Cell surface molecules of human melanoma immunohistochemical analysis of the gp57, GD3, and mel-CSPG antigenic systems", American Journal of Pathology, 134(2):295-303 (Feb. 1989).

H. Jacques Garrigues et al, "The melanoma proteoglycan: restricted expression on microspikes, a specific microdomain of the cell surface", J. Cell Biol., 103:1699-1710 (Nov. 1986).

F. Real et al, "Surface antigens of melanomas and melanocytes defined by mouse monoclonal antibodies: specificity analysis and comparison of antigen expression in cultured cells and tissues", Cancer Research, 45:4401-4411 (Sep. 1985).

W. Rettig et al, "Human melanoma proteoglycan: expression in hybrids controlled by intrinsic and extrinsic signals", Science, 231:1281-1284 (Mar. 1986).

Z. Jian Chen et al, "Modulation by adjuvants and carriers of the immunogenicity in xenogeneic hosts of mouse anti-idiotypic monoclonal antibody MK2-23, an internal image of human high molecular weight-melanoma associated antigen", Cancer Research, 53:112-119 (Jan. 1993).

R. Reisfeld et al, "Human tumor-associated antigens defined by monoclonal antibodies", CRC Critical Reviews in Immunology, 5(1):27-53.

I. Hellstrom et al, "Studies of a high molecular weight human melanoma-associated antigen", J. Immunol., 130(3):1467-1472 (Mar. 1983).

A. Mittelman et al, "Active specific immunotherapy in patients with melanoma", J. Clin. Invest., 86:2136-2144 (Dec. 1990).

P. Chattopadhyay et al, "Human high molecular weight-melanoma associated antigen mimicry by an anti-idiotypic antibody: characterization of the immunogenicity and the immune response to the mouse monoclonal antibody IMel-1", Cancer Research, 51:6045-6051 (Nov. 1991).

K. Imai et al, "Selective in vitro toxicity of purothionin conjugated to the monoclonal antibody 225.28S to a human high-molecular-weight melanoma-associated antigen", Cancer Immunol Immunother, 15:206-209 (1983).

K. Imai et al, "Monoclonal-antibodies to human melanoma-associated antigens", Transplantation Proceedings, 12(3):380-383 (Sep. 1980).

A. Mittelman et al, "Human high molecular weight-melanoma associated antigen mimicry by mouse anti-idiotypic monoclonal antibody MK2-23: modulation of the immunogenicity in patients with malignant melanoma", Clinical Cancer Research, 1:705-713 (Jul. 1995).

M. Saleh et al, "Immunologic response to the dual murine anti-Id vaccine melimmune-1 and melimmune-2 in patients with high-risk melanoma without evidence of systemic disease", J. Immunother., 21(5):379-388 (1998).

P. Chattopadhyay et al, "Monoclonal anti-idiotypic antibodies to human melanoma-associated proteoglycan antigen: generation and characterization of anti-idiotype antibodies", Cancer Research, 51:3183-3192 (Jun. 1991).

W. Quan et al, "Active specific immunotherapy of metastatic melanoma with an antiidiotype vaccine: a phase I/II trial of I-MeI-2 plus SAF-m", J. Clin Oncol., 15(5):2103-2110 (May 1997).

M. Geiser et al, "Identification of the human melanoma-associated chondroitin sulfate proteoglycan antigen epitope recognized by the antitumor monoclonal antibody 763.74 from a peptide phage library", Cancer Research, 59:905-910 (Feb. 1999).

* cited by examiner

SEQUENCE LISTING

<160> NUMBER OF SEQ ID NOS: 257

<210> SEQ ID NO 1
<211> LENGTH: 18
<212> TYPE: PRT
<213> ORGANISM: Homo sapiens

<400> SEQUENCE: 1

Met Gln Ser Gly Arg Gly Pro Pro Leu Pro Ala Pro Gly Leu Ala Leu
1               5                   10                  15

Ala Leu

<210> SEQ ID NO 2
<211> LENGTH: 18
<212> TYPE: PRT
<213> ORGANISM: Homo sapiens

<400> SEQUENCE: 2

Pro Ala Pro Gly Leu Ala Leu Ala Leu Thr Leu Thr Met Leu Ala Arg
1               5                   10                  15

Leu Ala

<210> SEQ ID NO 3
<211> LENGTH: 18
<212> TYPE: PRT
<213> ORGANISM: Homo sapiens

```
<400> SEQUENCE: 3

Thr Leu Thr Met Leu Ala Arg Leu Ala Ser Ala Ala Ser Phe Phe Gly
1               5                   10                  15

Glu Asn

<210> SEQ ID NO 4
<211> LENGTH: 18
<212> TYPE: PRT
<213> ORGANISM: Homo sapiens

<400> SEQUENCE: 4

Ser Ala Ala Ser Phe Phe Gly Glu Asn His Leu Glu Val Pro Val Ala
1               5                   10                  15

Thr Ala

<210> SEQ ID NO 5
<211> LENGTH: 18
<212> TYPE: PRT
<213> ORGANISM: Homo sapiens

<400> SEQUENCE: 5

His Leu Glu Val Pro Val Ala Thr Ala Leu Thr Asp Ile Asp Leu Gln
1               5                   10                  15

Leu Gln

<210> SEQ ID NO 6
<211> LENGTH: 18
<212> TYPE: PRT
<213> ORGANISM: Homo sapiens

<400> SEQUENCE: 6

Leu Thr Asp Ile Asp Leu Gln Leu Gln Phe Ser Thr Ser Gln Pro Glu
1               5                   10                  15

Ala Leu

<210> SEQ ID NO 7
<211> LENGTH: 18
<212> TYPE: PRT
<213> ORGANISM: Homo sapiens

<400> SEQUENCE: 7

Phe Ser Thr Ser Gln Pro Glu Ala Leu Leu Leu Leu Ala Ala Gly Pro
1               5                   10                  15

Ala Asp

<210> SEQ ID NO 8
<211> LENGTH: 18
<212> TYPE: PRT
<213> ORGANISM: Homo sapiens

<400> SEQUENCE: 8

Leu Leu Leu Ala Ala Gly Pro Ala Asp His Leu Leu Leu Gln Leu Tyr
1               5                   10                  15

Ser Gly

<210> SEQ ID NO 9
<211> LENGTH: 18
<212> TYPE: PRT
<213> ORGANISM: Homo sapiens
```

```
<400> SEQUENCE: 9

His Leu Leu Leu Gln Leu Tyr Ser Gly Arg Leu Gln Val Arg Leu Val
1               5                   10                  15

Leu Gly

<210> SEQ ID NO 10
<211> LENGTH: 18
<212> TYPE: PRT
<213> ORGANISM: Homo sapiens

<400> SEQUENCE: 10

Arg Leu Gln Val Arg Leu Val Leu Gly Gln Glu Glu Leu Arg Leu Gln
1               5                   10                  15

Thr Pro

<210> SEQ ID NO 11
<211> LENGTH: 18
<212> TYPE: PRT
<213> ORGANISM: Homo sapiens

<400> SEQUENCE: 11

Gln Glu Glu Leu Arg Leu Gln Thr Pro Ala Glu Thr Leu Leu Ser Asp
1               5                   10                  15

Ser Ile

<210> SEQ ID NO 12
<211> LENGTH: 18
<212> TYPE: PRT
<213> ORGANISM: Homo sapiens

<400> SEQUENCE: 12

Ala Glu Thr Leu Leu Ser Asp Ser Ile Pro His Thr Val Val Leu Thr
1               5                   10                  15

Val Val

<210> SEQ ID NO 13
<211> LENGTH: 18
<212> TYPE: PRT
<213> ORGANISM: Homo sapiens

<400> SEQUENCE: 13

Pro His Thr Val Val Leu Thr Val Val Glu Gly Trp Ala Thr Leu Ser
1               5                   10                  15

Val Asp

<210> SEQ ID NO 14
<211> LENGTH: 18
<212> TYPE: PRT
<213> ORGANISM: Homo sapiens

<400> SEQUENCE: 14

Glu Gly Trp Ala Thr Leu Ser Val Asp Gly Phe Leu Asn Ala Ser Ser
1               5                   10                  15

Ala Val

<210> SEQ ID NO 15
<211> LENGTH: 18
<212> TYPE: PRT
<213> ORGANISM: Homo sapiens
```

<400> SEQUENCE: 15

Gly Phe Leu Asn Ala Ser Ser Ala Val Pro Gly Ala Pro Leu Glu Val
1               5                   10                  15
Pro Tyr

<210> SEQ ID NO 16
<211> LENGTH: 18
<212> TYPE: PRT
<213> ORGANISM: Homo sapiens

<400> SEQUENCE: 16

Pro Gly Ala Pro Leu Glu Val Pro Tyr Gly Leu Phe Val Gly Gly Thr
1               5                   10                  15
Gly Thr

<210> SEQ ID NO 17
<211> LENGTH: 18
<212> TYPE: PRT
<213> ORGANISM: Homo sapiens

<400> SEQUENCE: 17

Gly Leu Phe Val Gly Gly Thr Gly Thr Leu Gly Leu Pro Tyr Leu Arg
1               5                   10                  15
Gly Thr

<210> SEQ ID NO 18
<211> LENGTH: 18
<212> TYPE: PRT
<213> ORGANISM: Homo sapiens

<400> SEQUENCE: 18

Leu Gly Leu Pro Tyr Leu Arg Gly Thr Ser Arg Pro Leu Arg Gly Cys
1               5                   10                  15
Leu His

<210> SEQ ID NO 19
<211> LENGTH: 18
<212> TYPE: PRT
<213> ORGANISM: Homo sapiens

<400> SEQUENCE: 19

Ser Arg Pro Leu Arg Gly Cys Leu His Ala Ala Thr Leu Asn Gly Arg
1               5                   10                  15
Ser Leu

<210> SEQ ID NO 20
<211> LENGTH: 18
<212> TYPE: PRT
<213> ORGANISM: Homo sapiens

<400> SEQUENCE: 20

Ala Ala Thr Leu Asn Gly Arg Ser Leu Leu Arg Pro Leu Thr Pro Asp
1               5                   10                  15
Val His

<210> SEQ ID NO 21
<211> LENGTH: 18
<212> TYPE: PRT
<213> ORGANISM: Homo sapiens

```
<400> SEQUENCE: 21

Leu Arg Pro Leu Thr Pro Asp Val His Glu Gly Cys Ala Glu Glu Phe
1               5                   10                  15

Ser Ala

<210> SEQ ID NO 22
<211> LENGTH: 18
<212> TYPE: PRT
<213> ORGANISM: Homo sapiens

<400> SEQUENCE: 22

Glu Gly Cys Ala Glu Glu Phe Ser Ala Ser Asp Asp Val Ala Leu Gly
1               5                   10                  15

Phe Ser

<210> SEQ ID NO 23
<211> LENGTH: 18
<212> TYPE: PRT
<213> ORGANISM: Homo sapiens

<400> SEQUENCE: 23

Ser Asp Asp Val Ala Leu Gly Phe Ser Gly Pro His Ser Leu Ala Ala
1               5                   10                  15

Phe Pro

<210> SEQ ID NO 24
<211> LENGTH: 18
<212> TYPE: PRT
<213> ORGANISM: Homo sapiens

<400> SEQUENCE: 24

Gly Pro His Ser Leu Ala Ala Phe Pro Ala Trp Gly Thr Gln Asp Glu
1               5                   10                  15

Gly Thr

<210> SEQ ID NO 25
<211> LENGTH: 18
<212> TYPE: PRT
<213> ORGANISM: Homo sapiens

<400> SEQUENCE: 25

Ala Trp Gly Thr Gln Asp Glu Gly Thr Leu Glu Phe Thr Leu Thr Thr
1               5                   10                  15

Gln Ser

<210> SEQ ID NO 26
<211> LENGTH: 18
<212> TYPE: PRT
<213> ORGANISM: Homo sapiens

<400> SEQUENCE: 26

Leu Glu Phe Thr Leu Thr Thr Gln Ser Arg Gln Ala Pro Leu Ala Phe
1               5                   10                  15

Gln Ala

<210> SEQ ID NO 27
<211> LENGTH: 18
<212> TYPE: PRT
<213> ORGANISM: Homo sapiens
```

```
<400> SEQUENCE: 27

Arg Gln Ala Pro Leu Ala Phe Gln Ala Gly Gly Arg Arg Gly Asp Phe
1               5                  10                  15

Ile Tyr

<210> SEQ ID NO 28
<211> LENGTH: 18
<212> TYPE: PRT
<213> ORGANISM: Homo sapiens

<400> SEQUENCE: 28

Gly Gly Arg Arg Gly Asp Phe Ile Tyr Val Asp Ile Phe Glu Gly His
1               5                  10                  15

Leu Arg

<210> SEQ ID NO 29
<211> LENGTH: 18
<212> TYPE: PRT
<213> ORGANISM: Homo sapiens

<400> SEQUENCE: 29

Val Asp Ile Phe Glu Gly His Leu Arg Ala Val Val Glu Lys Gly Gln
1               5                  10                  15

Gly Thr

<210> SEQ ID NO 30
<211> LENGTH: 18
<212> TYPE: PRT
<213> ORGANISM: Homo sapiens

<400> SEQUENCE: 30

Ala Val Val Glu Lys Gly Gln Gly Thr Val Leu Leu His Asn Ser Val
1               5                  10                  15

Pro Val

<210> SEQ ID NO 31
<211> LENGTH: 18
<212> TYPE: PRT
<213> ORGANISM: Homo sapiens

<400> SEQUENCE: 31

Val Leu Leu His Asn Ser Val Pro Val Ala Asp Gly Gln Pro His Glu
1               5                  10                  15

Val Ser

<210> SEQ ID NO 32
<211> LENGTH: 18
<212> TYPE: PRT
<213> ORGANISM: Homo sapiens

<400> SEQUENCE: 32

Ala Asp Gly Gln Pro His Glu Val Ser Val His Ile Asn Ala His Arg
1               5                  10                  15

Leu Glu

<210> SEQ ID NO 33
<211> LENGTH: 18
<212> TYPE: PRT
<213> ORGANISM: Homo sapiens
```

```
<400> SEQUENCE: 33

Val His Ile Asn Ala His Arg Leu Glu Ile Ser Val Asp Gln Tyr Pro
1               5                   10                  15

Thr His

<210> SEQ ID NO 34
<211> LENGTH: 18
<212> TYPE: PRT
<213> ORGANISM: Homo sapiens

<400> SEQUENCE: 34

Ile Ser Val Asp Gln Tyr Pro Thr His Thr Ser Asn Arg Gly Val Leu
1               5                   10                  15

Ser Tyr

<210> SEQ ID NO 35
<211> LENGTH: 18
<212> TYPE: PRT
<213> ORGANISM: Homo sapiens

<400> SEQUENCE: 35

Thr Ser Asn Arg Gly Val Leu Ser Tyr Leu Glu Pro Arg Gly Ser Leu
1               5                   10                  15

Leu Leu

<210> SEQ ID NO 36
<211> LENGTH: 18
<212> TYPE: PRT
<213> ORGANISM: Homo sapiens

<400> SEQUENCE: 36

Leu Glu Pro Arg Gly Ser Leu Leu Gly Gly Leu Asp Ala Glu Ala
1               5                   10                  15

Ser Arg

<210> SEQ ID NO 37
<211> LENGTH: 18
<212> TYPE: PRT
<213> ORGANISM: Homo sapiens

<400> SEQUENCE: 37

Gly Gly Leu Asp Ala Glu Ala Ser Arg His Leu Gln Glu His Arg Leu
1               5                   10                  15

Gly Leu

<210> SEQ ID NO 38
<211> LENGTH: 18
<212> TYPE: PRT
<213> ORGANISM: Homo sapiens

<400> SEQUENCE: 38

His Leu Gln Glu His Arg Leu Gly Leu Thr Pro Glu Ala Thr Asn Ala
1               5                   10                  15

Ser Leu

<210> SEQ ID NO 39
<211> LENGTH: 18
<212> TYPE: PRT
```

```
<400> SEQUENCE: 39

Thr Pro Glu Ala Thr Asn Ala Ser Leu Leu Gly Cys Met Glu Asp Leu
1               5                   10                  15

Ser Val

<210> SEQ ID NO 40
<211> LENGTH: 18
<212> TYPE: PRT
<213> ORGANISM: Homo sapiens

<400> SEQUENCE: 40

Leu Gly Cys Met Glu Asp Leu Ser Val Asn Gly Gln Arg Arg Gly Leu
1               5                   10                  15

Arg Glu

<210> SEQ ID NO 41
<211> LENGTH: 18
<212> TYPE: PRT
<213> ORGANISM: Homo sapiens

<400> SEQUENCE: 41

Asn Gly Gln Arg Arg Gly Leu Arg Glu Ala Leu Leu Thr Arg Asn Met
1               5                   10                  15

Ala Ala

<210> SEQ ID NO 42
<211> LENGTH: 18
<212> TYPE: PRT
<213> ORGANISM: Homo sapiens

<400> SEQUENCE: 42

Ala Leu Leu Thr Arg Asn Met Ala Ala Gly Cys Arg Leu Glu Glu Glu
1               5                   10                  15

Glu Tyr

<210> SEQ ID NO 43
<211> LENGTH: 18
<212> TYPE: PRT
<213> ORGANISM: Homo sapiens

<400> SEQUENCE: 43

Gly Cys Arg Leu Glu Glu Glu Tyr Glu Asp Ala Tyr Gly His
1               5                   10                  15

Tyr Glu

<210> SEQ ID NO 44
<211> LENGTH: 18
<212> TYPE: PRT
<213> ORGANISM: Homo sapiens

<400> SEQUENCE: 44

Glu Asp Asp Ala Tyr Gly His Tyr Glu Ala Phe Ser Thr Leu Ala Pro
1               5                   10                  15

Glu Ala

<210> SEQ ID NO 45
<211> LENGTH: 18
<212> TYPE: PRT
<213> ORGANISM: Homo sapiens
```

```
<400> SEQUENCE: 45

Ala Phe Ser Thr Leu Ala Pro Glu Ala Trp Pro Ala Met Glu Leu Pro
1               5                   10                  15

Glu Pro

<210> SEQ ID NO 46
<211> LENGTH: 18
<212> TYPE: PRT
<213> ORGANISM: Homo sapiens

<400> SEQUENCE: 46

Trp Pro Ala Met Glu Leu Pro Glu Pro Cys Val Pro Glu Pro Gly Leu
1               5                   10                  15

Pro Pro

<210> SEQ ID NO 47
<211> LENGTH: 18
<212> TYPE: PRT
<213> ORGANISM: Homo sapiens

<400> SEQUENCE: 47

Cys Val Pro Glu Pro Gly Leu Pro Pro Val Phe Ala Asn Phe Thr Gln
1               5                   10                  15

Leu Leu

<210> SEQ ID NO 48
<211> LENGTH: 18
<212> TYPE: PRT
<213> ORGANISM: Homo sapiens

<400> SEQUENCE: 48

Val Phe Ala Asn Phe Thr Gln Leu Leu Thr Ile Ser Pro Leu Val Val
1               5                   10                  15

Ala Glu

<210> SEQ ID NO 49
<211> LENGTH: 18
<212> TYPE: PRT
<213> ORGANISM: Homo sapiens

<400> SEQUENCE: 49

Thr Ile Ser Pro Leu Val Val Ala Glu Gly Gly Thr Ala Trp Leu Glu
1               5                   10                  15

Trp Arg

<210> SEQ ID NO 50
<211> LENGTH: 18
<212> TYPE: PRT
<213> ORGANISM: Homo sapiens

<400> SEQUENCE: 50

Gly Gly Thr Ala Trp Leu Glu Trp Arg His Val Gln Pro Thr Leu Asp
1               5                   10                  15

Leu Met

<210> SEQ ID NO 51
<211> LENGTH: 18
<212> TYPE: PRT
<213> ORGANISM: Homo sapiens
```

```
<400> SEQUENCE: 51

His Val Gln Pro Thr Leu Asp Leu Met Glu Ala Glu Leu Arg Lys Ser
1               5                   10                  15

Gln Val

<210> SEQ ID NO 52
<211> LENGTH: 18
<212> TYPE: PRT
<213> ORGANISM: Homo sapiens

<400> SEQUENCE: 52

Glu Ala Glu Leu Arg Lys Ser Gln Val Leu Phe Ser Val Thr Arg Gly
1               5                   10                  15

Ala His

<210> SEQ ID NO 53
<211> LENGTH: 18
<212> TYPE: PRT
<213> ORGANISM: Homo sapiens

<400> SEQUENCE: 53

Leu Phe Ser Val Thr Arg Gly Ala His Tyr Gly Glu Leu Glu Leu Asp
1               5                   10                  15

Ile Leu

<210> SEQ ID NO 54
<211> LENGTH: 18
<212> TYPE: PRT
<213> ORGANISM: Homo sapiens

<400> SEQUENCE: 54

Tyr Gly Glu Leu Glu Leu Asp Ile Leu Gly Ala Gln Ala Arg Lys Met
1               5                   10                  15

Phe Thr

<210> SEQ ID NO 55
<211> LENGTH: 18
<212> TYPE: PRT
<213> ORGANISM: Homo sapiens

<400> SEQUENCE: 55

Gly Ala Gln Ala Arg Lys Met Phe Thr Leu Leu Asp Val Val Asn Arg
1               5                   10                  15

Lys Ala

<210> SEQ ID NO 56
<211> LENGTH: 18
<212> TYPE: PRT
<213> ORGANISM: Homo sapiens

<400> SEQUENCE: 56

Leu Leu Asp Val Val Asn Arg Lys Ala Arg Phe Ile His Asp Gly Ser
1               5                   10                  15

Glu Asp

<210> SEQ ID NO 57
<211> LENGTH: 18
<212> TYPE: PRT
<213> ORGANISM: Homo sapiens
```

```
<400> SEQUENCE: 57

Arg Phe Ile His Asp Gly Ser Glu Asp Thr Ser Asp Gln Leu Val Leu
1               5                   10                  15

Glu Val

<210> SEQ ID NO 58
<211> LENGTH: 18
<212> TYPE: PRT
<213> ORGANISM: Homo sapiens

<400> SEQUENCE: 58

Thr Ser Asp Gln Leu Val Leu Glu Val Ser Val Thr Ala Arg Val Pro
1               5                   10                  15

Met Pro

<210> SEQ ID NO 59
<211> LENGTH: 18
<212> TYPE: PRT
<213> ORGANISM: Homo sapiens

<400> SEQUENCE: 59

Ser Val Thr Ala Arg Val Pro Met Pro Ser Cys Leu Arg Arg Gly Gln
1               5                   10                  15

Thr Tyr

<210> SEQ ID NO 60
<211> LENGTH: 18
<212> TYPE: PRT
<213> ORGANISM: Homo sapiens

<400> SEQUENCE: 60

Ser Cys Leu Arg Arg Gly Gln Thr Tyr Leu Leu Pro Ile Gln Val Asn
1               5                   10                  15

Pro Val

<210> SEQ ID NO 61
<211> LENGTH: 18
<212> TYPE: PRT
<213> ORGANISM: Homo sapiens

<400> SEQUENCE: 61

Leu Leu Pro Ile Gln Val Asn Pro Val Asn Asp Pro Pro His Ile Ile
1               5                   10                  15

Phe Pro

<210> SEQ ID NO 62
<211> LENGTH: 18
<212> TYPE: PRT
<213> ORGANISM: Homo sapiens

<400> SEQUENCE: 62

Asn Asp Pro Pro His Ile Ile Phe Pro His Gly Ser Leu Met Val Ile
1               5                   10                  15

Leu Glu

<210> SEQ ID NO 63
<211> LENGTH: 18
<212> TYPE: PRT
<213> ORGANISM: Homo sapiens
```

```
<400> SEQUENCE: 63

His Gly Ser Leu Met Val Ile Leu Glu His Thr Gln Lys Pro Leu Gly
1               5                   10                  15

Pro Glu

<210> SEQ ID NO 64
<211> LENGTH: 18
<212> TYPE: PRT
<213> ORGANISM: Homo sapiens

<400> SEQUENCE: 64

His Thr Gln Lys Pro Leu Gly Pro Glu Val Phe Gln Ala Tyr Asp Pro
1               5                   10                  15

Asp Ser

<210> SEQ ID NO 65
<211> LENGTH: 18
<212> TYPE: PRT
<213> ORGANISM: Homo sapiens

<400> SEQUENCE: 65

Val Phe Gln Ala Tyr Asp Pro Asp Ser Ala Cys Glu Gly Leu Thr Phe
1               5                   10                  15

Gln Val

<210> SEQ ID NO 66
<211> LENGTH: 18
<212> TYPE: PRT
<213> ORGANISM: Homo sapiens

<400> SEQUENCE: 66

Ala Cys Glu Gly Leu Thr Phe Gln Val Leu Gly Thr Ser Ser Gly Leu
1               5                   10                  15

Pro Val

<210> SEQ ID NO 67
<211> LENGTH: 18
<212> TYPE: PRT
<213> ORGANISM: Homo sapiens

<400> SEQUENCE: 67

Leu Gly Thr Ser Ser Gly Leu Pro Val Glu Arg Arg Asp Gln Pro Gly
1               5                   10                  15

Glu Pro

<210> SEQ ID NO 68
<211> LENGTH: 18
<212> TYPE: PRT
<213> ORGANISM: Homo sapiens

<400> SEQUENCE: 68

Glu Arg Arg Asp Gln Pro Gly Glu Pro Ala Thr Glu Phe Ser Cys Arg
1               5                   10                  15

Glu Leu

<210> SEQ ID NO 69
<211> LENGTH: 18
<212> TYPE: PRT
<213> ORGANISM: Homo sapiens
```

```
<400> SEQUENCE: 69

Ala Thr Glu Phe Ser Cys Arg Glu Leu Glu Ala Gly Ser Leu Val Tyr
1               5                   10                  15

Val His

<210> SEQ ID NO 70
<211> LENGTH: 18
<212> TYPE: PRT
<213> ORGANISM: Homo sapiens

<400> SEQUENCE: 70

Glu Ala Gly Ser Leu Val Tyr Val His Cys Gly Gly Pro Ala Gln Asp
1               5                   10                  15

Leu Thr

<210> SEQ ID NO 71
<211> LENGTH: 18
<212> TYPE: PRT
<213> ORGANISM: Homo sapiens

<400> SEQUENCE: 71

Cys Gly Gly Pro Ala Gln Asp Leu Thr Phe Arg Val Ser Asp Gly Leu
1               5                   10                  15

Gln Ala

<210> SEQ ID NO 72
<211> LENGTH: 18
<212> TYPE: PRT
<213> ORGANISM: Homo sapiens

<400> SEQUENCE: 72

Phe Arg Val Ser Asp Gly Leu Gln Ala Ser Pro Pro Ala Thr Leu Lys
1               5                   10                  15

Val Val

<210> SEQ ID NO 73
<211> LENGTH: 18
<212> TYPE: PRT
<213> ORGANISM: Homo sapiens

<400> SEQUENCE: 73

Ser Pro Pro Ala Thr Leu Lys Val Val Ala Ile Arg Pro Ala Ile Gln
1               5                   10                  15

Ile His

<210> SEQ ID NO 74
<211> LENGTH: 18
<212> TYPE: PRT
<213> ORGANISM: Homo sapiens

<400> SEQUENCE: 74

Ala Ile Arg Pro Ala Ile Gln Ile His Arg Ser Thr Gly Leu Arg Leu
1               5                   10                  15

Ala Gln

<210> SEQ ID NO 75
<211> LENGTH: 18
<212> TYPE: PRT
<213> ORGANISM: Homo sapiens
```

-continued

```
<400> SEQUENCE: 75

Arg Ser Thr Gly Leu Arg Leu Ala Gln Gly Ser Ala Met Pro Ile Leu
1               5                   10                  15

Pro Ala

<210> SEQ ID NO 76
<211> LENGTH: 18
<212> TYPE: PRT
<213> ORGANISM: Homo sapiens

<400> SEQUENCE: 76

Gly Ser Ala Met Pro Ile Leu Pro Ala Asn Leu Ser Val Glu Thr Asn
1               5                   10                  15

Ala Val

<210> SEQ ID NO 77
<211> LENGTH: 18
<212> TYPE: PRT
<213> ORGANISM: Homo sapiens

<400> SEQUENCE: 77

Asn Leu Ser Val Glu Thr Asn Ala Val Gly Gln Asp Val Ser Val Leu
1               5                   10                  15

Phe Arg

<210> SEQ ID NO 78
<211> LENGTH: 18
<212> TYPE: PRT
<213> ORGANISM: Homo sapiens

<400> SEQUENCE: 78

Gly Gln Asp Val Ser Val Leu Phe Arg Val Thr Gly Ala Leu Gln Phe
1               5                   10                  15

Gly Glu

<210> SEQ ID NO 79
<211> LENGTH: 18
<212> TYPE: PRT
<213> ORGANISM: Homo sapiens

<400> SEQUENCE: 79

Val Thr Gly Ala Leu Gln Phe Gly Glu Leu Gln Lys His Ser Thr Gly
1               5                   10                  15

Gly Val

<210> SEQ ID NO 80
<211> LENGTH: 18
<212> TYPE: PRT
<213> ORGANISM: Homo sapiens

<400> SEQUENCE: 80

Leu Gln Lys His Ser Thr Gly Gly Val Glu Gly Ala Glu Trp Trp Ala
1               5                   10                  15

Thr Gln

<210> SEQ ID NO 81
<211> LENGTH: 18
<212> TYPE: PRT
<213> ORGANISM: Homo sapiens
```

-continued

```
<400> SEQUENCE: 81

Glu Gly Ala Glu Trp Trp Ala Thr Gln Ala Phe His Gln Arg Asp Val
1               5                   10                  15
Glu Gln

<210> SEQ ID NO 82
<211> LENGTH: 18
<212> TYPE: PRT
<213> ORGANISM: Homo sapiens

<400> SEQUENCE: 82

Ala Phe His Gln Arg Asp Val Glu Gln Gly Arg Val Arg Tyr Leu Ser
1               5                   10                  15
Thr Asp

<210> SEQ ID NO 83
<211> LENGTH: 18
<212> TYPE: PRT
<213> ORGANISM: Homo sapiens

<400> SEQUENCE: 83

Gly Arg Val Arg Tyr Leu Ser Thr Asp Pro Gln His His Ala Tyr Asp
1               5                   10                  15
Thr Val

<210> SEQ ID NO 84
<211> LENGTH: 18
<212> TYPE: PRT
<213> ORGANISM: Homo sapiens

<400> SEQUENCE: 84

Pro Gln His His Ala Tyr Asp Thr Val Glu Asn Leu Ala Leu Glu Val
1               5                   10                  15
Gln Val

<210> SEQ ID NO 85
<211> LENGTH: 18
<212> TYPE: PRT
<213> ORGANISM: Homo sapiens

<400> SEQUENCE: 85

Glu Asn Leu Ala Leu Glu Val Gln Val Gly Gln Glu Ile Leu Ser Asn
1               5                   10                  15
Leu Ser

<210> SEQ ID NO 86
<211> LENGTH: 18
<212> TYPE: PRT
<213> ORGANISM: Homo sapiens

<400> SEQUENCE: 86

Gly Gln Glu Ile Leu Ser Asn Leu Ser Phe Pro Val Thr Ile Gln Arg
1               5                   10                  15
Ala Thr

<210> SEQ ID NO 87
<211> LENGTH: 18
<212> TYPE: PRT
```

```
<400> SEQUENCE: 87

Phe Pro Val Thr Ile Gln Arg Ala Thr Val Trp Met Leu Arg Leu Glu
1               5                   10                  15

Pro Leu

<210> SEQ ID NO 88
<211> LENGTH: 18
<212> TYPE: PRT
<213> ORGANISM: Homo sapiens

<400> SEQUENCE: 88

Val Trp Met Leu Arg Leu Glu Pro Leu His Thr Gln Asn Thr Gln Gln
1               5                   10                  15

Glu Thr

<210> SEQ ID NO 89
<211> LENGTH: 18
<212> TYPE: PRT
<213> ORGANISM: Homo sapiens

<400> SEQUENCE: 89

His Thr Gln Asn Thr Gln Gln Glu Thr Leu Thr Thr Ala His Leu Glu
1               5                   10                  15

Ala Thr

<210> SEQ ID NO 90
<211> LENGTH: 18
<212> TYPE: PRT
<213> ORGANISM: Homo sapiens

<400> SEQUENCE: 90

Leu Thr Thr Ala His Leu Glu Ala Thr Leu Glu Glu Ala Gly Pro Ser
1               5                   10                  15

Pro Pro

<210> SEQ ID NO 91
<211> LENGTH: 18
<212> TYPE: PRT
<213> ORGANISM: Homo sapiens

<400> SEQUENCE: 91

Leu Glu Glu Ala Gly Pro Ser Pro Pro Thr Phe His Tyr Glu Val Val
1               5                   10                  15

Gln Ala

<210> SEQ ID NO 92
<211> LENGTH: 18
<212> TYPE: PRT
<213> ORGANISM: Homo sapiens

<400> SEQUENCE: 92

Thr Phe His Tyr Glu Val Val Gln Ala Pro Arg Lys Gly Asn Leu Gln
1               5                   10                  15

Leu Gln

<210> SEQ ID NO 93
<211> LENGTH: 18
<212> TYPE: PRT
<213> ORGANISM: Homo sapiens
```

```
<400> SEQUENCE: 93

Pro Arg Lys Gly Asn Leu Gln Leu Gln Gly Thr Arg Leu Ser Asp Gly
1               5                   10                  15

Gln Gly

<210> SEQ ID NO 94
<211> LENGTH: 18
<212> TYPE: PRT
<213> ORGANISM: Homo sapiens

<400> SEQUENCE: 94

Gly Thr Arg Leu Ser Asp Gly Gln Gly Phe Thr Gln Asp Asp Ile Gln
1               5                   10                  15

Ala Gly

<210> SEQ ID NO 95
<211> LENGTH: 18
<212> TYPE: PRT
<213> ORGANISM: Homo sapiens

<400> SEQUENCE: 95

Phe Thr Gln Asp Asp Ile Gln Ala Gly Arg Val Thr Tyr Gly Ala Thr
1               5                   10                  15

Ala Arg

<210> SEQ ID NO 96
<211> LENGTH: 18
<212> TYPE: PRT
<213> ORGANISM: Homo sapiens

<400> SEQUENCE: 96

Arg Val Thr Tyr Gly Ala Thr Ala Arg Ala Ser Glu Ala Val Glu Asp
1               5                   10                  15

Thr Phe

<210> SEQ ID NO 97
<211> LENGTH: 18
<212> TYPE: PRT
<213> ORGANISM: Homo sapiens

<400> SEQUENCE: 97

Ala Ser Glu Ala Val Glu Asp Thr Phe Arg Phe Arg Val Thr Ala Pro
1               5                   10                  15

Pro Tyr

<210> SEQ ID NO 98
<211> LENGTH: 18
<212> TYPE: PRT
<213> ORGANISM: Homo sapiens

<400> SEQUENCE: 98

Arg Phe Arg Val Thr Ala Pro Pro Tyr Phe Ser Pro Leu Tyr Thr Phe
1               5                   10                  15

Pro Ile

<210> SEQ ID NO 99
<211> LENGTH: 18
<212> TYPE: PRT
<213> ORGANISM: Homo sapiens
```

-continued

```
<400> SEQUENCE: 99

Phe Ser Pro Leu Tyr Thr Phe Pro Ile His Ile Gly Gly Asp Pro Asp
1               5                   10                  15

Ala Pro

<210> SEQ ID NO 100
<211> LENGTH: 18
<212> TYPE: PRT
<213> ORGANISM: Homo sapiens

<400> SEQUENCE: 100

His Ile Gly Gly Asp Pro Asp Ala Pro Val Leu Thr Asn Val Leu Leu
1               5                   10                  15

Val Val

<210> SEQ ID NO 101
<211> LENGTH: 18
<212> TYPE: PRT
<213> ORGANISM: Homo sapiens

<400> SEQUENCE: 101

Val Leu Thr Asn Val Leu Leu Val Val Pro Glu Gly Gly Glu Gly Val
1               5                   10                  15

Leu Ser

<210> SEQ ID NO 102
<211> LENGTH: 18
<212> TYPE: PRT
<213> ORGANISM: Homo sapiens

<400> SEQUENCE: 102

Pro Glu Gly Gly Glu Gly Val Leu Ser Ala Asp His Leu Phe Val Lys
1               5                   10                  15

Ser Leu

<210> SEQ ID NO 103
<211> LENGTH: 18
<212> TYPE: PRT
<213> ORGANISM: Homo sapiens

<400> SEQUENCE: 103

Ala Asp His Leu Phe Val Lys Ser Leu Asn Ser Ala Ser Tyr Leu Tyr
1               5                   10                  15

Glu Val

<210> SEQ ID NO 104
<211> LENGTH: 18
<212> TYPE: PRT
<213> ORGANISM: Homo sapiens

<400> SEQUENCE: 104

Asn Ser Ala Ser Tyr Leu Tyr Glu Val Met Glu Arg Pro Arg Leu Gly
1               5                   10                  15

Arg Leu

<210> SEQ ID NO 105
<211> LENGTH: 18
<212> TYPE: PRT
<213> ORGANISM: Homo sapiens
```

```
<400> SEQUENCE: 105

Met Glu Arg Pro Arg Leu Gly Arg Leu Ala Trp Arg Gly Thr Gln Asp
1               5                   10                  15

Lys Thr

<210> SEQ ID NO 106
<211> LENGTH: 18
<212> TYPE: PRT
<213> ORGANISM: Homo sapiens

<400> SEQUENCE: 106

Ala Trp Arg Gly Thr Gln Asp Lys Thr Thr Met Val Thr Ser Phe Thr
1               5                   10                  15

Asn Glu

<210> SEQ ID NO 107
<211> LENGTH: 18
<212> TYPE: PRT
<213> ORGANISM: Homo sapiens

<400> SEQUENCE: 107

Thr Met Val Thr Ser Phe Thr Asn Glu Asp Leu Leu Arg Gly Arg Leu
1               5                   10                  15

Val Tyr

<210> SEQ ID NO 108
<211> LENGTH: 18
<212> TYPE: PRT
<213> ORGANISM: Homo sapiens

<400> SEQUENCE: 108

Asp Leu Leu Arg Gly Arg Leu Val Tyr Gln His Asp Asp Ser Glu Thr
1               5                   10                  15

Thr Glu

<210> SEQ ID NO 109
<211> LENGTH: 18
<212> TYPE: PRT
<213> ORGANISM: Homo sapiens

<400> SEQUENCE: 109

Gln His Asp Asp Ser Glu Thr Thr Glu Asp Asp Ile Pro Phe Val Ala
1               5                   10                  15

Thr Arg

<210> SEQ ID NO 110
<211> LENGTH: 18
<212> TYPE: PRT
<213> ORGANISM: Homo sapiens

<400> SEQUENCE: 110

Asp Asp Ile Pro Phe Val Ala Thr Arg Gln Gly Glu Ser Ser Gly Asp
1               5                   10                  15

Met Ala

<210> SEQ ID NO 111
<211> LENGTH: 18
<212> TYPE: PRT
<213> ORGANISM: Homo sapiens
```

<400> SEQUENCE: 111

Gln Gly Glu Ser Ser Gly Asp Met Ala Trp Glu Glu Val Arg Gly Val
1               5                   10                  15

Phe Arg

<210> SEQ ID NO 112
<211> LENGTH: 18
<212> TYPE: PRT
<213> ORGANISM: Homo sapiens

<400> SEQUENCE: 112

Trp Glu Glu Val Arg Gly Val Phe Arg Val Ala Ile Gln Pro Val Asn
1               5                   10                  15

Asp His

<210> SEQ ID NO 113
<211> LENGTH: 18
<212> TYPE: PRT
<213> ORGANISM: Homo sapiens

<400> SEQUENCE: 113

Val Ala Ile Gln Pro Val Asn Asp His Ala Pro Val Gln Thr Ile Ser
1               5                   10                  15

Arg Ile

<210> SEQ ID NO 114
<211> LENGTH: 18
<212> TYPE: PRT
<213> ORGANISM: Homo sapiens

<400> SEQUENCE: 114

Ala Pro Val Gln Thr Ile Ser Arg Ile Phe His Val Ala Arg Gly Gly
1               5                   10                  15

Arg Arg

<210> SEQ ID NO 115
<211> LENGTH: 18
<212> TYPE: PRT
<213> ORGANISM: Homo sapiens

<400> SEQUENCE: 115

Phe His Val Ala Arg Gly Gly Arg Arg Leu Leu Thr Thr Asp Asp Val
1               5                   10                  15

Ala Phe

<210> SEQ ID NO 116
<211> LENGTH: 18
<212> TYPE: PRT
<213> ORGANISM: Homo sapiens

<400> SEQUENCE: 116

Leu Leu Thr Thr Asp Asp Val Ala Phe Ser Asp Ala Asp Ser Gly Phe
1               5                   10                  15

Ala Asp

<210> SEQ ID NO 117
<211> LENGTH: 18
<212> TYPE: PRT
<213> ORGANISM: Homo sapiens -continued

<400> SEQUENCE: 117

Ser Asp Ala Asp Ser Gly Phe Ala Asp Ala Gln Leu Val Leu Thr Arg
1               5                   10                  15

Lys Asp

<210> SEQ ID NO 118
<211> LENGTH: 18
<212> TYPE: PRT
<213> ORGANISM: Homo sapiens

<400> SEQUENCE: 118

Ala Gln Leu Val Leu Thr Arg Lys Asp Leu Leu Phe Gly Ser Ile Val
1               5                   10                  15

Ala Val

<210> SEQ ID NO 119
<211> LENGTH: 18
<212> TYPE: PRT
<213> ORGANISM: Homo sapiens

<400> SEQUENCE: 119

Leu Leu Phe Gly Ser Ile Val Ala Val Asp Glu Pro Thr Arg Pro Ile
1               5                   10                  15

Tyr Arg

<210> SEQ ID NO 120
<211> LENGTH: 18
<212> TYPE: PRT
<213> ORGANISM: Homo sapiens

<400> SEQUENCE: 120

Asp Glu Pro Thr Arg Pro Ile Tyr Arg Phe Thr Gln Glu Asp Leu Arg
1               5                   10                  15

Lys Arg

<210> SEQ ID NO 121
<211> LENGTH: 18
<212> TYPE: PRT
<213> ORGANISM: Homo sapiens

<400> SEQUENCE: 121

Phe Thr Gln Glu Asp Leu Arg Lys Arg Arg Val Leu Phe Val His Ser
1               5                   10                  15

Gly Ala

<210> SEQ ID NO 122
<211> LENGTH: 18
<212> TYPE: PRT
<213> ORGANISM: Homo sapiens

<400> SEQUENCE: 122

Arg Val Leu Phe Val His Ser Gly Ala Asp Arg Gly Trp Ile Gln Leu
1               5                   10                  15

Gln Val

<210> SEQ ID NO 123
<211> LENGTH: 18
<212> TYPE: PRT
<213> ORGANISM: Homo sapiens -continued

```
<400> SEQUENCE: 123

Asp Arg Gly Trp Ile Gln Leu Gln Val Ser Asp Gly Gln His Gln Ala
1               5                   10                  15

Thr Ala

<210> SEQ ID NO 124
<211> LENGTH: 18
<212> TYPE: PRT
<213> ORGANISM: Homo sapiens

<400> SEQUENCE: 124

Ser Asp Gly Gln His Gln Ala Thr Ala Leu Leu Glu Val Gln Ala Ser
1               5                   10                  15

Glu Pro

<210> SEQ ID NO 125
<211> LENGTH: 18
<212> TYPE: PRT
<213> ORGANISM: Homo sapiens

<400> SEQUENCE: 125

Leu Leu Glu Val Gln Ala Ser Glu Pro Tyr Leu Arg Val Ala Asn Gly
1               5                   10                  15

Ser Ser

<210> SEQ ID NO 126
<211> LENGTH: 18
<212> TYPE: PRT
<213> ORGANISM: Homo sapiens

<400> SEQUENCE: 126

Tyr Leu Arg Val Ala Asn Gly Ser Ser Leu Val Val Pro Gln Gly Gly
1               5                   10                  15

Gln Gly

<210> SEQ ID NO 127
<211> LENGTH: 18
<212> TYPE: PRT
<213> ORGANISM: Homo sapiens

<400> SEQUENCE: 127

Leu Val Val Pro Gln Gly Gly Gln Gly Thr Ile Asp Thr Ala Val Leu
1               5                   10                  15

His Leu

<210> SEQ ID NO 128
<211> LENGTH: 18
<212> TYPE: PRT
<213> ORGANISM: Homo sapiens

<400> SEQUENCE: 128

Thr Ile Asp Thr Ala Val Leu His Leu Asp Thr Asn Leu Asp Ile Arg
1               5                   10                  15

Ser Gly

<210> SEQ ID NO 129
<211> LENGTH: 18
<212> TYPE: PRT
<213> ORGANISM: Homo sapiens
```

-continued

```
<400> SEQUENCE: 129

Asp Thr Asn Leu Asp Ile Arg Ser Gly Asp Glu Val His Tyr His Val
1               5                   10                  15

Thr Ala

<210> SEQ ID NO 130
<211> LENGTH: 18
<212> TYPE: PRT
<213> ORGANISM: Homo sapiens

<400> SEQUENCE: 130

Asp Glu Val His Tyr His Val Thr Ala Gly Pro Arg Trp Gly Gln Leu
1               5                   10                  15

Val Arg

<210> SEQ ID NO 131
<211> LENGTH: 18
<212> TYPE: PRT
<213> ORGANISM: Homo sapiens

<400> SEQUENCE: 131

Gly Pro Arg Trp Gly Gln Leu Val Arg Ala Gly Gln Pro Ala Thr Ala
1               5                   10                  15

Phe Ser

<210> SEQ ID NO 132
<211> LENGTH: 18
<212> TYPE: PRT
<213> ORGANISM: Homo sapiens

<400> SEQUENCE: 132

Ala Gly Gln Pro Ala Thr Ala Phe Ser Gln Gln Asp Leu Leu Asp Gly
1               5                   10                  15

Ala Val

<210> SEQ ID NO 133
<211> LENGTH: 18
<212> TYPE: PRT
<213> ORGANISM: Homo sapiens

<400> SEQUENCE: 133

Gln Gln Asp Leu Leu Asp Gly Ala Val Leu Tyr Ser His Asn Gly Ser
1               5                   10                  15

Leu Ser

<210> SEQ ID NO 134
<211> LENGTH: 18
<212> TYPE: PRT
<213> ORGANISM: Homo sapiens

<400> SEQUENCE: 134

Leu Tyr Ser His Asn Gly Ser Leu Ser Pro Glu Asp Thr Met Ala Phe
1               5                   10                  15

Ser Val

<210> SEQ ID NO 135
<211> LENGTH: 18
<212> TYPE: PRT
<213> ORGANISM: Homo sapiens
```

-continued

```
<400> SEQUENCE: 135

Pro Glu Asp Thr Met Ala Phe Ser Val Glu Ala Gly Pro Val His Thr
1               5                   10                  15

Asp Ala

<210> SEQ ID NO 136
<211> LENGTH: 18
<212> TYPE: PRT
<213> ORGANISM: Homo sapiens

<400> SEQUENCE: 136

Glu Ala Gly Pro Val His Thr Asp Ala Thr Leu Gln Val Thr Ile Ala
1               5                   10                  15

Leu Glu

<210> SEQ ID NO 137
<211> LENGTH: 18
<212> TYPE: PRT
<213> ORGANISM: Homo sapiens

<400> SEQUENCE: 137

Thr Leu Gln Val Thr Ile Ala Leu Glu Gly Pro Leu Ala Pro Leu Lys
1               5                   10                  15

Leu Val

<210> SEQ ID NO 138
<211> LENGTH: 18
<212> TYPE: PRT
<213> ORGANISM: Homo sapiens

<400> SEQUENCE: 138

Gly Pro Leu Ala Pro Leu Lys Leu Val Arg His Lys Lys Ile Tyr Val
1               5                   10                  15

Phe Gln

<210> SEQ ID NO 139
<211> LENGTH: 18
<212> TYPE: PRT
<213> ORGANISM: Homo sapiens

<400> SEQUENCE: 139

Arg His Lys Lys Ile Tyr Val Phe Gln Gly Glu Ala Ala Glu Ile Arg
1               5                   10                  15

Arg Asp

<210> SEQ ID NO 140
<211> LENGTH: 18
<212> TYPE: PRT
<213> ORGANISM: Homo sapiens

<400> SEQUENCE: 140

Gly Glu Ala Ala Glu Ile Arg Arg Asp Gln Leu Glu Ala Ala Gln Glu
1               5                   10                  15

Ala Val

<210> SEQ ID NO 141
<211> LENGTH: 18
<212> TYPE: PRT
<213> ORGANISM: Homo sapiens
```

-continued

<400> SEQUENCE: 141

Gln Leu Glu Ala Ala Gln Glu Ala Val Pro Pro Ala Asp Ile Val Phe
1               5                   10                  15

Ser Val

<210> SEQ ID NO 142
<211> LENGTH: 18
<212> TYPE: PRT
<213> ORGANISM: Homo sapiens

<400> SEQUENCE: 142

Pro Pro Ala Asp Ile Val Phe Ser Val Lys Ser Pro Ser Ala Gly
1               5                   10                  15

Tyr Leu

<210> SEQ ID NO 143
<211> LENGTH: 18
<212> TYPE: PRT
<213> ORGANISM: Homo sapiens

<400> SEQUENCE: 143

Lys Ser Pro Pro Ser Ala Gly Tyr Leu Val Met Val Ser Arg Gly Ala
1               5                   10                  15

Leu Ala

<210> SEQ ID NO 144
<211> LENGTH: 18
<212> TYPE: PRT
<213> ORGANISM: Homo sapiens

<400> SEQUENCE: 144

Val Met Val Ser Arg Gly Ala Leu Ala Asp Glu Pro Pro Ser Leu Asp
1               5                   10                  15

Pro Val

<210> SEQ ID NO 145
<211> LENGTH: 18
<212> TYPE: PRT
<213> ORGANISM: Homo sapiens

<400> SEQUENCE: 145

Asp Glu Pro Pro Ser Leu Asp Pro Val Gln Ser Phe Ser Gln Glu Ala
1               5                   10                  15

Val Asp

<210> SEQ ID NO 146
<211> LENGTH: 18
<212> TYPE: PRT
<213> ORGANISM: Homo sapiens

<400> SEQUENCE: 146

Gln Ser Phe Ser Gln Glu Ala Val Asp Thr Gly Arg Val Leu Tyr Leu
1               5                   10                  15

His Ser

<210> SEQ ID NO 147
<211> LENGTH: 18
<212> TYPE: PRT
<213> ORGANISM: Homo sapiens -continued

```
<400> SEQUENCE: 147

Thr Gly Arg Val Leu Tyr Leu His Ser Arg Pro Glu Ala Trp Ser Asp
1               5                   10                  15

Ala Phe

<210> SEQ ID NO 148
<211> LENGTH: 18
<212> TYPE: PRT
<213> ORGANISM: Homo sapiens

<400> SEQUENCE: 148

Arg Pro Glu Ala Trp Ser Asp Ala Phe Ser Leu Asp Val Ala Ser Gly
1               5                   10                  15

Leu Gly

<210> SEQ ID NO 149
<211> LENGTH: 18
<212> TYPE: PRT
<213> ORGANISM: Homo sapiens

<400> SEQUENCE: 149

Ser Leu Asp Val Ala Ser Gly Leu Gly Ala Pro Leu Glu Gly Val Leu
1               5                   10                  15

Val Glu

<210> SEQ ID NO 150
<211> LENGTH: 18
<212> TYPE: PRT
<213> ORGANISM: Homo sapiens

<400> SEQUENCE: 150

Ala Pro Leu Glu Gly Val Leu Val Glu Leu Glu Val Leu Pro Ala Ala
1               5                   10                  15

Ile Pro

<210> SEQ ID NO 151
<211> LENGTH: 18
<212> TYPE: PRT
<213> ORGANISM: Homo sapiens

<400> SEQUENCE: 151

Leu Glu Val Leu Pro Ala Ala Ile Pro Leu Glu Ala Gln Asn Phe Ser
1               5                   10                  15

Val Pro

<210> SEQ ID NO 152
<211> LENGTH: 18
<212> TYPE: PRT
<213> ORGANISM: Homo sapiens

<400> SEQUENCE: 152

Leu Glu Ala Gln Asn Phe Ser Val Pro Glu Gly Gly Ser Leu Thr Leu
1               5                   10                  15

Ala Pro

<210> SEQ ID NO 153
<211> LENGTH: 18
<212> TYPE: PRT
<213> ORGANISM: Homo sapiens
```

```
<400> SEQUENCE: 153

Glu Gly Gly Ser Leu Thr Leu Ala Pro Pro Leu Leu Arg Val Ser Gly
1               5                   10                  15

Pro Tyr

<210> SEQ ID NO 154
<211> LENGTH: 18
<212> TYPE: PRT
<213> ORGANISM: Homo sapiens

<400> SEQUENCE: 154

Pro Leu Leu Arg Val Ser Gly Pro Tyr Phe Pro Thr Leu Leu Gly Leu
1               5                   10                  15

Ser Leu

<210> SEQ ID NO 155
<211> LENGTH: 18
<212> TYPE: PRT
<213> ORGANISM: Homo sapiens

<400> SEQUENCE: 155

Phe Pro Thr Leu Leu Gly Leu Ser Leu Gln Val Leu Glu Pro Pro Gln
1               5                   10                  15

His Gly

<210> SEQ ID NO 156
<211> LENGTH: 18
<212> TYPE: PRT
<213> ORGANISM: Homo sapiens

<400> SEQUENCE: 156

Gln Val Leu Glu Pro Pro Gln His Gly Pro Leu Gln Lys Glu Asp Gly
1               5                   10                  15

Pro Gln

<210> SEQ ID NO 157
<211> LENGTH: 18
<212> TYPE: PRT
<213> ORGANISM: Homo sapiens

<400> SEQUENCE: 157

Pro Leu Gln Lys Glu Asp Gly Pro Gln Ala Arg Thr Leu Ser Ala Phe
1               5                   10                  15

Ser Trp

<210> SEQ ID NO 158
<211> LENGTH: 18
<212> TYPE: PRT
<213> ORGANISM: Homo sapiens

<400> SEQUENCE: 158

Ala Arg Thr Leu Ser Ala Phe Ser Trp Arg Met Val Glu Glu Gln Leu
1               5                   10                  15

Ile Arg

<210> SEQ ID NO 159
<211> LENGTH: 18
<212> TYPE: PRT
<213> ORGANISM: Homo sapiens
```

```
<400> SEQUENCE: 159

Arg Met Val Glu Glu Gln Leu Ile Arg Tyr Val His Asp Gly Ser Glu
1               5                   10                  15

Thr Leu

<210> SEQ ID NO 160
<211> LENGTH: 18
<212> TYPE: PRT
<213> ORGANISM: Homo sapiens

<400> SEQUENCE: 160

Tyr Val His Asp Gly Ser Glu Thr Leu Thr Asp Ser Phe Val Leu Met
1               5                   10                  15

Ala Asn

<210> SEQ ID NO 161
<211> LENGTH: 18
<212> TYPE: PRT
<213> ORGANISM: Homo sapiens

<400> SEQUENCE: 161

Thr Asp Ser Phe Val Leu Met Ala Asn Ala Ser Glu Met Asp Arg Gln
1               5                   10                  15

Ser His

<210> SEQ ID NO 162
<211> LENGTH: 18
<212> TYPE: PRT
<213> ORGANISM: Homo sapiens

<400> SEQUENCE: 162

Ala Ser Glu Met Asp Arg Gln Ser His Pro Val Ala Phe Thr Val Thr
1               5                   10                  15

Val Leu

<210> SEQ ID NO 163
<211> LENGTH: 18
<212> TYPE: PRT
<213> ORGANISM: Homo sapiens

<400> SEQUENCE: 163

Pro Val Ala Phe Thr Val Thr Val Leu Pro Val Asn Asp Gln Pro Pro
1               5                   10                  15

Ile Leu

<210> SEQ ID NO 164
<211> LENGTH: 18
<212> TYPE: PRT
<213> ORGANISM: Homo sapiens

<400> SEQUENCE: 164

Pro Val Asn Asp Gln Pro Pro Ile Leu Thr Thr Asn Thr Gly Leu Gln
1               5                   10                  15

Met Trp

<210> SEQ ID NO 165
<211> LENGTH: 18
<212> TYPE: PRT
<213> ORGANISM: Homo sapiens
```

<400> SEQUENCE: 165

Thr Thr Asn Thr Gly Leu Gln Met Trp Glu Gly Ala Thr Ala Pro Ile
1               5                   10                  15

Pro Ala

<210> SEQ ID NO 166
<211> LENGTH: 18
<212> TYPE: PRT
<213> ORGANISM: Homo sapiens

<400> SEQUENCE: 166

Glu Gly Ala Thr Ala Pro Ile Pro Ala Glu Ala Leu Arg Ser Thr Asp
1               5                   10                  15

Gly Asp

<210> SEQ ID NO 167
<211> LENGTH: 18
<212> TYPE: PRT
<213> ORGANISM: Homo sapiens

<400> SEQUENCE: 167

Glu Ala Leu Arg Ser Thr Asp Gly Asp Ser Gly Ser Glu Asp Leu Val
1               5                   10                  15

Tyr Thr

<210> SEQ ID NO 168
<211> LENGTH: 18
<212> TYPE: PRT
<213> ORGANISM: Homo sapiens

<400> SEQUENCE: 168

Ser Gly Ser Glu Asp Leu Val Tyr Thr Ile Glu Gln Pro Ser Asn Gly
1               5                   10                  15

Arg Val

<210> SEQ ID NO 169
<211> LENGTH: 18
<212> TYPE: PRT
<213> ORGANISM: Homo sapiens

<400> SEQUENCE: 169

Ile Glu Gln Pro Ser Asn Gly Arg Val Val Leu Arg Gly Ala Pro Gly
1               5                   10                  15

Thr Glu

<210> SEQ ID NO 170
<211> LENGTH: 18
<212> TYPE: PRT
<213> ORGANISM: Homo sapiens

<400> SEQUENCE: 170

Val Leu Arg Gly Ala Pro Gly Thr Glu Val Arg Ser Phe Thr Gln Ala
1               5                   10                  15

Gln Leu

<210> SEQ ID NO 171
<211> LENGTH: 18
<212> TYPE: PRT
<213> ORGANISM: Homo sapiens

```
<400> SEQUENCE: 171

Val Arg Ser Phe Thr Gln Ala Gln Leu Asp Gly Gly Leu Val Leu Phe
1               5                   10                  15

Ser His

<210> SEQ ID NO 172
<211> LENGTH: 18
<212> TYPE: PRT
<213> ORGANISM: Homo sapiens

<400> SEQUENCE: 172

Asp Gly Gly Leu Val Leu Phe Ser His Arg Gly Thr Leu Asp Gly Gly
1               5                   10                  15

Phe Pro

<210> SEQ ID NO 173
<211> LENGTH: 18
<212> TYPE: PRT
<213> ORGANISM: Homo sapiens

<400> SEQUENCE: 173

Arg Gly Thr Leu Asp Gly Gly Phe Pro Phe Arg Leu Ser Asp Gly Glu
1               5                   10                  15

His Thr

<210> SEQ ID NO 174
<211> LENGTH: 18
<212> TYPE: PRT
<213> ORGANISM: Homo sapiens

<400> SEQUENCE: 174

Phe Arg Leu Ser Asp Gly Glu His Thr Ser Pro Gly His Phe Phe Arg
1               5                   10                  15

Val Thr

<210> SEQ ID NO 175
<211> LENGTH: 18
<212> TYPE: PRT
<213> ORGANISM: Homo sapiens

<400> SEQUENCE: 175

Ser Pro Gly His Phe Phe Arg Val Thr Ala Gln Lys Gln Val Leu Leu
1               5                   10                  15

Ser Leu

<210> SEQ ID NO 176
<211> LENGTH: 18
<212> TYPE: PRT
<213> ORGANISM: Homo sapiens

<400> SEQUENCE: 176

Ala Gln Lys Gln Val Leu Leu Ser Leu Lys Gly Ser Gln Thr Leu Thr
1               5                   10                  15

Val Cys

<210> SEQ ID NO 177
<211> LENGTH: 18
<212> TYPE: PRT
<213> ORGANISM: Homo sapiens
```

-continued

```
<400> SEQUENCE: 177

Lys Gly Ser Gln Thr Leu Thr Val Cys Pro Gly Ser Val Gln Pro Leu
1               5                   10                  15

Ser Ser

<210> SEQ ID NO 178
<211> LENGTH: 18
<212> TYPE: PRT
<213> ORGANISM: Homo sapiens

<400> SEQUENCE: 178

Pro Gly Ser Val Gln Pro Leu Ser Ser Gln Thr Leu Arg Ala Ser Ser
1               5                   10                  15

Ser Ala

<210> SEQ ID NO 179
<211> LENGTH: 18
<212> TYPE: PRT
<213> ORGANISM: Homo sapiens

<400> SEQUENCE: 179

Gln Thr Leu Arg Ala Ser Ser Ala Gly Thr Asp Pro Gln Leu Leu
1               5                   10                  15

Leu Tyr

<210> SEQ ID NO 180
<211> LENGTH: 18
<212> TYPE: PRT
<213> ORGANISM: Homo sapiens

<400> SEQUENCE: 180

Gly Thr Asp Pro Gln Leu Leu Leu Tyr Arg Val Val Arg Gly Pro Gln
1               5                   10                  15

Leu Gly

<210> SEQ ID NO 181
<211> LENGTH: 18
<212> TYPE: PRT
<213> ORGANISM: Homo sapiens

<400> SEQUENCE: 181

Arg Val Val Arg Gly Pro Gln Leu Gly Arg Leu Phe His Ala Gln Gln
1               5                   10                  15

Asp Ser

<210> SEQ ID NO 182
<211> LENGTH: 18
<212> TYPE: PRT
<213> ORGANISM: Homo sapiens

<400> SEQUENCE: 182

Arg Leu Phe His Ala Gln Gln Asp Ser Thr Gly Glu Ala Leu Val Asn
1               5                   10                  15

Phe Thr

<210> SEQ ID NO 183
<211> LENGTH: 18
<212> TYPE: PRT
<213> ORGANISM: Homo sapiens
```

-continued

```
<400> SEQUENCE: 183

Thr Gly Glu Ala Leu Val Asn Phe Thr Gln Ala Glu Val Tyr Ala Gly
1               5                   10                  15

Asn Ile

<210> SEQ ID NO 184
<211> LENGTH: 18
<212> TYPE: PRT
<213> ORGANISM: Homo sapiens

<400> SEQUENCE: 184

Gln Ala Glu Val Tyr Ala Gly Asn Ile Leu Tyr Glu His Glu Met Pro
1               5                   10                  15

Pro Glu

<210> SEQ ID NO 185
<211> LENGTH: 18
<212> TYPE: PRT
<213> ORGANISM: Homo sapiens

<400> SEQUENCE: 185

Leu Tyr Glu His Glu Met Pro Pro Glu Pro Phe Trp Glu Ala His Asp
1               5                   10                  15

Thr Leu

<210> SEQ ID NO 186
<211> LENGTH: 18
<212> TYPE: PRT
<213> ORGANISM: Homo sapiens

<400> SEQUENCE: 186

Pro Phe Trp Glu Ala His Asp Thr Leu Glu Leu Gln Leu Ser Ser Pro
1               5                   10                  15

Pro Ala

<210> SEQ ID NO 187
<211> LENGTH: 18
<212> TYPE: PRT
<213> ORGANISM: Homo sapiens

<400> SEQUENCE: 187

Glu Leu Gln Leu Ser Ser Pro Pro Ala Arg Asp Val Ala Ala Thr Leu
1               5                   10                  15

Ala Val

<210> SEQ ID NO 188
<211> LENGTH: 18
<212> TYPE: PRT
<213> ORGANISM: Homo sapiens

<400> SEQUENCE: 188

Arg Asp Val Ala Ala Thr Leu Ala Val Ala Val Ser Phe Glu Ala Ala
1               5                   10                  15

Cys Pro

<210> SEQ ID NO 189
<211> LENGTH: 18
<212> TYPE: PRT
<213> ORGANISM: Homo sapiens
```

```
<400> SEQUENCE: 189

Ala Val Ser Phe Glu Ala Ala Cys Pro Gln Arg Pro Ser His Leu Trp
1               5                   10                  15

Lys Asn

<210> SEQ ID NO 190
<211> LENGTH: 18
<212> TYPE: PRT
<213> ORGANISM: Homo sapiens

<400> SEQUENCE: 190

Gln Arg Pro Ser His Leu Trp Lys Asn Lys Gly Leu Trp Val Pro Glu
1               5                   10                  15

Gly Gln

<210> SEQ ID NO 191
<211> LENGTH: 18
<212> TYPE: PRT
<213> ORGANISM: Homo sapiens

<400> SEQUENCE: 191

Lys Gly Leu Trp Val Pro Glu Gly Gln Arg Ala Arg Ile Thr Val Ala
1               5                   10                  15

Ala Leu

<210> SEQ ID NO 192
<211> LENGTH: 18
<212> TYPE: PRT
<213> ORGANISM: Homo sapiens

<400> SEQUENCE: 192

Arg Ala Arg Ile Thr Val Ala Ala Leu Asp Ala Ser Asn Leu Leu Ala
1               5                   10                  15

Ser Val

<210> SEQ ID NO 193
<211> LENGTH: 18
<212> TYPE: PRT
<213> ORGANISM: Homo sapiens

<400> SEQUENCE: 193

Asp Ala Ser Asn Leu Leu Ala Ser Val Pro Ser Pro Gln Arg Ser Glu
1               5                   10                  15

His Asp

<210> SEQ ID NO 194
<211> LENGTH: 18
<212> TYPE: PRT
<213> ORGANISM: Homo sapiens

<400> SEQUENCE: 194

Pro Ser Pro Gln Arg Ser Glu His Asp Val Leu Phe Gln Val Thr Gln
1               5                   10                  15

Phe Pro

<210> SEQ ID NO 195
<211> LENGTH: 18
<212> TYPE: PRT
<213> ORGANISM: Homo sapiens
```

```
<400> SEQUENCE: 195

Val Leu Phe Gln Val Thr Gln Phe Pro Ser Arg Gly Gln Leu Leu Val
1               5                   10                  15

Ser Glu

<210> SEQ ID NO 196
<211> LENGTH: 18
<212> TYPE: PRT
<213> ORGANISM: Homo sapiens

<400> SEQUENCE: 196

Ser Arg Gly Gln Leu Leu Val Ser Glu Glu Pro Leu His Ala Gly Gln
1               5                   10                  15

Pro His

<210> SEQ ID NO 197
<211> LENGTH: 18
<212> TYPE: PRT
<213> ORGANISM: Homo sapiens

<400> SEQUENCE: 197

Glu Pro Leu His Ala Gly Gln Pro His Phe Leu Gln Ser Gln Leu Ala
1               5                   10                  15

Ala Gly

<210> SEQ ID NO 198
<211> LENGTH: 18
<212> TYPE: PRT
<213> ORGANISM: Homo sapiens

<400> SEQUENCE: 198

Phe Leu Gln Ser Gln Leu Ala Ala Gly Gln Leu Val Tyr Ala His Gly
1               5                   10                  15

Gly Gly

<210> SEQ ID NO 199
<211> LENGTH: 18
<212> TYPE: PRT
<213> ORGANISM: Homo sapiens

<400> SEQUENCE: 199

Gln Leu Val Tyr Ala His Gly Gly Gly Thr Gln Gln Asp Gly Phe
1               5                   10                  15

His Phe

<210> SEQ ID NO 200
<211> LENGTH: 18
<212> TYPE: PRT
<213> ORGANISM: Homo sapiens

<400> SEQUENCE: 200

Gly Thr Gln Gln Asp Gly Phe His Phe Arg Ala His Leu Gln Gly Pro
1               5                   10                  15

Ala Gly

<210> SEQ ID NO 201
<211> LENGTH: 18
<212> TYPE: PRT
<213> ORGANISM: Homo sapiens
```

-continued

```
<400> SEQUENCE: 201

Arg Ala His Leu Gln Gly Pro Ala Gly Ala Ser Val Ala Gly Pro Gln
1               5                   10                  15

Thr Ser

<210> SEQ ID NO 202
<211> LENGTH: 18
<212> TYPE: PRT
<213> ORGANISM: Homo sapiens

<400> SEQUENCE: 202

Ala Ser Val Ala Gly Pro Gln Thr Ser Glu Ala Phe Ala Ile Thr Val
1               5                   10                  15

Arg Asp

<210> SEQ ID NO 203
<211> LENGTH: 18
<212> TYPE: PRT
<213> ORGANISM: Homo sapiens

<400> SEQUENCE: 203

Glu Ala Phe Ala Ile Thr Val Arg Asp Val Asn Glu Arg Pro Pro Gln
1               5                   10                  15

Pro Gln

<210> SEQ ID NO 204
<211> LENGTH: 18
<212> TYPE: PRT
<213> ORGANISM: Homo sapiens

<400> SEQUENCE: 204

Val Asn Glu Arg Pro Pro Gln Pro Gln Ala Ser Val Pro Leu Arg Leu
1               5                   10                  15

Thr Arg

<210> SEQ ID NO 205
<211> LENGTH: 18
<212> TYPE: PRT
<213> ORGANISM: Homo sapiens

<400> SEQUENCE: 205

Ala Ser Val Pro Leu Arg Leu Thr Arg Gly Ser Arg Ala Pro Ile Ser
1               5                   10                  15

Arg Ala

<210> SEQ ID NO 206
<211> LENGTH: 18
<212> TYPE: PRT
<213> ORGANISM: Homo sapiens

<400> SEQUENCE: 206

Gly Ser Arg Ala Pro Ile Ser Arg Ala Gln Leu Ser Val Val Asp Pro
1               5                   10                  15

Asp Ser

<210> SEQ ID NO 207
<211> LENGTH: 18
<212> TYPE: PRT
<213> ORGANISM: Homo sapiens
```

-continued

<400> SEQUENCE: 207

Gln Leu Ser Val Val Asp Pro Asp Ser Ala Pro Gly Glu Ile Glu Tyr
1               5                   10                  15

Glu Val

<210> SEQ ID NO 208
<211> LENGTH: 18
<212> TYPE: PRT
<213> ORGANISM: Homo sapiens

<400> SEQUENCE: 208

Ala Pro Gly Glu Ile Glu Tyr Glu Val Gln Arg Ala Pro His Asn Gly
1               5                   10                  15

Phe Leu

<210> SEQ ID NO 209
<211> LENGTH: 18
<212> TYPE: PRT
<213> ORGANISM: Homo sapiens

<400> SEQUENCE: 209

Gln Arg Ala Pro His Asn Gly Phe Leu Ser Leu Val Gly Gly Gly Leu
1               5                   10                  15

Gly Pro

<210> SEQ ID NO 210
<211> LENGTH: 18
<212> TYPE: PRT
<213> ORGANISM: Homo sapiens

<400> SEQUENCE: 210

Ser Leu Val Gly Gly Gly Leu Gly Pro Val Thr Arg Phe Thr Gln Ala
1               5                   10                  15

Asp Val

<210> SEQ ID NO 211
<211> LENGTH: 18
<212> TYPE: PRT
<213> ORGANISM: Homo sapiens

<400> SEQUENCE: 211

Val Thr Arg Phe Thr Gln Ala Asp Val Asp Ser Gly Arg Leu Ala Phe
1               5                   10                  15

Val Ala

<210> SEQ ID NO 212
<211> LENGTH: 18
<212> TYPE: PRT
<213> ORGANISM: Homo sapiens

<400> SEQUENCE: 212

Asp Ser Gly Arg Leu Ala Phe Val Ala Asn Gly Ser Ser Val Ala Gly
1               5                   10                  15

Ile Phe

<210> SEQ ID NO 213
<211> LENGTH: 18
<212> TYPE: PRT
<213> ORGANISM: Homo sapiens -continued

<400> SEQUENCE: 213

Asn Gly Ser Ser Val Ala Gly Ile Phe Gln Leu Ser Met Ser Asp Gly
1               5                   10                  15

Ala Ser

<210> SEQ ID NO 214
<211> LENGTH: 18
<212> TYPE: PRT
<213> ORGANISM: Homo sapiens

<400> SEQUENCE: 214

Gln Leu Ser Met Ser Asp Gly Ala Ser Pro Pro Leu Pro Met Ser Leu
1               5                   10                  15

Ala Val

<210> SEQ ID NO 215
<211> LENGTH: 18
<212> TYPE: PRT
<213> ORGANISM: Homo sapiens

<400> SEQUENCE: 215

Pro Pro Leu Pro Met Ser Leu Ala Val Asp Ile Leu Pro Ser Ala Ile
1               5                   10                  15

Glu Val

<210> SEQ ID NO 216
<211> LENGTH: 18
<212> TYPE: PRT
<213> ORGANISM: Homo sapiens

<400> SEQUENCE: 216

Asp Ile Leu Pro Ser Ala Ile Glu Val Gln Leu Arg Ala Pro Leu Glu
1               5                   10                  15

Val Pro

<210> SEQ ID NO 217
<211> LENGTH: 18
<212> TYPE: PRT
<213> ORGANISM: Homo sapiens

<400> SEQUENCE: 217

Gln Leu Arg Ala Pro Leu Glu Val Pro Gln Ala Leu Gly Arg Ser Ser
1               5                   10                  15

Leu Ser

<210> SEQ ID NO 218
<211> LENGTH: 18
<212> TYPE: PRT
<213> ORGANISM: Homo sapiens

<400> SEQUENCE: 218

Gln Ala Leu Gly Arg Ser Ser Leu Ser Gln Gln Gln Leu Arg Val Val
1               5                   10                  15

Ser Asp

<210> SEQ ID NO 219
<211> LENGTH: 18
<212> TYPE: PRT
<213> ORGANISM: Homo sapiens

```
<400> SEQUENCE: 219

Gln Gln Gln Leu Arg Val Val Ser Asp Arg Glu Glu Pro Glu Ala Ala
1               5                   10                  15

Tyr Arg

<210> SEQ ID NO 220
<211> LENGTH: 18
<212> TYPE: PRT
<213> ORGANISM: Homo sapiens

<400> SEQUENCE: 220

Arg Glu Glu Pro Glu Ala Ala Tyr Arg Leu Ile Gln Gly Pro Gln Tyr
1               5                   10                  15

Gly His

<210> SEQ ID NO 221
<211> LENGTH: 18
<212> TYPE: PRT
<213> ORGANISM: Homo sapiens

<400> SEQUENCE: 221

Leu Ile Gln Gly Pro Gln Tyr Gly His Leu Leu Val Gly Gly Arg Pro
1               5                   10                  15

Thr Ser

<210> SEQ ID NO 222
<211> LENGTH: 18
<212> TYPE: PRT
<213> ORGANISM: Homo sapiens

<400> SEQUENCE: 222

Leu Leu Val Gly Gly Arg Pro Thr Ser Ala Phe Ser Gln Phe Gln Ile
1               5                   10                  15

Asp Gln

<210> SEQ ID NO 223
<211> LENGTH: 18
<212> TYPE: PRT
<213> ORGANISM: Homo sapiens

<400> SEQUENCE: 223

Ala Phe Ser Gln Phe Gln Ile Asp Gln Gly Glu Val Val Phe Ala Phe
1               5                   10                  15

Thr Asn

<210> SEQ ID NO 224
<211> LENGTH: 18
<212> TYPE: PRT
<213> ORGANISM: Homo sapiens

<400> SEQUENCE: 224

Gly Glu Val Val Phe Ala Phe Thr Asn Phe Ser Ser Ser His Asp His
1               5                   10                  15

Phe Arg

<210> SEQ ID NO 225
<211> LENGTH: 18
<212> TYPE: PRT
<213> ORGANISM: Homo sapiens
```

-continued

<400> SEQUENCE: 225

Phe Ser Ser Ser His Asp His Phe Arg Val Leu Ala Leu Ala Arg Gly
1               5                   10                  15

Val Asn

<210> SEQ ID NO 226
<211> LENGTH: 18
<212> TYPE: PRT
<213> ORGANISM: Homo sapiens

<400> SEQUENCE: 226

Val Leu Ala Leu Ala Arg Gly Val Asn Ala Ser Ala Val Val Asn Val
1               5                   10                  15

Thr Val

<210> SEQ ID NO 227
<211> LENGTH: 18
<212> TYPE: PRT
<213> ORGANISM: Homo sapiens

<400> SEQUENCE: 227

Ala Ser Ala Val Val Asn Val Thr Val Arg Ala Leu Leu His Val Trp
1               5                   10                  15

Ala Gly

<210> SEQ ID NO 228
<211> LENGTH: 18
<212> TYPE: PRT
<213> ORGANISM: Homo sapiens

<400> SEQUENCE: 228

Arg Ala Leu Leu His Val Trp Ala Gly Gly Pro Trp Pro Gln Gly Ala
1               5                   10                  15

Thr Leu

<210> SEQ ID NO 229
<211> LENGTH: 18
<212> TYPE: PRT
<213> ORGANISM: Homo sapiens

<400> SEQUENCE: 229

Gly Pro Trp Pro Gln Gly Ala Thr Leu Arg Leu Asp Pro Thr Val Leu
1               5                   10                  15

Asp Ala

<210> SEQ ID NO 230
<211> LENGTH: 18
<212> TYPE: PRT
<213> ORGANISM: Homo sapiens

<400> SEQUENCE: 230

Arg Leu Asp Pro Thr Val Leu Asp Ala Gly Glu Leu Ala Asn Arg Thr
1               5                   10                  15

Gly Ser

<210> SEQ ID NO 231
<211> LENGTH: 18
<212> TYPE: PRT
<213> ORGANISM: Homo sapiens

```
<400> SEQUENCE: 231

Gly Glu Leu Ala Asn Arg Thr Gly Ser Val Pro Arg Phe Arg Leu Leu
1               5                   10                  15

Glu Gly

<210> SEQ ID NO 232
<211> LENGTH: 18
<212> TYPE: PRT
<213> ORGANISM: Homo sapiens

<400> SEQUENCE: 232

Val Pro Arg Phe Arg Leu Leu Glu Gly Pro Arg His Gly Arg Val Val
1               5                   10                  15

Arg Val

<210> SEQ ID NO 233
<211> LENGTH: 18
<212> TYPE: PRT
<213> ORGANISM: Homo sapiens

<400> SEQUENCE: 233

Pro Arg His Gly Arg Val Val Arg Val Pro Arg Ala Arg Thr Glu Pro
1               5                   10                  15

Gly Gly

<210> SEQ ID NO 234
<211> LENGTH: 18
<212> TYPE: PRT
<213> ORGANISM: Homo sapiens

<400> SEQUENCE: 234

Pro Arg Ala Arg Thr Glu Pro Gly Gly Ser Gln Leu Val Glu Gln Phe
1               5                   10                  15

Thr Gln

<210> SEQ ID NO 235
<211> LENGTH: 18
<212> TYPE: PRT
<213> ORGANISM: Homo sapiens

<400> SEQUENCE: 235

Ser Gln Leu Val Glu Gln Phe Thr Gln Gln Asp Leu Glu Asp Gly Arg
1               5                   10                  15

Leu Gly

<210> SEQ ID NO 236
<211> LENGTH: 18
<212> TYPE: PRT
<213> ORGANISM: Homo sapiens

<400> SEQUENCE: 236

Gln Asp Leu Glu Asp Gly Arg Leu Gly Leu Glu Val Gly Arg Pro Glu
1               5                   10                  15

Gly Arg

<210> SEQ ID NO 237
<211> LENGTH: 18
<212> TYPE: PRT
<213> ORGANISM: Homo sapiens
```

<400> SEQUENCE: 237

Leu Glu Val Gly Arg Pro Glu Gly Arg Ala Pro Gly Pro Ala Gly Asp
1               5                   10                  15
Ser Leu

<210> SEQ ID NO 238
<211> LENGTH: 18
<212> TYPE: PRT
<213> ORGANISM: Homo sapiens

<400> SEQUENCE: 238

Ala Pro Gly Pro Ala Gly Asp Ser Leu Thr Leu Glu Leu Trp Ala Gln
1               5                   10                  15
Gly Val

<210> SEQ ID NO 239
<211> LENGTH: 18
<212> TYPE: PRT
<213> ORGANISM: Homo sapiens

<400> SEQUENCE: 239

Thr Leu Glu Leu Trp Ala Gln Gly Val Pro Ala Val Ala Ser Leu
1               5                   10                  15
Asp Phe

<210> SEQ ID NO 240
<211> LENGTH: 18
<212> TYPE: PRT
<213> ORGANISM: Homo sapiens

<400> SEQUENCE: 240

Pro Pro Ala Val Ala Ser Leu Asp Phe Ala Thr Glu Pro Tyr Asn Ala
1               5                   10                  15
Ala Arg

<210> SEQ ID NO 241
<211> LENGTH: 18
<212> TYPE: PRT
<213> ORGANISM: Homo sapiens

<400> SEQUENCE: 241

Ala Thr Glu Pro Tyr Asn Ala Ala Arg Pro Tyr Ser Val Ala Leu Leu
1               5                   10                  15
Ser Val

<210> SEQ ID NO 242
<211> LENGTH: 18
<212> TYPE: PRT
<213> ORGANISM: Homo sapiens

<400> SEQUENCE: 242

Pro Tyr Ser Val Ala Leu Leu Ser Val Pro Glu Ala Ala Arg Thr Glu
1               5                   10                  15
Ala Gly

<210> SEQ ID NO 243
<211> LENGTH: 18
<212> TYPE: PRT
<213> ORGANISM: Homo sapiens

```
<400> SEQUENCE: 243

Pro Glu Ala Ala Arg Thr Glu Ala Gly Lys Pro Glu Ser Ser Thr Pro
1               5                   10                  15

Thr Gly

<210> SEQ ID NO 244
<211> LENGTH: 18
<212> TYPE: PRT
<213> ORGANISM: Homo sapiens

<400> SEQUENCE: 244

Lys Pro Glu Ser Ser Thr Pro Thr Gly Glu Pro Gly Pro Met Ala Ser
1               5                   10                  15

Ser Pro

<210> SEQ ID NO 245
<211> LENGTH: 18
<212> TYPE: PRT
<213> ORGANISM: Homo sapiens

<400> SEQUENCE: 245

Glu Pro Gly Pro Met Ala Ser Ser Pro Glu Pro Ala Val Ala Lys Gly
1               5                   10                  15

Gly Phe

<210> SEQ ID NO 246
<211> LENGTH: 18
<212> TYPE: PRT
<213> ORGANISM: Homo sapiens

<400> SEQUENCE: 246

Glu Pro Ala Val Ala Lys Gly Gly Phe Leu Ser Phe Leu Glu Ala Asn
1               5                   10                  15

Met Phe

<210> SEQ ID NO 247
<211> LENGTH: 18
<212> TYPE: PRT
<213> ORGANISM: Homo sapiens

<400> SEQUENCE: 247

Leu Ser Phe Leu Glu Ala Asn Met Phe Ser Val Ile Ile Pro Met Cys
1               5                   10                  15

Leu Val

<210> SEQ ID NO 248
<211> LENGTH: 18
<212> TYPE: PRT
<213> ORGANISM: Homo sapiens

<400> SEQUENCE: 248

Ser Val Ile Ile Pro Met Cys Leu Val Leu Leu Leu Ala Leu Ile
1               5                   10                  15

Leu Pro

<210> SEQ ID NO 249
<211> LENGTH: 18
<212> TYPE: PRT
<213> ORGANISM: Homo sapiens
```

```
<400> SEQUENCE: 249

Leu Leu Leu Leu Ala Leu Ile Leu Pro Leu Leu Phe Tyr Leu Arg Lys
1               5                   10                  15

Arg Asn

<210> SEQ ID NO 250
<211> LENGTH: 18
<212> TYPE: PRT
<213> ORGANISM: Homo sapiens

<400> SEQUENCE: 250

Leu Leu Phe Tyr Leu Arg Lys Arg Asn Lys Thr Gly Lys His Asp Val
1               5                   10                  15

Gln Val

<210> SEQ ID NO 251
<211> LENGTH: 18
<212> TYPE: PRT
<213> ORGANISM: Homo sapiens

<400> SEQUENCE: 251

Lys Thr Gly Lys His Asp Val Gln Val Leu Thr Ala Lys Pro Arg Asn
1               5                   10                  15

Gly Leu

<210> SEQ ID NO 252
<211> LENGTH: 18
<212> TYPE: PRT
<213> ORGANISM: Homo sapiens

<400> SEQUENCE: 252

Leu Thr Ala Lys Pro Arg Asn Gly Leu Ala Gly Asp Thr Glu Thr Phe
1               5                   10                  15

Arg Lys

<210> SEQ ID NO 253
<211> LENGTH: 18
<212> TYPE: PRT
<213> ORGANISM: Homo sapiens

<400> SEQUENCE: 253

Ala Gly Asp Thr Glu Thr Phe Arg Lys Val Glu Pro Gly Gln Ala Ile
1               5                   10                  15

Pro Leu

<210> SEQ ID NO 254
<211> LENGTH: 18
<212> TYPE: PRT
<213> ORGANISM: Homo sapiens

<400> SEQUENCE: 254

Val Glu Pro Gly Gln Ala Ile Pro Leu Thr Ala Val Pro Gly Gln Gly
1               5                   10                  15

Pro Pro

<210> SEQ ID NO 255
<211> LENGTH: 18
<212> TYPE: PRT
<213> ORGANISM: Homo sapiens
```

-continued

```
<400> SEQUENCE: 255

Thr Ala Val Pro Gly Gln Gly Pro Pro Gly Gly Gln Pro Asp Pro
1               5                   10                  15

Glu Leu

<210> SEQ ID NO 256
<211> LENGTH: 18
<212> TYPE: PRT
<213> ORGANISM: Homo sapiens

<400> SEQUENCE: 256

Pro Gly Gly Gln Pro Asp Pro Glu Leu Leu Gln Phe Cys Arg Thr Pro
1               5                   10                  15

Asn Pro

<210> SEQ ID NO 257
<211> LENGTH: 18
<212> TYPE: PRT
<213> ORGANISM: Homo sapiens

<400> SEQUENCE: 257

Leu Gln Phe Cys Arg Thr Pro Asn Pro Ala Leu Lys Asn Gly Gln Tyr
1               5                   10                  15

Trp Val
```

CYTOTOXICITY MEDIATION OF CELLS EVIDENCING SURFACE EXPRESSION OF MCSP

REFERENCE TO RELATED APPLICATIONS

This application is a continuation-in-part of application Ser. No. 10/810,744, filed Mar. 26, 2004, now U.S. Pat. No. 7,393,531 which is a continuation-in-part of application Ser. No. 10/762,129, filed Jan. 20, 2004, now U.S. Pat. No. 7,361,342 which is a continuation-in-part of application Ser. No. 10/743,451, filed Dec. 19, 2003, now abandoned, which is a continuation of application Ser. No. 10/348,231, filed Jan. 21, 2003, now U.S. Pat. No. 7,009,040, issued on Mar. 7, 2006, the contents of each of which are herein incorporated by reference.

FIELD OF THE INVENTION

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays, which utilize the CDMAB of the instant invention.

BACKGROUND OF THE INVENTION

Melanoma-associated chondroitin sulfate proteoglycan (MCSP) was identified independently by several investigators who developed monoclonal antibodies to human metastatic melanoma cell lines. Several antibodies were found to react with a specific antigen associated with the melanoma cell surface. The independent development of these antibodies led to the multiplicity of names for the target antigen, all of which were subsequently determined to be MCSP. MCSP has therefore also been referred to as high molecular weight melanoma associated antigen (HMW-MAA), human melanoma proteoglycan (HMP), melanoma-associated proteoglycan antigen (MPG) and melanoma chondroitin sulfate proteoglycan (mel-CSPG), and has been identified as the antigen of various specific antibodies, some of which have been set out below. MCSP was also found to be over 80 percent homologous with the rat proteoglycan NG2 and is hence also referred to by that name.

MCSP is a glycoprotein-proteoglycan complex consisting of an N-linked glycoprotein of 250 kDa and a proteoglycan component >450 kDa. The core glycoprotein is present on the surface of melanoma cells, either as a free glycoprotein or modified by the addition of chondroitin sulfate. The molecular cloning of MCSP led to the identification of several structural features. There are 3 extracellular domains containing a total of 10 cysteines (5 potential disulfide bridges), 15 possible N-linked glycosylation sites, and 11 potential chondroitin sulfate attachment sites. The transmembrane segment has a single cysteine, however the functional significance of that residue has not been established. The cytoplasmic domain has 3 threonine residues that may serve as sites for phosphorylation by protein kinase C, although it has not yet been shown that MCSP is phosphorylated.

It has been shown that MCSP is expressed in the majority of melanoma cancers, and it was originally thought that it had a very limited distribution on normal cells and other tumor types. One early study that led to this conclusion used immunohistochemistry (IHC) on normal and tumor tissues fixed with formaldehyde or methanol in order to determine the distribution of MCSP using anti-MCSP antibody B5. In this study, antibody B5 was found to react with 17 out of 22 melanoma tumors tested, 2 out of 2 astrocytomas tested, and none of the 23 carcinomas tested. Out of 22 normal tissues tested, B5 was found to bind only skin keratinocytes, lung alveolar epithelium and capillary endothelium.

Another study examined the tissue distribution of MCSP as defined by anti-MCSP antibody 9.2.27 using frozen tissue sections. Again, reactivity was found in all melanoma tissues and cell lines tested, but there was no reactivity in any of the 6 various carcinoma tumors tested. Out of the 7 fetal tissues tested, reactivity was only observed in the skin and faintly in the aorta while in adult tissues; reactivity was only seen in 3 out of 13 tissues tested.

A subsequent study examined the distribution of MCSP using the anti-MCSP antibodies B5, 9.2.27, 225.28S and A0122, all of which recognize distinct epitopes of MCSP. This study was performed on frozen tissues. It was found that all of the anti-MCSP antibodies had similar staining patterns, reacting with normal and malignant tumors of neural, mesenchymal and epithelial origin, that were previously thought to be MCSP negative. Specifically, the antibody B5 reacted with various epithelial, connective, neural and muscular tissues in the 24 organs that were tested, and reacted with 28 out of 34 various tumors tested. The authors explained that the differences between their findings and previous reports were due to the use of improved and more consistent IHC techniques, noting that choice of fixative was important, presumably leading to the conclusion that an important characteristic of the MCSP antigen is its sensitivity to the processing steps involved in IHC.

A further study was carried out in order to localize MCSP at the ultrastructural level. Immunolocalization studies using electron microscopy demonstrated that MCSP was localized almost exclusively to microspikes, a microdomain of the melanoma cell surface that may play a role in cell-cell contact and cell-substratum adhesion.

The molecular cloning of MCSP in 1996 enabled northern blot analysis of MCSP expression in tumor cell lines and normal human tissues using MCSP cDNA probes. Out of 8 various tumor cell lines tested, expression of MCSP was observed only in the melanoma cell line. MCSP expression was not seen in any of the 16 normal adult and 4 normal fetal tissues tested. The discrepancies found in different studies of tissue localization of MCSP indicate that further study may be required to elucidate the actual expression patterns of this antigen or to account for the differences that have been reported.

Since proteoglycans have been known to mediate cell-cell and cell-extracellular matrix (ECM) interactions, the role of MCSP in these processes has been investigated. MCSP has been shown to stimulate $\alpha_4\beta_1$-integrin mediated adhesion and spreading of melanoma cells, and it has also been proposed that signaling through the MCSP core protein induces recruitment and tyrosine phosphorylation of p130$^{cas}$ which may regulate cell adhesion and motility, contributing to tumor invasion and metastasis. The combination of these results indicated that MCSP may function to enhance adhesion of melanoma cells by both activating integrins and stimulating pathways that lead to cytoskeletal rearrangement.

MCSP has also been found to associate with membrane-type 3 matrix metalloproteinase (MT3-MMP), likely through the chondroitin sulfate component of MCSP. It has been suggested that MT3-MMP expression in melanomas in vivo could promote the degradation of ECM proteins in the vicinity of the growing tumor, providing space in which the tumor can expand. Therefore, the association between MT3-MMP and MCSP may be an activation step to promote melanoma invasion.

Several in vitro assays using anti-MCSP antibodies have been carried out to examine the role of MCSP in processes linked to tumor invasion and metastasis. The role of MCSP in anchorage-independent growth was assessed using the antibody 9.2.27. Melanoma cells cultured in soft agar containing 9.2.27 showed a 67-74 percent specific decrease in their colony formation. These findings suggested that MCSP might be involved in cell-cell interaction, and contribute to anchorage-independent growth. The same authors also examined the effects of blocking MCSP with 9.2.27 in assays measuring the adhesion of M14 melanoma cells on basement membranes of bovine aorta endothelial (BAE) cells. The effect of 9.2.27 treatment was compared to treatment with a control monoclonal antibody W6/32 (directed against all class I histocompatibility antigens). M14 control cells and M14 cells pretreated with antibody were plated on basement membranes of BAE cells. A significant inhibition of 27 percent in cell adhesion was observed in 9.2.27 treated cells, whereas no significant effect was observed in W6/32 treated cells. A more striking effect of cell pretreatment with 9.2.27 was the inhibition of cell spreading which was verified at the ultrastructural level using scanning electron microscopy.

Many of the antibodies that were developed against melanoma cells and determined to specifically recognize MCSP have been tested in both in vitro and in vivo assays to determine their anti-cancer effects.

Monoclonal antibody 9.2.27 recognizes the core glycoprotein component of MCSP and was one of the first antibodies investigated for tumor suppressing properties. Bumol et al. investigated 9.2.27 and a diphtheria toxin A (DTA) conjugate of 9.2.27 for immunotherapy of melanoma tumors grown in nude mice. In vitro cytotoxicity assays were first carried out by measuring the effects of both 9.2.27 and 9.2.27-DTA conjugate on protein synthesis in M21 human melanoma cells as indicated by protein incorporation of $[^{35}S]$methionine. The 9.2.27-DTA conjugate significantly inhibited protein synthesis in M21 melanoma cells, though a greater effect was seen with unconjugated DTA. There was only minimal effect achieved by 9.2.27 alone. Both the 9.2.27 and 9.2.27-DTA conjugate were investigated for anti-tumor effects in human melanoma tumor-bearing nude mice. M21 tumor mince was implanted subcutaneously and allowed to establish growth for 3 days, then mice were treated at day 3 and at 3 day intervals thereafter with either 9.2.27 or 9.2.27-DTA conjugate. Tumor volumes of treated mice were compared to those of untreated control mice. At day 18 (the last day for which data was reported), 9.2.27 treated mice showed a 64 percent inhibition of tumor growth while 9.2.27-DTA conjugate treated mice showed a 52 percent inhibition of tumor growth, compared to untreated controls. In this initial study the authors concluded that 9.2.27 and 9.2.27-DTA conjugate were approximately equivalent in their effect on suppression of growth of M21 melanoma tumors in nude mice. While this initial study reports in vivo suppression of tumor growth by treatment with 9.2.27, several subsequent studies, including those by the same authors, have demonstrated that naked 9.2.27 did not exhibit any anti-tumor effects in vivo. Collectively, as outlined below, the experiments carried out to investigate the utility of using 9.2.27 to treat human tumors have demonstrated that, although cancer cells were targeted by 9.2.27, no anti-cancer activity resulted from treatment with the naked antibody.

A phase I clinical trial was carried out which was designed to give large doses of 9.2.27 in anticipation of later therapeutic studies with 9.2.27 immunoconjugates. Eight patients with malignant melanoma whose tumors reacted with 9.2.27 by flow cytometry and/or immunoperoxidase staining, received single doses of antibody intravenously, twice weekly on a dose escalating scale of 1, 10, 50, 100 and 200 mg. Although none of the patients experienced significant toxicity and 9.2.27 localized to the metastatic melanoma nodules, no clinical responses were observed.

In a later study, 9.2.27 was conjugated to the chemotherapeutic drug doxorubicin (DXR), and the conjugate was investigated for growth inhibition of melanoma in vitro and in vivo. Growth inhibition of M21 cells treated with the DXR-9.2.27 conjugate was measured using a $[^3H]$thymidine incorporation assay. The conjugate showed specific dose-dependent growth inhibition of the M21 target cells and no effect on an MCSP negative control cell line. No in vitro assays were carried out examining effects of 9.2.27 alone. To investigate the DXR-9.2.27 conjugate in vivo, M21 cells were injected subcutaneously and allowed to establish a tumor for 8-10 days. Injections were given intravenously at day 10 and at 3 day intervals thereafter for 30 days. Significant suppression of tumor growth was seen only in mice treated with the DXR-9.2.27 conjugate. Both DXR treatment alone and 9.2.27 treatment alone failed to suppress tumor growth; a mixture of 9.2.27 and DXR showed similar negative effects.

Another study was carried out investigating the effects of a 9.2.27 conjugate. Schrappe et al. conjugated the chemotherapeutic agent 4-desacetylvinblastine-3-carboxyhydrazide (DAVLBHY) to 9.2.27 and tested its effect on human gliomas. Nude mice were injected with U87MG (a human glioma cell line) cells subcutaneously and the animals were treated on days 2, 5, 7, and 9. Tumor volume was most effectively reduced by the 9.2.27-DAVLBHY conjugate. Control groups, which were treated with either PBS or 9.2.27 alone, developed fast growing tumors and there was no reduction in tumor volume in 9.2.27 treated mice compared to mice treated with PBS.

Antibody 225.28S was made against the human M21 melanoma cell line, and was initially described as reacting with a high molecular weight melanoma associated antigen. This molecule was subsequently shown to be the same molecule as MCSP. An early study tested the cytolytic ability of 225.28S, an $IgG_{2a}$, on a human melanoma cell line and compared it to another anti-MCSP antibody, clone 653.40S that was an $IgG_1$. 225.28S and 653.40S were determined to recognize the same, or spatially close, antigenic determinants on MCSP. It was found that neither antibody could lyse melanoma cells in conjunction with complement in in vitro assays. Both antibodies could mediate lysis of target melanoma cells in an antibody-dependent cell-mediated (ADCC) cytotoxicity assay, with 225.28S exhibiting a higher lytic activity than 653.40S. However, lysis of melanoma cells was only obtained with a significantly higher effector/target cell ratio than had been reported by others using anti-melanoma antigen antibodies. The authors concluded that the lack of cytolytic activity of these antibodies in conjunction with human complement and the high effector/target cell ratio required for lysis to occur in ADCC suggested that the injection of monoclonal antibodies into melanoma patients was not likely to cause the destruction of tumor cells. The authors suggested that the immunotherapeutic use of these antibodies should be limited to utilizing them as carriers of radioisotope, chemotherapeutic or toxic agents.

Naked antibody 225.28S was investigated for its therapeutic potential in a phase I trial where it was delivered intravenously in 10 mg doses to 2 patients with end-stage melanoma. Although no clinically adverse or major toxic effects were noted that could be ascribed to the administration of the antibody, there was also no positive therapeutic response.

Antibody 225.28S was conjugated to purothionin, a low molecular weight polypeptide that is especially toxic to dividing cells, and was tested for its in vitro toxicity to the human melanoma cell line Colo 38. It was found that the culture of Colo 38 cells with the 225.28S-purothionin conjugate for 24 hr inhibited $^3$H-thymidine uptake. In addition, the viability of Colo 38 cells was dramatically reduced in cultures incubated with the conjugate for 7 days. Although in vitro toxicity was observed, there was still a fraction of melanoma cells that survived the 225.28S-purothionin treatment. The authors suggested that the immunotherapy of malignant diseases may have to rely on cocktails of monoclonal antibodies to distinct tumor associated antigens as carriers of toxic agents, indicating that 225.8S conjugate alone would not be sufficient for treatment of cancer. The effect of 225.28S-purothionin conjugate treatment was evaluated on the growth of human melanoma in nude mice. Colo 38 cells were implanted either subcutaneously or intraperitoneally in nude mice. Treatments were made on days 1, 3 and 5 for the intraperitoneal implanted mice and on days 1, 3, 5 and 20 for the subcutaneous implanted mice. Survival was monitored for all mice. The only statistically significant prolongation of survival was observed in the intraperitoneal implanted mice that were treated with the 225.28S-purothionin conjugate. 225.28S alone, purothionin alone or a mixture of 225.28S and purothionin did not enhance survival in either the intraperitoneal or the subcutaneous implanted mice. Tumor volume was also recorded for the subcutaneous implanted mice and it was found that only the 225.28S-purothionin conjugate treatment significantly reduced tumor volume. Treatment with 225.28S alone did not result in a reduction of tumor volume.

225.28S was also conjugated to the chemotherapeutic drug methotrexate (MTX) and its effects on tumor growth were investigated in vivo. Nude mice were inoculated subcutaneously with M21 human melanoma cells and treated on days 1, 4, 7, 10 and 14. The MTX-225.28S conjugate was the only treatment that inhibited tumor growth. 225.28S alone, MTX alone or a mixture of 225.28S and MTX failed to inhibit tumor growth.

225.28S was used in a study designed to investigate the potential toxic effects in humans due to the administration of a reagent of a xenogenic nature. 85 patients with metastatic cutaneous melanoma were administered either intact 225.28S or the F(ab')$_2$ fragment that were labeled with $^{131}$I, $^{123}$I, $^{111}$In, or $^{99}$Tc. The amount of injected antibody ranged from 14 to 750 μg. No clinically detectable side effects were observed in any of the patients. No clinical response was reported, though it was not necessarily anticipated as this study was designed for toxologic purposes.

225.28S was used to generate murine anti-idiotypic monoclonal antibodies including the antibody MF11-30, which bears the mirror image of MCSP. MF11-30 has been shown to induce the development of anti-MCSP antibodies in both a syngeneic and xenogeneic system. MF11-30 was tested in 2 clinical trials in escalating doses designed to test the toxicity and response in patients with advanced malignant melanoma. In both studies there were few side effects due to administration of the antibody and the therapy was well tolerated. In the second trial the average survival of 7 patients who developed anti-anti-idiotypic antibodies with a titer of at least 1:8 and displayed no marked changes in the level of serum MCSP was 55 weeks (range 16-95), which was significantly higher than the remaining 12 patients (who developed anti-antiidiotypic antibodies with a titer of 1:4 or less and displayed an increase in the serum level of MCSP) whose average survival was 19 weeks (range 8-57).

Antibody 763.74 was also generated against melanoma cells and recognizes MCSP. There have not been any reports of in vitro or in vivo anti-cancer effects of antibody 763.74, however this antibody was also used to generate murine anti-idiotypic monoclonal antibodies. One of these antibodies, MK2-23, bears the internal image of the determinant defined by the anti-MCSP antibody 763.74. In preclinical experiments, immunization with MK2-23 was shown to induce the development of anti-MCSP antibodies in both a syngeneic host (BALB/c mice) and in a xenogenic host (rabbit). The immunogenicity of MK2-23 was markedly enhanced when it was conjugated to the carrier protein keyhole limpet hemocyanin (KLH) and administered with an adjuvant. A clinical trial was carried out to characterize the humoral response induced by MK2-23 in patients with melanoma. 25 patients with stage IV melanoma were immunized on days 0, 7 and 28 with 2 mg subcutaneous injections of MK2-23 conjugated to KLH and mixed with *Bacillus* Calmette Guerin (BCG). Additional injections were given if the titer of anti-anti-idiotypic antibodies was low. Approximately 60 percent of the patients who were immunized with MK2-23 developed anti-MCSP antibodies, although the level and affinity of the anti-MCSP antibodies were low. It was found that survival of patients who developed anti-MCSP antibodies after immunizaiton with MK2-23 was significantly longer than those who did not. The median survival of patients who developed anti-MCSP antibodies was 52 weeks (range 19-93) while the median survival of the 9 patients without detectable anti-MCSP antibodies in their sera was 19 weeks (range 9-45). Three patients who developed anti-MCSP antibodies experienced a partial remission of their disease. Although promising results were achieved in this study, 40 percent of the patients immunized with MK2-23 did not respond with detectable anti-MCSP antibodies. As well, the 3 patients who had achieved partial remission all eventually experienced recurrence of disease. An attempt was made to increase the immunogenicity of MK2-23 by pretreatment of patients with a low dose of cyclophosphamide (CTX), which had been reported to enhance the cellular and humoral response to tumor associated antigens by selectively inactivating some sets of suppressor cells. However, no effects of pretreatment with CTX on the immunogenicity of MK2-23 were detected.

Monoclonal antibody 48.7 was developed against the human metastatic melanoma cell line M1733 and was reported to react against a molecule subsequently determined to be MCSP. 48.7 was administered in a phase I clinical trial in combination with the murine monoclonal antibody 96.5, which is directed against the transferrin-like cell surface glycoprotein p97 that is present on human melanomas. Five patients received 2 mg each of mAbs 96.5 and 48.7 on day 1, 10 mg each on day 2, and 25 mg each on days 3 through 10. Treatment was well tolerated; however there were no clinical responses to treatment and disease progression occurred in all patients. These two antibodies were investigated in a separate clinical trial where 3 patients with melanoma metastatic to the central nervous system were treated with radiolabeled Fab fragments of either one of these antibodies. Two patients received 5 mg doses of $^{131}$I-labeled Fab fragment of 48.7 in conjunction with osmotic opening of the blood-brain barrier (BBB) in an effort to enhance entry of the antibody into tumors in the brain. The osmotic BBB modification increased the delivery of Fab to the tumor-bearing hemisphere and spinal fluid, but clear persistent localization of the antibody to the tumor was not shown. The authors hypothesized that the lack of localization may have been due to an inadequate dose of the antibody.

Melimmune was a dual preparation of two murine anti-idiotypic antibodies, Melimmune-1 (I-Mel-1) and Melimmune-2 (I-Mel-2), which mimic separate epitopes of MCSP. I-Mel-1 was a subclone of the anti-idiotypic antibody MF11-30, which was developed against the anti-MCSP antibody 225.28 (as previously discussed). I-Mel-1 was shown to induce an anti-MCSP response in rabbits. I-Mel-2 was an anti-idiotypic antibody developed against the anti-MCSP antibody MEM136, which reacts to a different epitope on MCSP than does 225.28. I-Mel-2 was also shown to induce an anti-MCSP response in rabbits. The Melimmune preparation, which contained a 1:1 composition of I-Mel-1 and I-Mel-2, was tested in a phase I trial of 21 patients with resected melanoma without evidence of metastatic disease. Detailed immune response analysis was reported for 12 of these patients enrolled in a single institution. Patients received Melimmune on 1 of 2 treatment schedules with doses that ranged from 0.2 to 4.0 mg (0.1 to 2.0 mg each of I-Mel-1 and I-Mel-2). All patients developed both anti-I-Mel-1 and anti-I-Mel-2 antibodies with the peak antibody response to I-Mel-2 greater than that to I-Mel-1 in 10 out of 12 patients. However, this study was unable to demonstrate induction of specific antibodies to MCSP since none of the patient's sera was able to inhibit either binding of radiolabeled 225.28 to MCSP expressing Mel-21 cells, or binding of radiolabeled MEM136 to Mel-21 cells. A direct cell binding assay was also used to assay for the presence of anti-MCSP antibodies in patients sera; however, there was no difference in the binding of preimmune sera compared to postimmune sera to M21 cells in a FACS based assay.

I-Mel-2 was tested in a separate clinical trial where 26 patients with metastatic melanoma were treated with 2 mg I-Mel-2 and either 100 or 250 µg of the adjuvant SAF-m delivered intramuscularly biweekly for 4 weeks and then bimonthly until disease progression. Anti-MCSP antibodies were detected in 5 of the 26 patients using an inhibition radioimmunoassay. Of the 5 patients with detectable anti-MCSP antibodies, 1 patient experienced a complete remission, 1 had stable disease and the other 3 had progressive disease. The patient with complete remission had the highest titer of anti-MCSP antibodies (1:1500).

PRIOR PATENTS

U.S. Pat. No. 5,270,202 (and its related patents: WO9216646A1, EP0576570A1) teaches an anti-idiotypic antibody, IMelpg2 (also known as "IM32") to MEM136, an antibody directed to human melanoma-associated proteoglycan (also known as "HMW-MAA"). The IMelpg2 antibody was shown to be directed to MEM136 specifically, and suggested to be of use for the diagnosis and treatment of disease in which cells expressed the MPG epitope. Although there was an effect of IMelpg2 on tumor cell invasion, as determined by in vitro assays it was neither the most effective antibody tested, nor was there indications of in vivo anti-tumor effects despite showing an Ab3 response.

EP0380607B1 teaches anti-idiotypic antibodies to the Mab 225.28 which has specificity for an undefined epitope of HMW-MAA. These antibodies are useful as active immunotherapy for melanoma. Both MF11-30 and IMelpg1, and polyclonal anti-idiotypic antibodies to 225.28 have been reported and evaluated in animal models with MF11-30 undergoing clinical trials in melanoma patients, although there was no supporting data. MF11-30 can induce 225.28 idiotypic antibodies. The IMelpg1 cell line was derived from treating the MF11-30 cell line with BM Cycline and testing for the absence of mycoplasma contamination. Although antibodies to IMelpg1 can be induced in rabbit sera, and be shown to bind to the Colo38 melanoma cell, there was no indication of tumorcidal activity, either in vitro or in vivo.

U.S. Pat. No. 4,879,225 teaches the production of antibodies from insoluble immune complexes. In this case rat anti-idiotypic antibodies to Mab 9.2.27, an antibody directed against the HMW-MAA, were generated by immoblizing 9.2.27 on protein A-Sepharose for use as an antigen. Antibodies to melanoma cells were produced using a variety of cell or cell lysate complexes conjugated to Sepharose. Murine monoclonal antibodies that bound to melanoma cells, but not normal T-cells or B-cells were compared to 9.2.27. Those that had similar properties to 9.2.27 were selected for further characterization: NR-ML-02, NR-ML-03, NR-ML-04, NR-ML-05, NR-ML-06. Each of these antibodies were positive in a sandwich ELISA assay using 9.2.27 as the capture antibody and soulblized SK MEL-28 melanoma membranes as an antigen source. Further these antibodies were characterized as recognizing melanoma tumor cells, and also reacting with smooth muscle and endothelial cells. An additional 61 anti-proteoglycan antibodies were produced with 10 recognizing the same determinant as NR-ML-02/NR-ML-04, 3 antibodies recognized the same determinant as NR-ML-03 or NR-ML-05; 45 did not recognize the same epitope as determined by the 5 antibodies. In U.S. Pat. No. 5,084,396 these antibodies were radiolabelled and compared with 9.2.27 for tumor uptake in nude mice bearing melanoma xenografts. The tumor uptake was the greatest for NR-ML-05 and NR-ML-02, then 9.2.27, and then NR-ML-02. In neither of these inventions were there indications that these antibodies produced reduction in tumor burden of cancerous disease, nor enhanced survival of mammals having cancerous disease.

U.S. Pat. No. 5,034,223 teaches a method of enhancing delivery of conjugated antibodies to tissues bearing tumor-associated antigens by pretreating with a non-conjugated blocking antibody. Antibodies to HMW-MAA, 9.2.27 and NR-ML-05, were conjugated to technicium 99 (Tc-99) and were administered in the clinical setting after prior administration of unlabelled Mab NR-2AD, an antibody with an anti-idiotype specific for only 1 patient's B-cell lymphoma. Since these studies were designed using Tc-99 as a reporter radioisotope, which does not have cytotoxic, or radioablative effects there was no evidence of anti-tumor effects although there was enhanced uptake of the anti-HMW-MAA antibodies through the use of this process.

U.S. Pat. No. 5,580,774 teaches the construction of a chimeric antibody using the antibody genes that encode Mab 9.2.27. No disclosures regarding the diagnosis or treatment of cancerous disease using the chimeric antibody were made.

U.S. Pat. Nos. 5,493,009 and 5,780,029 teaches the murine anti-idiotypic antibody MK2-23, and its conjugates, directed against an anti-HMW-MAA antibody, 763.74. MK2-23 can bind directly to 763.74 and inhibit 763.74 binding to Colo 38 melanoma cells. Further, Ab3 elicited by MK2-23 can directly bind HMW-MAA and can competitively inhibit 763.74 binding to Colo 38 melanoma cells. Active immunotherapy was carried out in a clinical trial in stage IV melanoma patients with MK2-23. In 89 percent of patient's post-immunization sera reacted with Colo 38 melanoma cells, and inhibited binding of 763.74 to Colo 38 cells suggesting induction of Ab3 antibodies. In 6 of 15 patients there was a reduction in size of metastatic lesions reported but study details were not furnished. The specificity of the antibodies in patient sera was partially characterized and it is unclear whether Ab3 antibodies, to the extent that they were present, were responsible for any of the clinical response observed, since the 763.74 antibody did not have innate anti-tumor effects. U.S. Pat. No. 5,866,124 teaches the chimeric anti-idiotypic antibody MK2-CHγ1, and its derivatives, directed against an anti-HMW-MAA antibody, 763.74, derived from MK2-23.

A number of inventions, such as U.S. Pat. Nos. 5,017,693, 5,707,603, 5,817,774, 6,248,870, 5,112,954, 6,238,667, teach conjugating compounds to antibodies directed against HMW-MAA but fail to disclose their utility in treatment of cancerous disease. Importantly, were these antibodies effective as anti-cancer therapies alone, they would not require a conjugate to impart either cytotoxic or cytostastic effects.

These patents and patent applications identify MCSP antigens and related antibodies but fail to disclose the isolated monoclonal antibody of the instant invention, or to teach or suggest the utility of the isolated monoclonal antibody of the instant invention.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies, which are useful in treating a cancerous disease. For the purpose of this document, the terms "antibody" and "monoclonal antibody" (mAb) may be used interchangeably and refer to intact immunoglobulins produced by hybridomas (e.g. murine or human), immunoconjugates and, as appropriate, immunoglobulin fragments and recombinant proteins derived from said immunoglobulins, such as chimeric and humanized immunoglobulins, F(ab') and F(ab')$_2$ fragments, single-chain antibodies, recombinant immunoglobulin variable regions (Fv)s, fusion proteins etc. It is well recognized in the art that some amino acid sequence can be varied in a polypeptide without significant effect on the structure or function of the protein. In the molecular rearrangement of antibodies, modifications in the nucleic or amino acid sequence of the backbone region can generally be tolerated. These include, but are not limited to, substitutions (preferred are conservative substitutions), deletions or additions. Furthermore, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, or hematogenous cells, thereby forming antibody conjugates.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies and/or a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

Using substantially the process of U.S. Pat. No. 6,180,357, and as disclosed in Ser. No. 10/348,231, the mouse monoclonal antibody 11BD-2E11-2 was obtained following immunization of mice with cells from a patient's breast tumor biopsy. The 11BD-2E11-2 antigen was expressed on the cell surface of several human cell lines from different tissue origins. The breast cancer cell line MCF-7 and ovarian cancer cell line OVCAR-3 were susceptible to the cytotoxic effects of 11BD-2E11-2 in vitro.

The result of 11BD-2E11-2 cytotoxicity against MCF-7 and OVCAR-3 cells in culture was further extended by its anti-tumor activity towards these cancer cells when transplanted into mice (as disclosed in Ser. No. 10/762,129). Preclinical xenograft tumor models are considered valid predictors of therapeutic efficacy.

In a preventative in vivo model of human breast cancer, 11BD-2E11-2 prevented tumor growth and reduced tumor burden (as disclosed in Ser. No. 10/762,129). At day 51 (soon after last treatment), the mean tumor volume in the 11BD-2E11-2 treated group was 20 percent of the isotype control. Monitoring continued past 280 days post-treatment. 40 percent of the 11BD-2E11-2 treatment group was still alive at over 7.5 months post-implantation. Conversely, the isotype control group had 100 percent mortality after 6.5 months post-treatment. Therefore 11BD-2E11-2 enhanced survival and decreased the tumor burden compared to the control-treated groups in a well-established model of human breast cancer.

To determine if 11BD-2E11-2 was efficacious in more than one model of human breast cancer, its anti-tumor activity against MDA-MB-468 (MB-468) cells in an established model of breast cancer was determined (as disclosed in Ser. No. 10/810,744). 11BD-2E11-2 reduced tumor growth by 25 percent in comparison to the buffer control. Therefore, 11BD-2E11-2 was effective in preventing tumor growth in an established as well as a preventative breast cancer xenograft model. In addition, 11BD-2E11-2 displayed anti-tumor activity in at least two different models of breast cancer.

In addition to the beneficial effects in a model of human breast cancer, 11BD-2E11-2 treatment also had anti-tumor activity against OVCAR-3 cells in a preventative ovarian cancer model (as disclosed in Ser. No. 10/762,129). In this model, body weight was used as a surrogate measure of tumor progression. At day 80 post-implantation (16 days after the end of treatment) the mice in the treated group had 87.6 percent the mean body weight of the control group (p=0.015). Thus, 11BD-2E11-2 treatment was efficacious as it delayed tumor progression compared to the buffer control treated group in a well-established model of human ovarian cancer. The anti-tumor activities of 11BD-2E11-2, in several different cancer models, make it an attractive anti-cancer therapeutic agent.

To determine if 11BD-2E11-2 was efficacious in more than one model of human ovarian cancer, its anti-tumor activity against ES-2+SEAP cells (ES-2 ovarian cancer cells transfected with human placental secreted alkaline phosphatase (SEAP)) in an established model of ovarian cancer was determined (as disclosed in Ser. No. 10/810,744). 11BD-2E11-2 enhanced survival in a cohort of mice in the treatment group in comparison to buffer control. In addition, 1 mouse within the 11BD-2E11-2 treatment group displayed greatly reduced circulating SEAP levels after treatment. Circulating SEAP levels can be used as an indicator of tumor burden. Therefore, 11BD-2E11-2 was effective in preventing tumor growth in an established as well as a preventative ovarian cancer xenograft model. In addition, 11BD-2E11-2 displayed anti-tumor activity in two different models of human ovarian cancer.

Biochemical data indicated that the antigen for 11BD-2E11-2 is MCSP (as disclosed in Ser. No. 10/810,744) and previous immunohistochemical analysis and in vitro studies performed in other laboratories have demonstrated the expression of MCSP on melanoma cells and have indicated a role for MCSP in tumor adhesion, invasion and metastasis. Consequently, the efficacy of 11BD-2E11-2 was determined in both a preventative and established model of human melanoma. In the preventative model of melanoma, on day 55 (5 days after the end of treatment), the mean tumor volume in the 11BD-2E11-2 treated group was 58 percent of the buffer control treated group (p=0.046). In the established model, the antibody 11BD-2E11-2 suppressed tumor growth by 49 percent in comparison to the buffer control treated group after the treatment period. The result did not reach significance (p=0.1272) due to the limited number of animals in this experiment, but the trend was clear. Therefore, 11BD-2E11-2 was effective in preventing tumor growth in an established as well as a preventative melanoma cancer xenograft model. In addition, 11BD-2E11-2 displayed anti-tumor activity in two different models of human breast and ovarian cancer and in a human melanoma model.

In order to validate the 11BD-2E11-2 epitope as a drug target, the expression of 11BD-2E11-2 antigen in frozen normal human tissues was determined (as disclosed in Ser. No. 10/810,744). By IHC staining with 11BD-2E11-2, the majority of the tissues failed to express the 11BD-2E11-2 antigen, including the cells of the vital organs, such as the liver, kidney and heart. Albeit, there was staining to the smooth muscle fibers of blood vessels in almost all of the tissues. There was also epithelial staining for some of the tissues.

Localization of the 11BD-2E11-2 antigen and its prevalence within breast cancer patients is important in assessing the benefits of 11BD-2E11-2 immunotherapy to patients and designing effective clinical trials. To address 11BD-2E11-2 antigen expression in breast tumors from cancer patients, tumor tissue samples from 8 (7 additional samples were completely detached or not representative of the tumor on the microarray slide) individual breast cancer patients were screened for expression of the 11BD-2E11-2 antigen (as disclosed in Ser. No. 10/810,744). The results of the study showed that 62 percent of tissue samples positively stained for the 11BD-2E11-2 antigen. Expression of 11BD-2E11-2 within patient samples appeared specific for cancer cells as staining was restricted to malignant cells. In addition, 11BD-2E11-2 stained 0 of 3 (2 additional samples again were completely detached from the microarray slide) samples of normal tissue from breast cancer patients. When tumors were analyzed based on their stage, or degree to which the cancer advanced, results did not suggest a trend towards greater positive expression with higher tumor stage for 11BD-2E11-2. However, the result was limited by the small sample size.

Localization of the 11BD-2E11-2 antigen and its prevalence within melanoma cancer patients population was determined because the antigen for 11BD-2E11-2 is MCSP (as disclosed in Ser. No. 10/810,744) and that previous immunohistochemical analysis and in vitro studies performed in other laboratories have demonstrated the expression of MCSP on melanoma cells. This is important in assessing the benefits of 11BD-2E11-2 immunotherapy for melanoma patients and designing effective clinical trials. To address 11BD-2E11-2 antigen expression in melanoma tumors from cancer patients, tumor tissue samples from 33 individual melanoma cancer patients were assessed for expression of the 11BD-2E11-2 antigen. The results of the study showed that 67 percent of tissue samples stained positively for the 11BD-2E11-2 antigen. Expression of 11BD-2E11-2 within patient samples appeared specific for cancer cells as staining was restricted to malignant cells. In addition, 11BD-2E11-2 stained 0 of 6 available samples of normal tissue from melanoma cancer patients.

Biochemical data indicate that the antigen recognized by 11BD-2E112 is MCSP (as disclosed in Ser. No. 10/810,744). This was supported by studies showing that 11BD-2E11-2 immunoprecipitated protein was recognized by an antibody to the rat homologue of MCSP, and that anti-MCSP immunoprecipitated protein was recognized by 11BD-2E11-2. These IHO and biochemical results demonstrate that 11BD-2E11-2 bound to the MCSP antigen. Thus, the preponderance of evidence showed that 11BD-2E11-2 mediated anti-cancer effects through ligation of a unique epitope present on MCSE. Additional biochemical data, as outlined herein, also demonstrate that the antigen recognized by 11BD-2E11-2 is MCSP. These antibody epitope mapping results indicated that 11BD-2E11-2 may bind to a discontinuous epitope with two major binding sites.

In toto, this data demonstrates that the 11BD-2E11-2 antigen is a cancer associated antigen and is expressed in humans, and is a pathologically relevant cancer target. Further, this data also demonstrates the binding of the 11BD-2E11-2 antibody to human cancer tissues, and can be used appropriately for assays that can be diagnostic, predictive of therapy, or prognostic. In addition, the cell localization of this antigen is indicative of the cancer status of the cell due to the lack of expression of the antigen in most non-malignant cells, and this observation permits the use of this antigen, its gene or derivatives, its protein or its variants to be used for assays that can be diagnostic, predictive of therapy, or prognostic.

A number of distinct anti-MCSP antibodies have been developed and tested in many in vitro and in vivo systems. In pre-clinical models, with the exception of one study that was not reproduced, naked anti-MCSP antibodies have been shown to be ineffective in tumor reduction or enhancement of survival in several different melanoma models and one glioma model; other cancer types have not been studied with anti-MCSP antibodies. All trials of naked anti-MCSP antibodies in humans have failed to result in any positive clinical outcomes. Naked 11BD-2E11-2 has been shown to enhance survival and decrease tumor burden in murine models of human breast cancer. 11BD-2E11-2 has also inhibited tumor progression and enhanced survival in murine models of human ovarian cancer. Anti-MCSP antibodies have been conjugated to numerous toxic or chemotherapeutic agents, and these conjugates have demonstrated positive in vivo results when tested in murine models of melanoma. There have been no reports of anti-MCSP conjugates tested in humans, so the safety of these conjugates is not known. Delivery of monoclonal antibody alone however has been well tolerated with little, if any associated toxicity. Therefore if treatment of a cancer patient with a naked anti-MCSP antibody could result in a positive clinical outcome, it would be beneficial and an improvement upon what is currently available. Conjugation to a toxic agent is not required for 11BD-2E11-2 to exhibit anti-cancer activity; therefore the specific safety concerns associated with administration of antibody-toxin conjugate are not applicable. Many anti-MCSP antibodies have also been used to generate anti-idiotypic antibodies, which have been tested in both animals and humans. In small non-blinded trials, when the immunization of patients with anti-idiotypic antibodies resulted in a detectable anti-MCSP immune response, there was an increase in median survival of these patients compared to patients who did not develop a specific immune response. In the examples given, targeting MCSP to obtain a positive clinical response may result through the administration of anti-idiotypic antibodies. A problem with this approach is that not all patients who were immunized with the anti-idiotypic antibodies developed an anti-MCSP response. Therefore if an anti-MCSP antibody were available that could result in positive clinical outcomes upon direct administration, this would overcome the problem of relying on a patient's own immune response for producing a clinical benefit. 11BD-2E11-2 is such an antibody as it directly targets MCSP and exhibits anti-cancer effects in pre-clinical xenograft tumor models, which are considered valid predictors of therapeutic efficacy.

In all, this invention teaches the use of the 11BD-2E11-2 antigen as a target for a therapeutic agent, that when administered can reduce the tumor burden (thereby delaying disease progression) of a cancer expressing the antigen in a mammal, and can also lead to a prolonged survival of the treated mammal. This invention also teaches the use of a CDMAB (11BD-2E11-2), and its derivatives, to target its antigen to reduce the tumor burden of a cancer expressing the antigen in a mammal, and to prolong the survival of a mammal bearing tumors that express this antigen. Furthermore, this invention also teaches the use of detecting the 11BD-2E11-2 antigen in cancerous cells that can be useful for the diagnosis, prediction of therapy, and prognosis of mammals bearing tumors that express this antigen.

If a patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibodies conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody-dependent cell-mediated cytotoxicity (ADCC) or complement-dependent cytotoxicity (CDC). For example murine IgM and IgG2a antibodies can activate human complement by binding the C-1 component of the complement system thereby activating the classical pathway of complement activation which can lead to tumor lysis. For human antibodies, the most effective complement-activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody-mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody-mediated cancer cell killing which are more widely accepted. The first is the use of antibodies as a vaccine to induce the body to produce an immune response against the putative antigen that resides on the cancer cell. The second is the use of antibodies to target growth receptors and interfere with their function or to down regulate that receptor so that its function is effectively lost.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end (2003), there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, 39$^{th}$ Annual Meeting, 2003, pages 209-219).

Accordingly, it is an objective of the invention to utilize a method for producing cancerous disease modifying antibodies from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach CDMAB and antigen binding fragments thereof.

It is a further objective of the instant invention to produce CDMAB whose cytotoxicity is mediated through ADCC.

It is yet an additional objective of the instant invention to produce CDMAB whose cytotoxicity is mediated through CDC.

It is still a further objective of the instant invention to produce CDMAB whose cytotoxicity is a function of their ability to catalyze hydrolysis of cellular chemical bonds.

A still further objective of the instant invention is to produce CDMAB which are useful in a binding assay for diagnosis, prognosis, and monitoring of cancer.

Other objects and advantages of this invention will become apparent from the following description wherein, by way of illustration and example, certain embodiments of this invention are set forth.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

EXAMPLE 1

Figure 1:
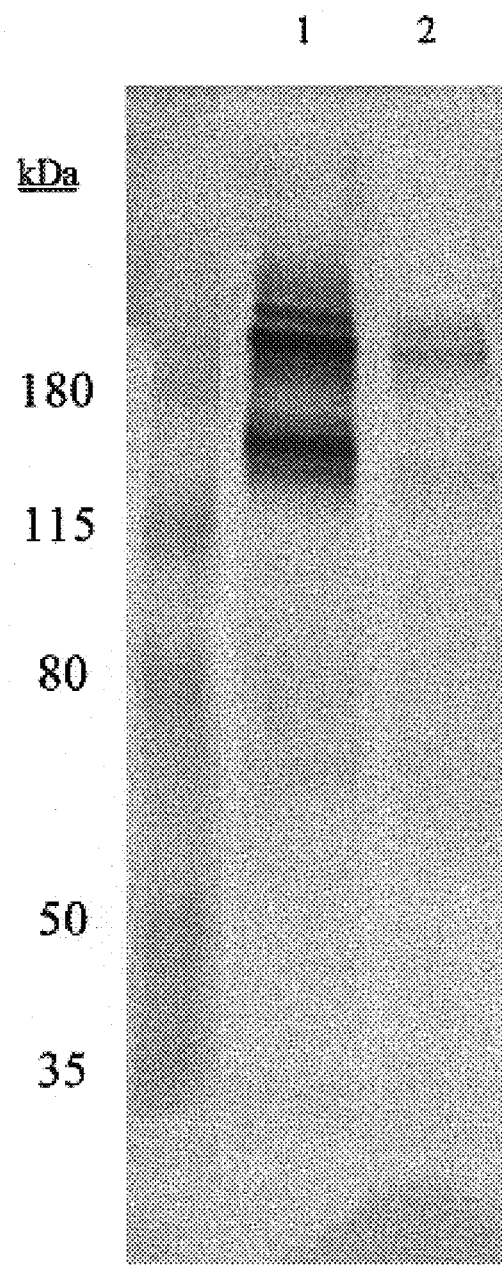
FIG. 1. Western blot of MDA-MB-231 (Lane 1) or OVCAR-3 (Lane 2) membranes probed with 11BD-2E11-2. Membrane proteins were separated under reducing conditions. Molecular weight markers are indicated on the right.

Identification of Binding Proteins by Western Blotting

To identify the antigen(s) recognized by the antibody 11BD-2E11-2, cell membranes expressing this antigen were subjected to gel electrophoresis and transferred using Western blotting to membranes to determine the proteins detected by this antibody (as disclosed in Ser. No. 10/810,744).

1. Membrane Preparation

Previous work demonstrated binding by FACS of 11BD-2E11-2 to the breast cancer line MDA-MB-231 (MB-231). Previous work also demonstrated 11BD-2E11-2 efficacy against the ovarian cancer cell line OVCAR-3. Accordingly, membrane preparations from these 2 cell lines were used for antigen identification. Additional Western blotting and immunoprecipitation studies have also demonstrated a similar binding pattern of 11BD-2E11-2 to A2058 membrane preparations.

Total cell membranes were prepared from confluent cultures of MB-231 breast cancer or OVCAR-3 ovarian cells. Media was removed from cell stacks and the cells were washed with phosphate buffered saline. Cells were dissociated with dissociation buffer (Gibco-BRL, Grand Island, N.Y.) for 20 min at 37° C. on a platform shaker. Cells were collected and centrifuged at 900 g for 10 min at 4° C. After centrifugation, cell pellets were resuspended in PBS and centrifuged again at 900 g for 10 min at 4° C. to wash. Pellets were stored at −80° C. Cell pellets were resuspended in homogenization buffer containing 1 tablet per 50 mL of Complete protease inhibitor cocktail (Roche, Laval QC) at a ratio of 3 mL buffer per gram of cells. The cell suspension was subjected to homogenization using a polytron homogenizer on ice in order to lyse the cells. The cell homogenate was centrifuged at 15,000 g for 10 min at 4° C. to remove the nuclear particulate. Supernatant was harvested, divided into tubes and then centrifuged at 75,600 g for 90 min at 4° C. Supernatant was carefully removed from the tubes and each membrane pellet was resuspended in approximately 5 mL homogenization buffer. The resuspended pellets from all tubes were combined together in one tube and centrifuged at 75,600 g for 90 min at 4° C. Supernatant from the tubes was carefully removed, and the pellets were weighed. Solubilization buffer containing 1 percent Triton X-100 was added to the pellets at a ratio of 3 mL buffer per gram of membrane pellet. Membranes were solubilized by shaking on a platform shaker at 300 rpm for 1 hr on ice. The membrane solution was centrifuged at 75,600 g to pellet insoluble material. The supernatant containing the solubilized membrane proteins was carefully removed from tubes, assayed for protein content, and stored at −80° C.

2. SDS-PAGE and Western Blot

Membrane proteins were separated by SDS-polyacrylamide gel electrophoresis. 20 µg of membrane protein was mixed with SDS-PAGE sample buffer containing 100 mM DTT and was loaded onto a lane of an 8 percent SDS-PAGE gel. A sample of prestained molecular weight markers (Invitrogen, Burlington, ON) was run in a reference lane. Electrophoresis was carried out at 100 V for 10 minutes, followed by 150 V until sufficient resolution of the prestained molecular weight markers was observed. Proteins were transferred from the gel to PVDF membranes (Millipore, Billerica, Mass.) by electroblotting for 16 hr at 40 V. Transfer was assessed by noting complete transfer of the prestained markers from the gel to the membrane. Following transfer, membranes were blocked with 5 percent skim milk powder in Tris-buffered saline containing 0.5 percent Tween-20 (TBST) for 2 hr. Membranes were washed once with TBST and then incubated with 5 µg/mL 11BD-2E11-2 diluted in 3 percent skim milk powder in TBST for 2 hr. After washing 3 times with TBST, membranes were incubated with goat anti-mouse IgG (Fc) conjugated to horseradish peroxidase (HRP) from Jackson Immunologicals (West Grove Pa.). This incubation was followed by washing 3 times with TBST, followed by incubation with the HRP substrate 3,3',5,5'-tetramethyl benzidine (TMB) (substrate kit from Vector Laboratories, Burlington ON).

In FIG. 1, 11BD-2E11-2 clearly binds to 3 molecular weight regions of the separated MB-231 (Lane 1) and OVCAR-3 (Lane 2) membrane proteins. By comparison to the molecular weight (MW) standards, the antibody binds to proteins of MW approximately 150, 240 and 280 kDa. All further studies were done using the MB-231 membranes since stronger reactivity was seen with this cell line.

EXAMPLE 2

Determining Glycosylation of Antigens Bound by 11BD-2E11-2

Figure 2:
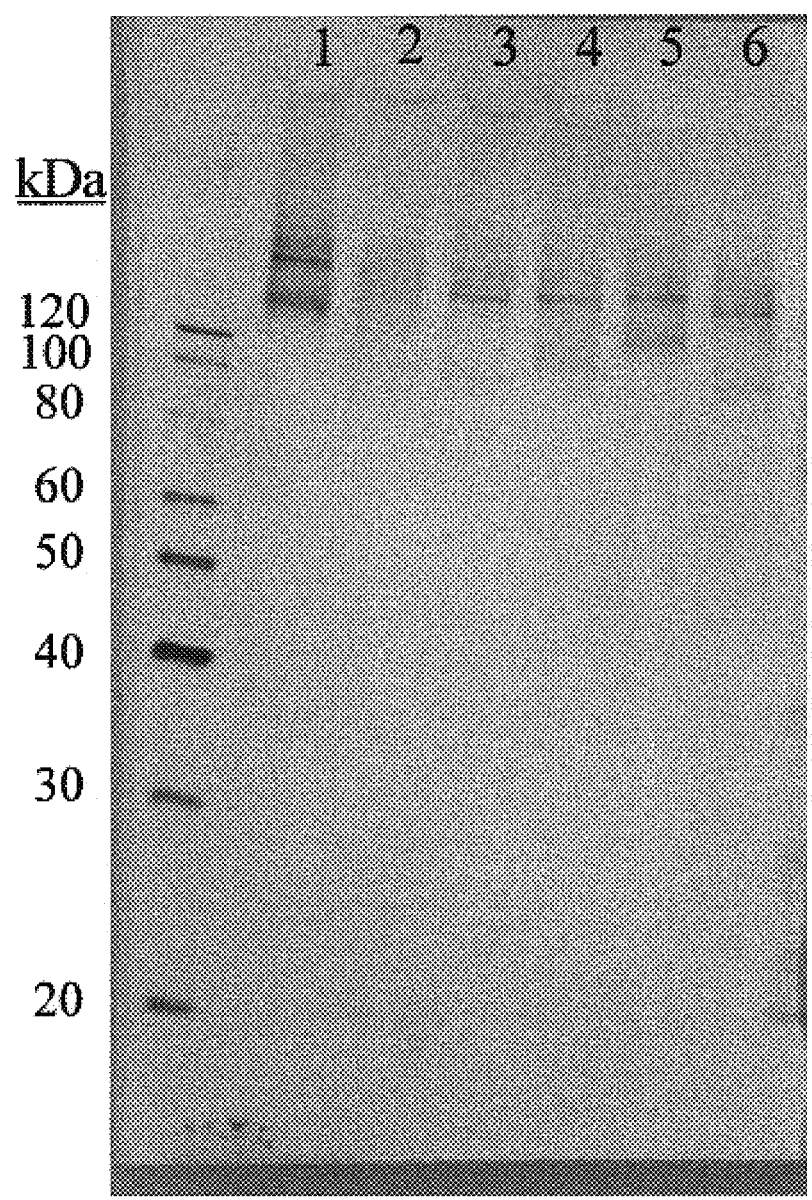
FIG. 2. Effect of deglycosylation on the binding of 11BD-2E11-2 to MDA-MB-231 membranes. 11BD-2E11-2 binding to MDA-MB-231 membranes that were incubated in deglycosylation buffer only (Lane 1), in a combination of PNGase F, endo-o-glycosidase, sialidase, galactosidase and glucosaminodase (Lane 2), in a combination of PNGase, endo-o-glycosidase and sialidase (Lane 3), in sialidase only (Lane 4), in endo-o-glycosidase only (Lane 5), and in PNGase only (Lane 6).

In order to determine if the antigen(s) recognized by the antibody 11BD-2E11-2 were glycoproteins, MB-231 membranes were incubated with different combinations of PNGase F, endo-o-glycosidase, sialidase, galactosidase and glucosaminidase. Membranes were separated by SDS-PAGE followed by Western blotting as described with 11BD-2E11-2. FIG. 2 demonstrates the result of 11BD-2E11-2 binding to MB-231 membranes that were incubated in deglycosylation buffer only (Lane 1), in a combination of PNGase F, endo-o-glycosidase, sialidase, galactosidase and glucosaminodase (Lane 2), in a combination of PNGase, endo-o-glycosidase and sialidase (Lane 3), in sialidase only (Lane 4), in endo-o-glycosidase only (Lane 5), and in PNGase only (Lane 6). Treatment of MB-231 membranes with glycosidases does not eliminate binding of 11BD-2E11-2, however a molecular weight shift of the proteins is observed in all lanes, indicating that the antigen recognized by 11BD-2E11-2 was a glycoprotein.

EXAMPLE 3

Identification of Antigens Bound by 11BD-2E11-2

1. Immunoprecipitation

The identification of the antigen for 11BD-2E11-2 was carried out by isolating the cognate ligand through immunoprecipitation of soublized membrane gylcoproteins with the antibody. 100 µL of Protein G Dynabeads (Dynal Biotech, Lake Success N.Y.) were washed 3 times with 1 mL of 0.1 M sodium phosphate buffer pH 6.0. 100 µg of 11BD-2E11-2 in a total volume of 100 µL 0.1 M sodium phosphate buffer pH 6.0 was added to the washed beads. The mixture was incubated for 1 hr with rotational mixing. Unbound antibody was removed and the 11BD-2E11-2 coated beads were washed 3 times with 0.5 mL 0.1 M sodium phosphate pH 7.4 containing 0.1 percent Tween-20. The 11BD-2E11-2 coated beads were washed 2 times with 1 mL 0.2 M triethanolamine pH 8.2. 11BD-2E11-2 was chemically crosslinked to the beads by adding 1 mL of 0.02 M dimethylpimelimidate in 0.2 M triethanolamine pH 8.2 and incubating with rotational mixing for 30 min. The reaction was stopped by incubating the beads with 1 mL of 0.05 M Tris pH 7.5, for 15 min with rotational mixing. The 11BD-2E11-2 crosslinked beads were washed 3 times with 1 mL of 1 mM $KH_2PO_4$, 10 mM $Na_2HPO_4$, 137 mM NaCl, 2.7 mM KCl (PBS) containing 0.1 percent Tween-20. The 11BD-2E11-2 crosslinked beads were pre-eluted by incubation with 0.1 M citrate pH 3.0 for 3 min followed by 3 washes in 0.1 M PBS containing 0.1 percent Tween-20. A second set of antibody crosslinked beads were prepared in the same manner described using a mouse $IgG_1$ antibody (clone 107.3 from BD Biosciences, Oakville ON) to trinitrophenol, an irrelevant molecule, which was used as a negative $IgG_1$ isotype control.

The 11BD-2E11-2 crosslinked beads were blocked by incubating in 1 percent BSA in 0.1 M sodium phosphate pH 7.4 with rotational mixing for 30 minutes at 4° C. The beads were washed 3 times with 0.1 M sodium phosphate pH 7.4. 500 µg of total membrane preparation from MB-231 cells was incubated with the 11BD-2E11-2 crosslinked beads with rotational mixing for 2.5 hr at 4° C. The immunocomplex bound beads were washed three times with 1 mL of 1 mM $KH_2PO_4$, 10 mM $Na_2HPO_4$, 287 mM NaCl, 2.7 mM KCl containing 1 percent Triton X-100. 11BD-2E11-2 bound protein was eluted from the 11BD-2E11-2 crosslinked beads by incubation with 30 µL of 0.1 M citrate pH 3.0 for 3 min with gentle mixing. The eluted protein was brought to neutral pH by the addition of 9 µL of 1M Tris pH 9. The neutralized eluted protein was stored at −80 ° C. The 11BD-2E11-2 crosslinked beads were washed with 3 mL PBS containing 0.1 percent Tween-20. The $IgG_1$ isotype control (clone 107.3) crosslinked beads were incubated with MB-231 membrane proteins and processed in the same manner as the 11BD-2E11-2 beads.

Two batches of 11BD-2E11-2 immunoprecipitated protein from MB-231 membrane proteins were produced as described and combined together. The same was done for the IgG1 (clone 107.3) isotype control beads. Sixty-two percent of this immunoprecipitate mixture (corresponding to the amount of protein immunoprecipitated from 620 µg of MB-231 membrane proteins) was loaded onto a single lane of a 4-20 percent gradient SDS-PAGE gel. The same amount of material produced from the 107.3 crosslinked beads was loaded in an adjacent lane, as was 20 µg of MB-231 membrane proteins. A sample of unstained molecular weight markers (Invitrogen, Burlington ON) or pre-stained molecular weight markers were run in reference lanes. The sample was separated by electrophoresis at 100 V for 10 min, followed by 150 V for 60 minutes. Proteins were stained by incubating the gel in SYPRO Ruby™ (BioRad, Mississauga, ON). In a parallel Western blot, 18 percent of the immunoprecipitate mixture, which corresponded to the amount of protein immunoprecipitated from 180 µg of MB-231 membrane proteins, and the same amount of material produced from the IgG1 isotype control (clone 107.3) crosslinked beads, were separated by electrophoresis. Proteins were transferred from the gel to PVDF membranes (Millipore, Billerica, Mass.) by electroblotting for 16 hr at 40 V. After transfer, the membrane was blocked with 5 percent skim milk powder in TBST for 2 hr. The membrane was probed with 5 µg/mL 11BD-2E11-2 diluted in 3 percent skim milk powder in TBST for 2 hr. After washing 3 times with TBST, the membrane was incubated with goat anti-mouse IgG (Fc) conjugated HRP for 1 hr. This incubation was followed by washing 3 times with TBST, followed by incubation with the HRP substrate TMB.

Figure 3:
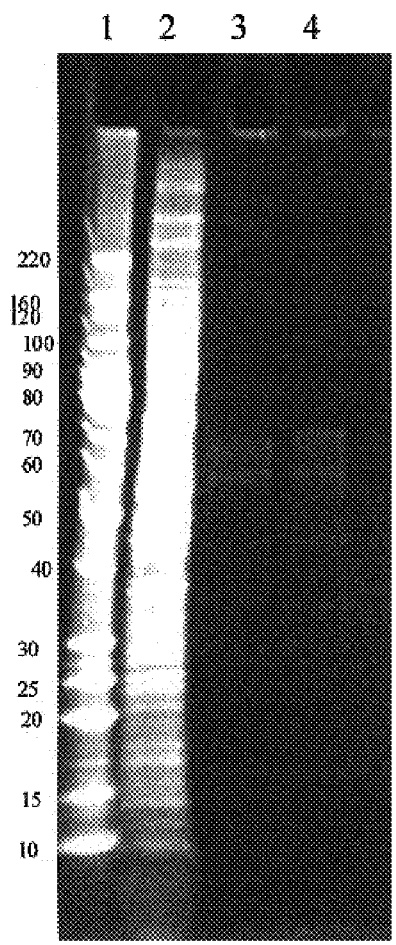
FIG. 3. SDS-PAGE (Panel A) and Western blot (Panel B) of MDA-MB-231 membrane proteins immunoprecipitated with 11BD-2E11-2. Lane 1 represents the molecular weight standard, Lane 2 the MDA-MB-231 membrane proteins, Lane 3 the 11BD-2E11-2 immunoprecipitated material and Lane 4 the isotype control immunoprecipitated material.
Figure 3:
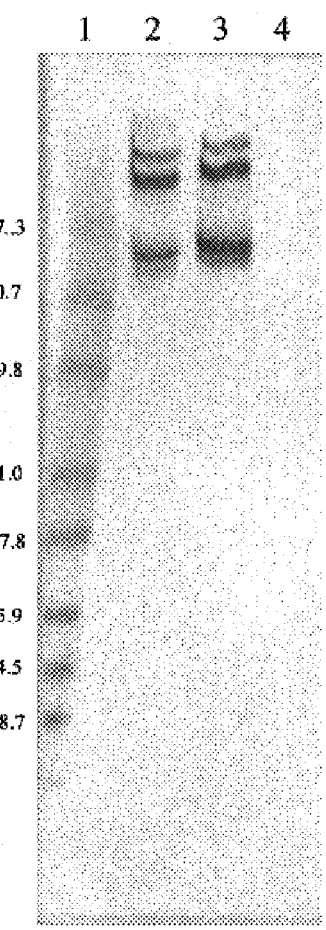

FIG. 3 depicts the gel and Western blot obtained from the proteins immunoprecipitated by 11BD-2E11-2. On the gel (Panel A) Lane 1 represents the molecular weight standard and Lane 2 represents the MB-231 membrane proteins. There were two distinct bands of MW 240 and 280 kDa in the lane containing the 11BD-2E11-2 immunoprecipitated material (Lane 3) that were not present in the lane containing the 107.3 immunoprecipitated material (Lane 4). On the corresponding Western blot (Panel B), 11BD-2E11-2 reacts strongly with the 11BD-2E11-2 immunoprecipitated proteins of MW 240 and 280 kDa (Lane 3). On the Western blot 11BD-2E11-2 also reacts strongly to an additional band in the 11BD-2E11-2 immunoprecipitated protein at 150 kDa; this band was not detectable on the stained gel. The reactivity profile of 11BD-2E11-2 to 11BD-2E11-2 immunoprecipitated protein was similar to that seen in the MB-231 total membranes (Lane 2). There was no reactivity of 11BD-2E11-2 to proteins immunoprecipitated by IgG1 isotype control (clone 107.3; Lane 4), indicating that the binding of 11BD-2E11-2 to the immunoprecipitated protein was specific, and not due to the presence of contaminating proteins.

2. Mass Spectrometry

The regions of the gel corresponding to the 240 and 280 kDa protein immunoprecipitated by 11BD-2E11-2 (FIG. 3, Panel A, Lane 3) were cut out using sterile scalpels. These gel slices were then used for identification of proteins by mass spectrometry using MALDI/MS and LC/MS/MS.

The samples were subjected to proteolytic digestion on a PROGEST workstation using trypsin, and a portion of the resulting digest supernatant was used for MALDI/MS analysis. Spotting was performed robotically (ProMS) with Zip-Tips; peptides were eluted form the C18 material with matrix (α-cyano 4-hydroxy cinnamic acid) prepared in 60 percent acetonitrile, 0.2 percent TFA. MALDI/MS data was acquired on an Voyager DE-STR instrument (Applied Biosystems, Foster City Calif. and the observed m/z values were submitted to ProFound (Proteometrics software package) for peptide mass fingerprint searching. ProFound queried a locally stored copy of the NCBInr database. An additional portion of the digest supernatant was analyzed by nano LC/MS/MS on a Micromass Q-Tof2 using a 75 µm C18 column at a flow-rate of 200 nL/min. MS/MS data were searched using a local copy of MASCOT.

The proteins identified by MALDI/MS and LC/MS/MS are presented in Table 1.

TABLE 1

Proteins Identified by 11BD-2E11-2
Immunoprecipitation of MDA-MB-231 Membranes

| Sample | Observed MW | Method | Protein ID | Percent coverage | # of peptides matched | NCBI accession # |
|---|---|---|---|---|---|---|
| A | 280 kDa | MALDI | Melanoma-associated chondroitin sulfate proteoglycan | 13 | 20 | gi 4503099 |
|  |  | LC/MS/MS | Melanoma chondroitin sulfate proteoglycan |  | 2 | gi 34148711 |
| B | 240 kDa | MALDI | Melanoma associated chondroitin sulfate proteoglycan | 14 | 21 | gi 4503099 |

Both samples were identified as melanoma-associated chondroitin sulfate proteoglycan (MCSP).

3. Confirmation

Figure 4:
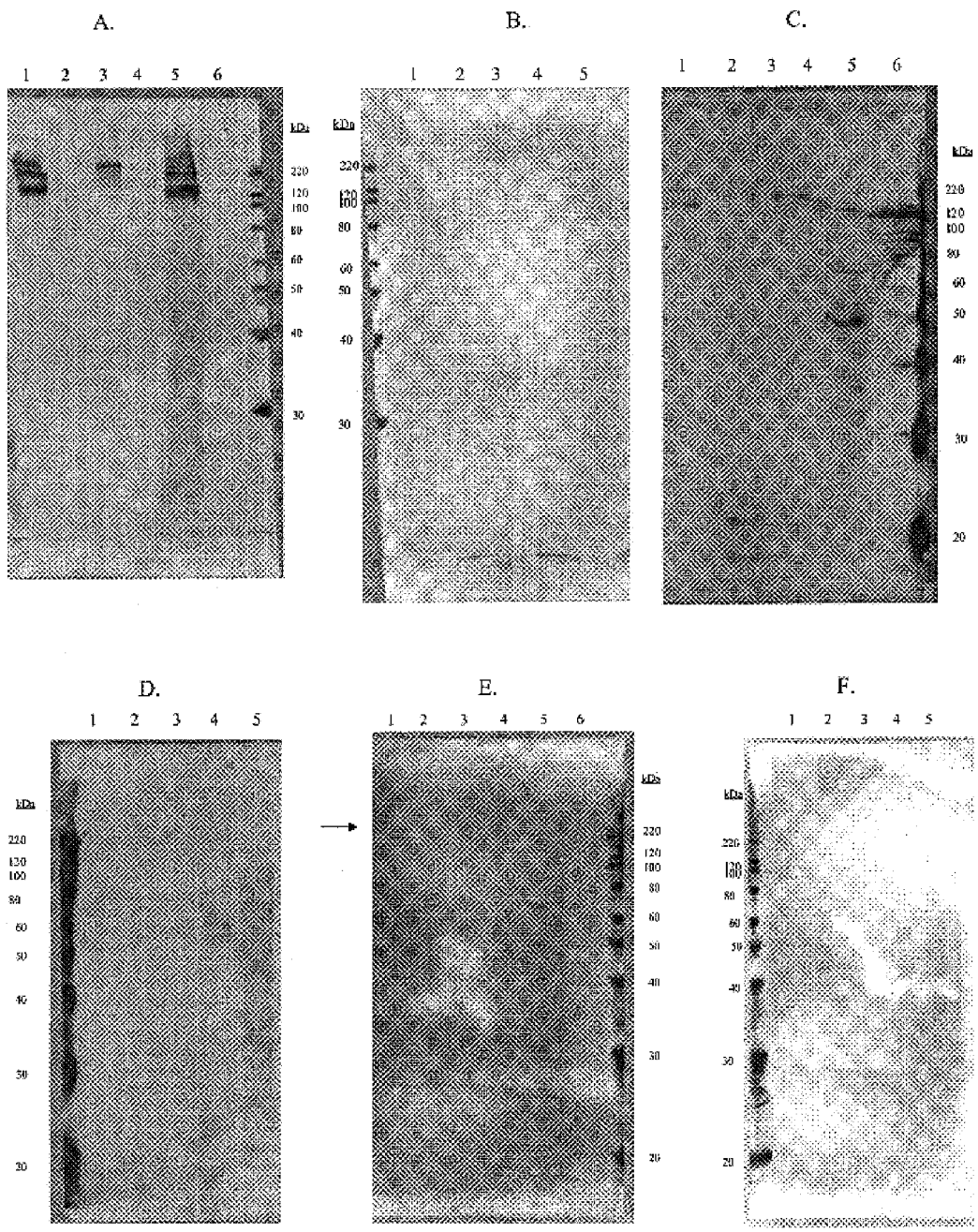
FIG. 4. Western blots of proteins probed with 11BD-2E11-2 (Panel A), IgG1 isotype control (clone 107.3, Panel B), anti-rat NG2 (polyclonal, Panel C), normal rabbit IgG (Panel D), anti-MCSP (clone 9.2.27, Panel E) and IgG2a isotype control (clone G155-228, Panel F). Lane 1: 11BD-2E11-2 immunoprecipitate, Lane 2: IgG1 isotype control (clone 107.3) immunoprecipitate, Lane 3: anti-MCSP (clone 9.2.27) immunoprecipitate, Lane 4: IgG2a isotype control (clone G155-228) immunoprecipitate, Lane 5: MDA-MB-231 membranes and Lane 6: sample buffer only (negative control).

Confirmation of the putative antigen was carried out by determining whether known anti-MCSP antibodies would react with the protein immunoprecipitated by 11BD-2E11-2 and vice versa. Immunoprecipitates were prepared in the same manner as described previously except with the addition of the mouse anti-MCSP monoclonal antibody 9.2.27 (IgG2a) (Chemicon, Temecula Calif.) and the mouse IgG2a antibody (clone G155-178 from BD Biosciences; Oakville ON) to trinitrophenol, an irrelevant molecule, which was used as a negative IgG2a isotype control. 11BD-2E11-2 immunoprecipitate, IgG1 isotype control (clone 107.3) immunoprecipitate, anti-MCSP (clone 9.2.27) immunoprecipitate, IgG2a isotype control (clone G155-228) immunoprecipitate and MB-231 membranes were separated by SDS-PAGE on six replicate 10 percent gels. Electrophoresis and Western blotting were carried out as described above. The membranes were incubated with 5 µg/mL of 11BD-2E11-2, IgG1 isotype control (clone 107.3), anti-MCSP (clone 9.2.27), IgG2a isotype control (clone G155-228), rabbit polyclonal anti-rat NG2 antibody (MCSP is the human homologue of rat NG2; Chemicon, Temecula Calif.) and normal rabbit IgG (Sigma, Saint Louis Mo.) diluted in 3 percent skim milk powder in TBST for 2.5 hr. FIG. 4 demonstrates the results of the Western blotting as described. FIG. 4 (Panel A) shows the binding of 11BD-2E11-2 to 11BD-2E11-2 immunoprecipitate (Lane 1), IgG1 isotype control (clone 107.3) immunoprecipitate (Lane 2), anti-MCSP (clone 9.2.27) immunoprecipitate (Lane 3), IgG2a isotype control (clone G155-228) immunoprecipitate (Lane 4), MB-231 membranes (Lane 5) and sample buffer only (negative control) (Lane 6). 11BD-2E11-2 recognized the same three bands of approximately 150, 240 and 280 kDa in both the MB-231 membranes and in the 11BD-2E11-2 immunoprecipitate. Only the upper 280 kDa band was recognized in the anti-MCSP (clone 9.2.27) immunoprecipitate lane. There is no reaction in either of the isotype control immunoprecipitate lanes, indicating that the reactivity of 11BD-2E11-2 to the immunoprecipitates was due to proteins being specifically bound and immunoprecipitated by both 11BD-2E11-2 and 9.2.27. In a parallel blot (Panel B) probed with IgG1 isotype control (clone 107.3), no reactivity was observed in any of the lanes, indicating that the reactivity observed in the blot probed with 11BD-2E11-2 was specific. Panel C shows the binding of rabbit polyclonal anti-rat NG2 antibody to a parallel blot. Anti-NG2 binds to two bands of approximately 150 and 240 kDa in the 11BD-2E11-2 immunoprecipitate (Lane 1) while it does not bind to proteins of this molecular weight range in any of the other lanes. In a parallel blot (Panel D), normal rabbit IgG shows faint non-specific reactivity to proteins in both the IgG2a immunoprecipitate (Lane 4) and MB-231 membranes (Lane 5). Therefore the same reactivity in these lanes on Panel C (probed with rabbit anti-NG2) should be regarded as non-specific. In a parallel blot (Panel E) anti-MCSP (clone 9.2.27) shows only very faint binding to one band in the anti-MCSP (clone 9.2.27) immunoprecipitate lane (Lane 3, indicated by arrow); this band is not seen in the MB-231 membranes (Lane 5) which indicates that 9.2.27 may have a low affinity for this antigen and only show reactivity when it is present in a concentrated form such as it is in the immunoprecipitated sample. In the final parallel blot (Panel F) probed with IgG2a isotype control (clone G155-228), no reactivity was observed in any of the lanes, indicating that the reactivity observed in the blot probed with anti-MCSP (clone 9.2.27) was specific. These results demonstrate that 11BD-2E11-2 immunoprecipitated protein was recognized by the rat homologue of MCSP, and that anti-MCSP immunoprecipitated protein was recognized by 11BD-2E11-2.

The mass spectroscopic identification combined with the confirmation using known commercial antibodies demonstrates that the antigen for 11BD-2E11-2 is MCSP. This is also consistent with the deglycosylation experiments in Example 2, as the core protein of MCSP is a glycoprotein.

EXAMPLE 4

Antibody Epitope Mapping

Antibody epitope mapping experiments were carried out in order to determine the region(s) of the MCSP molecule that were recognized by 11BD2E11-2. An overlapping peptide array based on the amino acid sequence of MCSP was synthesized and covalently bound to a cellulose membrane in a stepwise manner, resulting in a defined arrangement. Each peptide was 18 amino acids long with an overlap of 9 amino acids. The peptide array was incubated with blocking buffer for several hours. 11BD2E11-2 was conjugated to horseradish peroxidase (HRP) using a modified periodate method following the method of Wilson and Nakane. Following blocking, the peptide array was incubated with 1 µg/mL 11BD2E11-2-HRP in blocking buffer. In a separate experiment, the peptide array was incubated with a sheep anti-mouse IgG-HRP as a negative control. The peptide array was washed with TBST and incubated with a chemiluminescent substrate. The light emitted during the chemiluminescent reaction was quantified for each spot on the peptide array using a charge coupled device (CCD)-camera, resulting in a signal intensity value (Boehringer light units; BLU) for each peptide. For this experiment all signals below 7500 BLU were considered as background. The binding data for the peptide array is listed in Table 2 (SEQ ID NOS: 12-57, respectively, in order of appearance)

TABLE 2

Binding of 11BD-2E11-2-HRP to MCSP Peptide Array

| Peptide Number | Amino Acid Sequence | BLU |
| --- | --- | --- |
| 1 | MQSGRGPPLPAPGLALAL | 566 |
| 2 | PAPGLALALTLTMLARLA | 970 |
| 3 | TLTMLARLASAASFFGEN | 11290 |
| 4 | SAASFFGENHLEVPVATA | 494 |
| 5 | HLEVPVATALTDIDLQLQ | 905 |
| 6 | LTDIDLQLQFSTSQPEAL | 7196 |
| 7 | FSTSQPEALLLLAAGPAD | 937 |
| 8 | LLLAAGPADHLLLQLYSG | 1035 |
| 9 | HLLLQLYSGRLQVRLVLG | 1132 |
| 10 | RLQVRLVLGQEELRLQTP | 3383 |
| 11 | QEELRLQTPAETLLSDSI | 1148 |
| 12 | AETLLSDSIPHTVVLTVV | 788 |
| 13 | PHTVVLTVVEGWATLSVD | 1069 |
| 14 | EGWATLSVDGFLNASSAV | 1637 |
| 15 | GFLNASSAVPGAPLEVPY | 1657 |
| 16 | PGAPLEVPYGLFVGGTGT | 1892 |
| 17 | GLFVGGTGTLGLPYLRGT | 2343 |
| 18 | LGLPYLRGTSRPLRGCLH | 1823 |
| 19 | SRPLRGCLHAATLNGRSL | 2035 |
| 20 | AATLNGRSLLRPLTPDVH | 1672 |
| 21 | LRPLTPDVHEGCAEEFSA | 4678 |
| 22 | EGCAEEFSASDDVALGFS | 5263 |
| 23 | SDDVALGFSGPHSLAAFP | 564 |
| 24 | GPHSLAAFPAWGTQDEGT | 812 |
| 25 | AWGTQDEGTLEFTLTTQS | 1943 |
| 26 | LEFTLTTQSRQAPLAFQA | 33781 |
| 27 | RQAPLAFQAGGRRGDFIY | 3904 |

TABLE 2-continued

Binding of 11BD-2E11-2-HRP to MCSP Peptide Array

| Peptide Number | Amino Acid Sequence | BLU |
|---|---|---|
| 28 | GGRRGDFIYVDIFEGHLR | 3199 |
| 29 | VDIFEGHLRAVVEKGQGT | 2016 |
| 30 | AVVEKGQGTVLLHNSVPV | 1399 |
| 31 | VLLHNSVPVADGQPHEVS | 1114 |
| 32 | ADGQPHEVSVHINAHRLE | 1268 |
| 33 | VHINAHRLEISVDQYPTH | 1665 |
| 34 | ISVDQYPTHTSNRGVLSY | 1562 |
| 35 | TSNRGVLSYLEPRGSLLL | 2539 |
| 36 | LEPRGSLLLGGLDAEASR | 2576 |
| 37 | GGLDAEASRHLQEHRLGL | 1376 |
| 38 | HLQEHRLGLTPEATNASL | 957 |
| 39 | TPEATNASLLGCMEDLSV | 4354 |
| 40 | LGCMEDLSVNGQRRGLRE | 5881 |
| 41 | NGQRRGLREALLTRNMAA | 3880 |
| 42 | ALLTRNMAAGCRLEEEEY | 3939 |
| 43 | GCRLEEEEYEDDAYGHYE | 731 |
| 44 | EDDAYGHYEAFSTLAPEA | 1013 |
| 45 | AFSTLAPEAWPAMELPEP | 844 |
| 46 | WPAMELPEPCVPEPGLPP | 2033 |
| 47 | CVPEPGLPPVFANFTQLL | 7330 |
| 48 | VFANFTQLLTISPLVVAE | 2261 |
| 49 | TISPLVVAEGGTAWLEWR | 2439 |
| 50 | GGTAWLEWRHVQPTLDLM | 1956 |
| 51 | HVQPTLDLMEAELRKSQV | 2044 |
| 52 | EAELRKSQVLFSVTRGAH | 2944 |
| 53 | LFSVTRGAHYGELELDIL | 4346 |
| 54 | YGELELDILGAQARKMFT | 3249 |
| 55 | GAQARKMFTLLDVVNRKA | 4077 |
| 56 | LLDVVNRKARFIHDGSED | 3778 |
| 57 | RFIHDGSEDTSDQLVLEV | 1287 |
| 58 | TSDQLVLEVSVTARVPMP | 2650 |
| 59 | SVTARVPMPSCLRRGQTY | 1327 |
| 60 | SCLRRGQTYLLPIQVNPV | 1342 |
| 61 | LLPIQVNPVNDPPHIIFP | 25 |
| 62 | NDPPHIIFPHGSLMVILE | 6 |
| 63 | HGSLMVILEHTQKPLGPE | 564 |
| 64 | HTQKPLGPEVFQAYDPDS | 781 |
| 65 | VFQAYDPDSACEGLTFQV | 3015 |
| 66 | ACEGLTFQVLGTSSGLPV | 15941 |
| 67 | LGTSSGLPVERRDQPGEP | 2310 |
| 68 | ERRDQPGEPATEFSCREL | 7895 |
| 69 | ATEFSCRELEAGSLVYVH | 2724 |
| 70 | EAGSLVYVHCGGPAQDLT | 4799 |
| 71 | CGGPAQDLTFRVSDGLQA | 56703 |
| 72 | FRVSDGLQASPPATLKVV | 6138 |
| 73 | SPPATLKVVAIRPAIQIH | 2873 |
| 74 | AIRPAIQIHRSTGLRLAQ | 4406 |
| 75 | RSTGLRLAQGSAMPILPA | 4387 |
| 76 | GSAMPILPANLSVETNAV | 2024 |
| 77 | NLSVETNAVGQDVSVLFR | 2333 |
| 78 | GQDVSVLFRVTGALQFGE | 4056 |
| 79 | VTGALQFGELQKHSTGGV | 1554 |
| 80 | LQKHSTGGVEGAEWWATQ | 962 |
| 81 | EGAEWWATQAFHQRDVEQ | 290 |
| 82 | AFHQRDVEQGRVRYLSTD | 1059 |
| 83 | GRVRYLSTDPQHHAYDTV | 842 |
| 84 | PQHHAYDTVENLALEVQV | 1173 |
| 85 | ENLALEVQVGQEILSNLS | 3084 |
| 86 | GQEILSNLSFPVTIQRAT | 4928 |
| 87 | FPVTIQRATVWMLRLEPL | 2142 |
| 88 | VWMLRLEPLHTQNTQQET | 2345 |
| 89 | HTQNTQQETLTTAHLEAT | 2719 |
| 90 | LTTAHLEATLEEAGPSPP | 2513 |
| 91 | LEEAGPSPPTFHYEVVQA | 2380 |
| 92 | TFHYEVVQAPRKGNLQLQ | 4209 |
| 93 | PRKGNLQLQGTRLSDGQG | 8990 |
| 94 | GTRLSDGQGFTQDDIQAG | 3830 |
| 95 | FTQDDIQAGRVTYGATAR | 4641 |
| 96 | RVTYGATARASEAVEDTF | 1950 |
| 97 | ASEAVEDTFRFRVTAPPY | 1463 |
| 98 | RFRVTAPPYFSPLYTFPI | 870 |
| 99 | FSPLYTFPIHIGGDPDAP | 1092 |
| 100 | HIGGDPDAPVLTNVLLVV | 1043 |
| 101 | VLTNVLLVVPEGGEGVLS | 169 |

TABLE 2-continued

Binding of 11BD-2E11-2-HRP to MCSP Peptide Array

| Peptide Number | Amino Acid Sequence | BLU |
| --- | --- | --- |
| 102 | PEGGEGVLSADHLFVKSL | 640 |
| 103 | ADHLFVKSLNSASYLYEV | 601 |
| 104 | NSASYLYEVMERPRLGRL | 2697 |
| 105 | MERPRLGRLAWRGTQDKT | 5728 |
| 106 | AWRGTQDKTTMVTSFTNE | 2771 |
| 107 | TMVTSFTNEDLLRGRLVY | 2243 |
| 108 | DLLRGRLVYQHDDSETTE | 2316 |
| 109 | QHDDSETTEDDIPFVATR | 3020 |
| 110 | DDIPFVATRQGESSGDMA | 3695 |
| 111 | QGESSGDMAWEEVRGVFR | 3949 |
| 112 | WEEVRGVFRVAIQPVNDH | 2674 |
| 113 | VAIQPVNDHAPVQTISRI | 4340 |
| 114 | APVQTISRIFHVARGGRR | 6454 |
| 115 | FHVARGGRRLLTTDDVAF | 5898 |
| 116 | LLTTDDVAFSDADSGFAD | 1615 |
| 117 | SDADSGFADAQLVLTRKD | 1464 |
| 118 | AQLVLTRKDLLFGSIVAV | 1137 |
| 119 | LLFGSIVAVDEPTRPIYR | 1972 |
| 120 | DEPTRPIYRFTQEDLRKR | 5531 |
| 121 | FTQEDLRKRRVLFVHSGA | 1860 |
| 122 | RVLFVHSGADRGWIQLQV | 465 |
| 123 | DRGWIQLQVSDGQHQATA | 812 |
| 124 | SDGQHQATALLEVQASEP | 759 |
| 125 | LLEVQASEPYLRVANGSS | 1502 |
| 126 | YLRVANGSSLVVPQGGQG | 4406 |
| 127 | LVVPQGGQGTIDTAVLHL | 1506 |
| 128 | TIDTAVLHLDTNLDIRSG | 2535 |
| 129 | DTNLDIRSGDEVHYHVTA | 2159 |
| 130 | DEVHYHVTAGPRWGQLVR | 4541 |
| 131 | GPRWGQLVRAGQPATAFS | 9113 |
| 132 | AGQPATAFSQQDLLDGAV | 3668 |
| 133 | QQDLLDGAVLYSHNGSLS | 3565 |
| 134 | LYSHNGSLSPEDTMAFSV | 3626 |
| 135 | PEDTMAFSVEAGPVHTDA | 2159 |
| 136 | EAGPVHTDATLQVTIALE | 1585 |
| 137 | TLQVTIALEGPLAPLKLV | 2444 |
| 138 | GPLAPLKLVRHKKIYVFQ | 1100 |
| 139 | RHKKIYVFQGEAAEIRRD | 2108 |
| 140 | GEAAEIRRDQLEAAQEAV | 1275 |
| 141 | QLEAAQEAVPPADIVFSV | 902 |
| 142 | PPADIVFSVKSPPSAGYL | 1224 |
| 143 | KSPPSAGYLVMVSRGALA | 1725 |
| 144 | VMVSRGALADEPPSLDPV | 949 |
| 145 | DEPPSLDPVQSFSQEAVD | 1189 |
| 146 | QSFSQEAVDTGRVLYLHS | 1447 |
| 147 | TGRVLYLHSRPEAWSDAF | 1661 |
| 148 | RPEAWSDAFSLDVASGLG | 2269 |
| 149 | SLDVASGLGAPLEGVLVE | 2123 |
| 150 | APLEGVLVELEVLPAAIP | 5144 |
| 151 | LEVLPAAIPLEAQNFSVP | 3152 |
| 152 | LEAQNFSVPEGGSLTLAP | 3277 |
| 153 | EGGSLTLAPPLLRVSGPY | 4455 |
| 154 | PLLRVSGPYFPTLLGLSL | 4311 |
| 155 | FPTLLGLSLQVLEPPQHG | 3545 |
| 156 | QVLEPPQHGPLQKEDGPQ | 1883 |
| 157 | PLQKEDGPQARTLSAFSW | 3132 |
| 158 | ARTLSAFSWRMVEEQLIR | 3149 |
| 159 | RMVEEQLIRYVHDGSETL | 947 |
| 160 | YVHDGSETLTDSFVLMAN | 1332 |
| 161 | TDSFVLMANASEMDRQSH | 320 |
| 162 | ASEMDRQSHPVAFTVTVL | 521 |
| 163 | PVAFTVTVLPVNDQPPIL | 884 |
| 164 | PVNDQPPILTTNTGLQMW | 867 |
| 165 | TTNTGLQMWEGATAPIPA | 1235 |
| 166 | EGATAPIPAEALRSTDGD | 1323 |
| 167 | EALRSTDGDSGSEDLVYT | 1970 |
| 168 | SGSEDLVYTIEQPSNGRV | 1972 |
| 169 | IEQPSNGRVVLRGAPGTE | 2836 |
| 170 | VLRGAPGTEVRSFTQAQL | 11671 |
| 171 | VRSFTQAQLDGGLVLFSH | 2167 |
| 172 | DGGLVLFSHRGTLDGGFP | 2307 |
| 173 | RGTLDGGFPFRLSDGEHT | 2979 |
| 174 | FRLSDGEHTSPGHFFRVT | 3900 |
| 175 | SPGHFFRVTAQKQVLLSL | 4176 |

TABLE 2-continued

Binding of 11BD-2E11-2-HRP to MCSP Peptide Array

| Peptide Number | Amino Acid Sequence | BLU |
|---|---|---|
| 176 | AQKQVLLSLKGSQTLTVC | 3627 |
| 177 | KGSQTLTVCPGSVQPLSS | 6489 |
| 178 | PGSVQPLSSQTLRASSSA | 3448 |
| 179 | QTLRASSSAGTDPQLLLY | 1159 |
| 180 | GTDPQLLLYRVVRGPQLG | 1266 |
| 181 | RVVRGPQLGRLFHAQQDS | 3735 |
| 182 | RLFHAQQDSTGEALVNFT | 1155 |
| 183 | TGEALVNFTQAEVYAGNI | 1544 |
| 184 | QAEVYAGNILYEHEMPPE | 889 |
| 185 | LYEHEMPPEPFWEAHDTL | 826 |
| 186 | PFWEAHDTLELQLSSPPA | 1748 |
| 187 | ELQLSSPPARDVAATLAV | 1713 |
| 188 | RDVAATLAVAVSFEAACP | 1953 |
| 189 | AVSFEAACPQRPSHLWKN | 2533 |
| 190 | QRPSHLWKNKGLWVPEGQ | 5178 |
| 191 | KGLWVPEGQRARITVAAL | 3891 |
| 192 | RARITVAALDASNLLASV | 5276 |
| 193 | DASNLLASVPSPQRSEHD | 2460 |
| 194 | PSPQRSEHDVLFQVTQFP | 2205 |
| 195 | VLFQVTQFPSRGQLLVSE | 2556 |
| 196 | SRGQLLVSEEPLHAGQPH | 1359 |
| 197 | EPLHAGQPHFLQSQLAAG | 1265 |
| 198 | FLQSQLAAGQLVYAHGGG | 1361 |
| 199 | QLVYAHGGGTQQDGFHF | 1210 |
| 200 | GTQQDGFHFRAHLQGPAG | 3436 |
| 201 | RAHLQGPAGASVAGPQTS | 3587 |
| 202 | ASVAGPQTSEAFAITVRD | 980 |
| 203 | EAFAITVRDVNERPPQPQ | 1032 |
| 204 | VNERPPQPQASVPLRLTR | 4790 |
| 205 | ASVPLRLTRGSRAPISRA | 4393 |
| 206 | GSRAPISRAQLSVVDPDS | 2547 |
| 207 | QLSVVDPDSAPGEIEYEV | 1318 |
| 208 | APGEIEYEVQRAPHNGFL | 1561 |
| 209 | QRAPHNGFLSLVGGGLGP | 4879 |
| 210 | SLVGGGLGPVTRFTQADV | 3371 |
| 211 | VTRFTQADVDSGRLAFVA | 2747 |
| 212 | DSGRLAFVANGSSVAGIF | 5532 |
| 213 | NGSSVAGIFQLSMSDGAS | 3503 |
| 214 | QLSMSDGASPPLPMSLAV | 2245 |
| 215 | PPLPMSLAVDILPSAIEV | 1845 |
| 216 | DILPSAIEVQLRAPLEVP | 1504 |
| 217 | QLRAPLEVPQALGRSSLS | 5177 |
| 218 | QALGRSSLSQQQLRVVSD | 3060 |
| 219 | QQQLRVVSDREEPEAAYR | 988 |
| 220 | REEPEAAYRLIQGPQYGH | 762 |
| 221 | LIQGPQYGHLLVGGRPTS | 1334 |
| 222 | LLVGGRPTSAFSQFQIDQ | 2308 |
| 223 | AFSQFQIDQGEVVFAFTN | 2915 |
| 224 | GEVVFAFTNFSSSHDHFR | 3745 |
| 225 | FSSSHDHFRVLALARGVN | 2196 |
| 226 | VLALARGVNASAVVNVTV | 1991 |
| 227 | ASAVVNVTVRALLHVWAG | 1402 |
| 228 | RALLHVWAGGPWFQGATL | 1790 |
| 229 | GPWPQGATLRLDPTVLDA | 1447 |
| 230 | RLDPTVLDAGELANRTGS | 1796 |
| 231 | GELANRTGSVPRFRLLEG | 7317 |
| 232 | VPRFRLLEGPRHGRVVRV | 3761 |
| 233 | PRHGRVVRVPRARTEPGG | 8844 |
| 234 | PRARTEPGGSQLVEQFTQ | 3609 |
| 235 | SQLVEQFTQQDLEDGRLG | 1985 |
| 236 | QDLEDGRLGLEVGRPEGR | 1551 |
| 237 | LEVGRPEGRAPGPAGDSL | 1136 |
| 238 | APGPAGDSLTLELWAQGV | 993 |
| 239 | TLELWAQGVPPAVASLDF | 844 |
| 240 | PPAVASLDFATEPYNAAR | 1339 |
| 241 | ATEPYNAARPYSVALLSV | 786 |
| 242 | PYSVALLSVPEAARTEAG | 1723 |
| 243 | PEAARTEAGKPESSTPTG | 1417 |
| 244 | KPESSTPTGEPGPMASSP | 1449 |
| 245 | EPGPMASSPEPAVAKGGF | 1739 |
| 246 | EPAVAKGGFLSFLEANMF | 4457 |
| 247 | LSFLEANMFSVIIPMCLV | 1275 |
| 248 | SVIIPMCLVLLLLALILP | 1306 |
| 249 | LLLLALILPLLFYLRKRN | 1291 |

TABLE 2-continued

Binding of 11BD-2E11-2-HRP to MCSP Peptide Array

| Peptide Number | Amino Acid Sequence | BLU |
|---|---|---|
| 250 | LLFYLRKRNKTGKHDVQV | 1820 |
| 251 | KTGKHDVQVLTAKPRNGL | 13573 |
| 252 | LTAKPRNGLAGDTETFRK | 10322 |
| 253 | AGDTETFRKVEPGQAIPL | 4744 |
| 254 | VEPGQAIPLTAVPGQGPP | 3571 |
| 255 | TAVPGQGPPPGGQPDPEL | 1733 |
| 256 | PGGQPDPELLQFCRTPNP | 11325 |
| 257 | LQFCRTPNPALKNGQYWV | 1550 |

Figure 5:
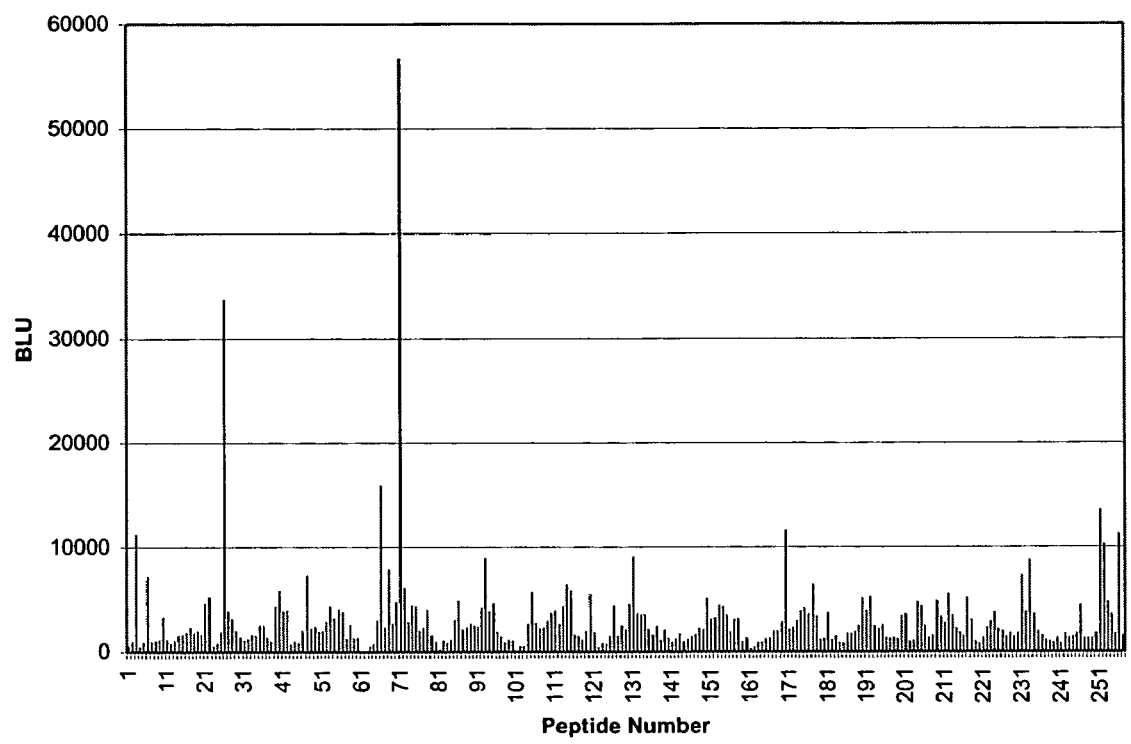
FIG. 5. Intensity of binding (Boehringer light units) of 11BD-2E11-2-HRP to MCSP peptide array.

FIG. 5 represents a graphical image of the binding data. 11BD-2E11-2 bound most strongly to peptides #26, SEQ ID NO. 1 and #71, SEQ ID NO. 2. Weaker binding, which was greater than background, was recognizable on peptides #3, SEQ ID NO. 3, #66, SEQ ID NO. 4, #170, SEQ ID NO. 5, #251, SEQ ID NO. 6, #252, SEQ ID NO. 7 and #256, SEQ ID NO. 8. These results indicated that 11BD2E11-2 may bind to a discontinuous epitope with two major binding sites (peptides #26 and #71) as well as to a number of other sites.

EXAMPLE 5

As outlined in Ser. No. 10/743,451, the hybridoma cell line 11BD-2E11-2 was deposited, in accordance with the Budapest Treaty, with the American Type Culture Collection, 10801 University Blvd., Manassas, Va. 20110-2209 on Nov. 11, 2003, under Accession Number PTA-5643. In accordance with CFR 1.808, the depositors assure that all restrictions imposed on the availability to the public of the deposited materials will be irrevocably removed upon the granting of a patent.

Antibody Production:

11BD-2E11-2 monoclonal antibody was produced by culturing the hybridoma (PTA-5643) in CL-1000 flasks (BD Biosciences, Oakville, ON) with collections and reseeding occurring twice/week. The antibody was purified according to standard antibody purification procedures with Protein G Sepharose 4 Fast Flow (Amersham Biosciences, Baie d'Urfé, QC).

As previously described in Ser. No. 10/348,231, 11BD-2E11-2 was compared to a number of both positive (anti-Fas (EOS9.1, IgM, kappa, 20 micrograms/mL, eBioscience, San Diego, Calif.), anti-Her2/neu (IgG1, kappa, 10 microgram/mL, Inter Medico, Markham, ON), anti-EGFR (C225, IgG1, kappa, 5 microgram/mL, Cedarlane, Hornby, ON), Cycloheximide (100 micromolar, Sigma, Oakville, ON), NaN3 (0.1%, Sigma, Oakville, ON)) and negative (107.3 (anti-TNP, IgG1, kappa, 20 microgram/mL, BD Biosciences, Oakville, ON), G155-178 (anti-TNP, IgG2a, kappa, 20 microgram/mL, BD Biosciences, Oakville, ON), MPC-11 (antigenic specificity unknown, IgG2b, kappa, 20 microgram/mL), J606 (anti-fructosan, IgG3, kappa, 20 microgram/mL), IgG Buffer (2%)) controls in a cytotoxicity assay (Table 2). Breast cancer (MDA-MB-231 (MB-231), MDA-MB-468 (MB-468), MCF-7), colon cancer (HT-29, SW1116, 5W620), lung cancer (NCI H460), ovarian cancer (OVCAR-3 (OVCAR)), prostate cancer (PC-3), and non-cancer (CCD 27sk, Hs888 Lu) cell lines were tested (all from the ATCC, Manassas, Va.). The Live/Dead cytotoxicity assay was obtained from Molecular Probes (Eugene, OR). The assays were performed according to the manufacturer's instructions with the changes outlined below. Cells were plated before the assay at the predetermined appropriate density. After 2 days, purified antibody or controls were diluted into media, and then 100 microliters were transferred to the cell plates and incubated in a 5 percent $CO_2$ incubator for 5 days. The plate was then emptied by inverting and blotted dry. Room temperature DPBS containing $MgCl_{12}$ and $CaCl_2$ was dispensed into each well from a multi-channel squeeze bottle, tapped three times, emptied by inversion and then blotted dry. 50 microliters of the fluorescent calcein dye diluted in DPBS containing $MgCl_2$ and $CaCl_2$ was added to each well and incubated at 37° C. in a 5 percent $CO_2$ incubator for 30 minutes. The plates were read in a Perkin-Elmer HTS7000 fluorescence plate reader and the data was analyzed in Microsoft Excel and the results were tabulated in Table 3. The data represented an average of four experiments tested in triplicate and presented qualitatively in the following fashion: 4/4 experiments greater than threshold cytotoxicity (+++), 3/4 experiments greater than threshold cytotoxicity (++), 2/4 experiments greater than threshold cytotoxicity (+). Unmarked cells in Table 3 represent inconsistent or effects less than the threshold cytotoxicity. 11 BD-2E11-2 was specifically cytotoxic in breast and ovarian cancer cells, and did not affect normal cells. The chemical cytotoxic agents induced their expected cytotoxicity while a number of other antibodies which were included for comparison also performed as expected given the limitations of biological cell assays. In toto, it was shown that the 11BD-2E11-2 antibody has cytotoxic activity against two cancer cell types. The antibody was selective in its activity since not all cancer cell types were susceptible. Furthermore, the antibody demonstrated functional specificity since it did not produce cytotoxicity against non-cancer cell types, which is an important factor in a therapeutic situation.

TABLE 3

| | BREAST | | | COLON | | | LUNG | OVARY | PROSTATE | NORMAL | |
|---|---|---|---|---|---|---|---|---|---|---|---|
| | MB-231 | MB-468 | MCF-7 | HT-29 | SW1116 | SW620 | NCI H460 | OVCAR | PC-3 | CCD 27sk | Hs888 Lu |
| 11BD-2E11-2 | — | — | + | — | — | — | — | + | — | — | — |
| anti-Fas | — | — | +++ | — | — | — | — | +++ | + | — | + |
| anti-Her2 | + | — | + | — | — | — | — | + | — | — | — |
| anti-EGFR | — | +++ | + | — | +++ | — | — | + | — | + | — |
| CHX (100 µM) | +++ | +++ | +++ | +++ | +++ | +++ | +++ | +++ | +++ | +++ | +++ |
| NaN₃(0.1%) | +++ | +++ | +++ | +++ | — | — | +++ | +++ | +++ | — | — |
| IgG1 | | | | | | | +++ | | + | | |

TABLE 3-continued

| | BREAST | | | COLON | | | LUNG | OVARY | PROSTATE | NORMAL | |
|---|---|---|---|---|---|---|---|---|---|---|---|
| | MB-231 | MB-468 | MCF-7 | HT-29 | SW1116 | SW620 | NCI H460 | OVCAR | PC-3 | CCD 27sk | Hs888 Lu |
| IgG2a | | | +++ | | + | | | | | | |
| IgG2b | | | +++ | | | | | | | | |
| IgG3 | | | | | | | | | | | |
| IgG Buffer | + | | | | | | | | | | |

As previously described in Ser. Nos. 10/348,231 and 10/810,744, binding of 11BD-2E11-2 to the above-mentioned panel of cancer and normal cell lines plus the following additional ovarian cancer cell lines (A2780-cp, A2780-s, C-14, OV2008, Hey, OCC-1, OVCA-429 and ES-2+SEAP) was assessed by flow cytometry (FACS). Cells were prepared for FACS by initially washing the cell monolayer with DPBS (without $Ca^{++}$ and $Mg^{++}$). Cell dissociation buffer (INVIT-ROGEN, Burlington, ON) was then used to dislodge the cells from their cell culture plates at 37° C. After centrifugation and collection the cells were resuspended in Dulbecco's phosphate buffered saline containing $MgCl_2$, $CaCl_2$ and 2 or 25 percent fetal bovine serum (FBS) at 4° C. (wash media) and counted, aliquoted to appropriate cell density, spun down to pellet the cells and resuspended in staining media (DPBS containing $MgCl_2$ and $CaCl_2$+/−2 percent FBS) containing 11BD-2E11-2 or control antibodies (isotype control or anti-EGFR) at 20 μg/mL on ice for 30 min. Prior to the addition of Alexa Fluor 488-conjugated secondary antibody the cells were washed once with wash media. The Alexa Fluor 488-conjugated antibody in staining media was then added for 20 to 30 min. The cells were then washed for the final time and resuspended in staining media containing 1 μg/mL propidium iodide or 1.5 percent paraformaldehyde. Flow cytometric acquisition of the cells was assessed by running samples on a FACScan using the CellQuest software (BD Biosciences, Oakville, ON). The forward (FSC) and side scatter (SSC) of the cells were set by adjusting the voltage and amplitude gains on the FSC and SSC detectors. The detectors for the three fluorescence channels (FL1, FL2, and FL3) were adjusted by running cells stained with purified isotype control antibody followed by Alexa Fluor 488-conjugated secondary antibody such that cells had a uniform peak with a median fluorescent intensity of approximately 1-5 units. Live cells were acquired by gating for FSC and propidium iodide exclusion (when used). For each sample, approximately 10,000 live cells were acquired for analysis and the resulted are presented in Tables 4 and 5. Tables 4 and 5 tabulated the mean fluorescence intensity fold increase above isotype control and is presented qualitatively as: less than 5 (−); 5 to 50 (+); 50 to 100 (++); above 100 (+++) and in parenthesis, the percentage of cells stained.

TABLE 4

| | | BREAST | | | COLON | | | LUNG | OVARY | PROSTATE | NORMAL | | |
|---|---|---|---|---|---|---|---|---|---|---|---|---|---|
| Antibody | Isotype | MB-231 | MB-468 | MCF-7 | HT-29 | SW 1116 | SW 620 | NCI H460 | OVCAR | PC-3 | CCD 27sk | CCD-112 | Hs 888 Lu |
| 11BD-2E11-2 | IgG1, k | + | − | − | − | − | − | − | − | − | + | + | + |
| anti-EGFR | IgG1, k | ++ | ++ | − | + | + | − | + | + | + | + | + | + |

TABLE 5

| | | Ovarian | | | | | | | |
|---|---|---|---|---|---|---|---|---|---|
| Antibody | Isotype | A2780-cp | A2780-s | C-14 | OV2008 | ES-2 + SEAP | Hey | OCC-1 | OVCA-429 |
| 11BD-2E11-2 | IgG1, k | + | + | − | − | + | + | + | − |
| anti-EGFR | IgG1, k | − | − | + | + | + | + | + | + |

Figure 6:
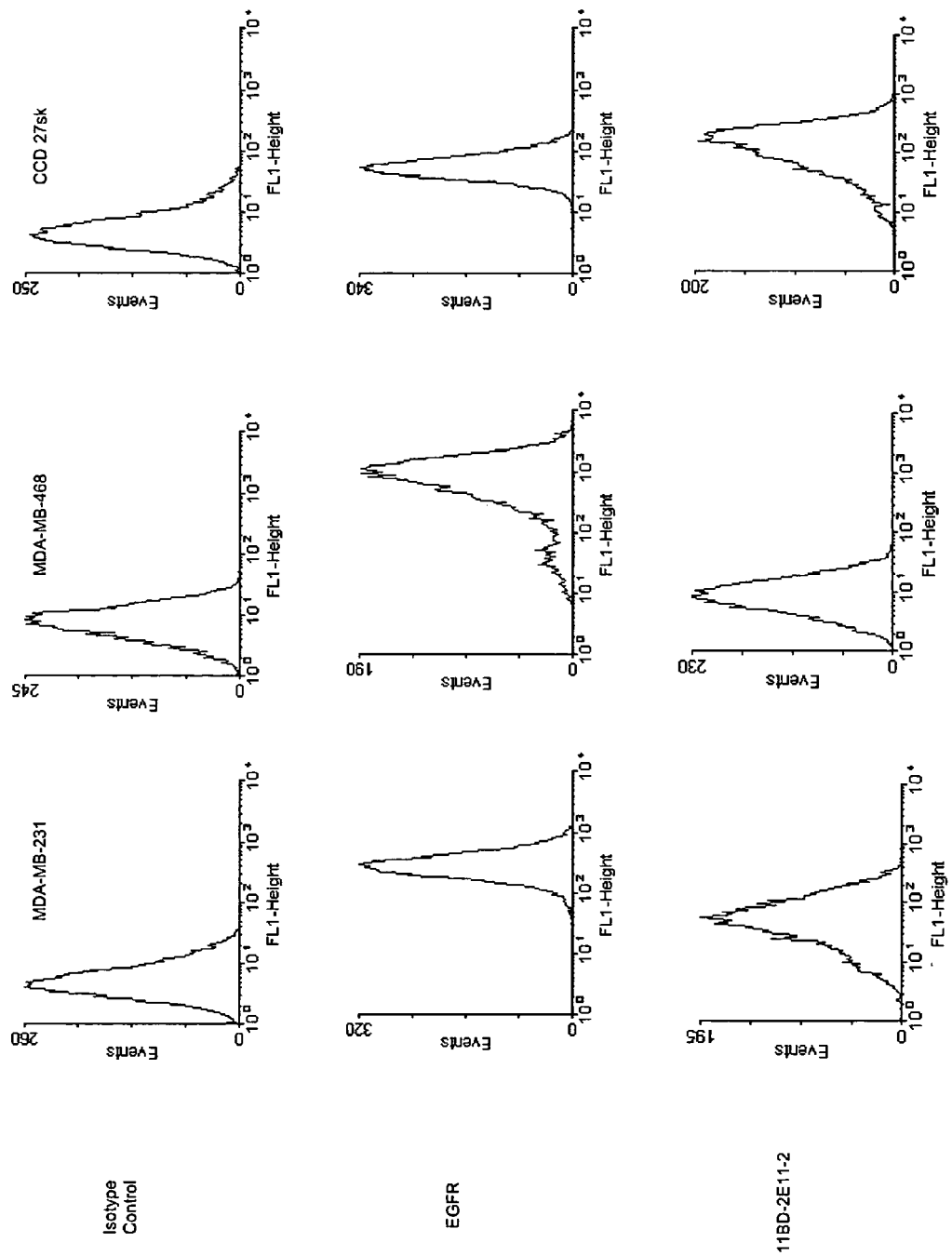
FIG. 6. Representative FACS histograms of 11BD-2E11-2, isotype control or anti-EGFR directed against several cancer cell lines and non-cancer cells.

Representative histograms of 11BD-2E11-2 antibodies were compiled for FIG. 6. 11BD-2E11-2 displayed specific tumor binding to the breast tumor cell line MDA-MB-231 (Table 4) and several ovarian tumor cell lines including ES-2+SEAP (Table 5). There was also binding of 11BD-2E11-2 to non-cancer cells, however that binding did not produce cytotoxicity. This was further evidence that binding was not necessarily predictive of the outcome of antibody ligation of its cognate antigen, and was a non-obvious finding. This suggested that the context of antibody ligation in different cells was determinative of cytoxicity rather than just antibody binding.

EXAMPLE 6

Normal Human Tissue Staining

IHC studies were conducted to characterize 11BD-2E11-2 antigen distribution in humans. IHC optimization studies were performed previously in order to determine the conditions for further experiments. 11BD-2E11-2 monoclonal antibody was produced and purified as stated above.

As disclosed in Ser. No. 10/810,744, binding of antibodies to 20 normal human tissues was performed using a frozen human normal organ tissue array (Clinomics, Watervliet, N.Y.). Slides were postfixed for 10 min in cold (−20° C.)

acetone and then allowed to come to room temperature. Slides were rinsed in 4° C. cold phosphate buffered saline (PBS) 3 times for 2 min each followed by blocking endogenous peroxidase activity with washing in 3 percent hydrogen peroxide for 10 min. Slides were then rinsed in PBS 3 times for 5 min followed by incubation in Universal blocking solution (Dako, Toronto, Ontario) for 5 min at room temperature. 11BD-2E11-2, anti-human muscle actin (Clone HHF35, Dako, Toronto, Ontario) or isotype control antibody (directed towards *Aspergillus niger* glucose oxidase, an enzyme which is neither present nor inducible in mammalian tissues; Dako, Toronto, Ontario) were diluted in antibody dilution buffer (Dako, Toronto, Ontario) to its working concentration (5 µg/mL for each antibody except for anti-actin which was 2 µg/mL) and incubated overnight for 1 hr at room temperature. The slides were washed with PBS 3 times for 2 minutes each. Immunoreactivity of the primary antibodies was detected/visualized with HRP conjugated secondary antibodies as supplied (Dako Envision System, Toronto, Ontario) for 30 min at room temperature. Following this step the slides were washed with PBS 3 times for 2 min each and a color reaction developed by adding DAB (3,3'-diaminobenzidine tetrahydrachloride, Dako, Toronto, Ontario) chromogen substrate solution for immunoperoxidase staining for 10 min at room temperature. Washing the slides in tap water terminated the chromogenic reaction. Following counterstaining with Meyer's Hematoxylin (Sigma Diagnostics, Oakville, ON), the slides were dehyrdated with graded ethanols (95-100%) and cleared with xylene. Using mounting media (Dako Faramount, Toronto, Ontario) the slides were coverslipped. Slides were microscopically examined using an Axiovert 200 (Zeiss Canada, Toronto, ON) and digital images acquired and stored using Northern Eclipse Imaging Software (Mississauga, ON). Results were read, scored and interpreted by a pathologist.

Figure 7:
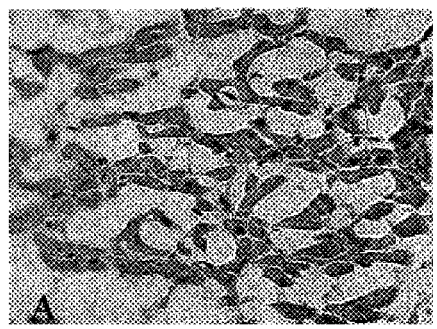
FIG. 7. Representative micrographs showing the binding pattern obtained with 11BD-2E11-2 (A) and the isotype control antibody (B) on tissues sections of heart from a frozen normal human tissue array. There is no staining of 11BD-2E11-2 to cardiac muscle fibers. Magnification is 200×.
Figure 7:
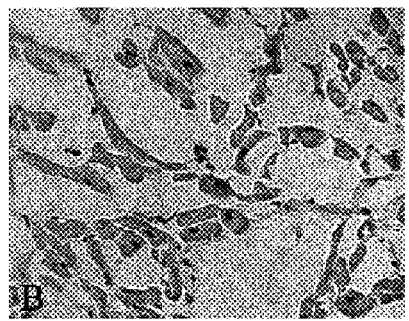
Figure 8:
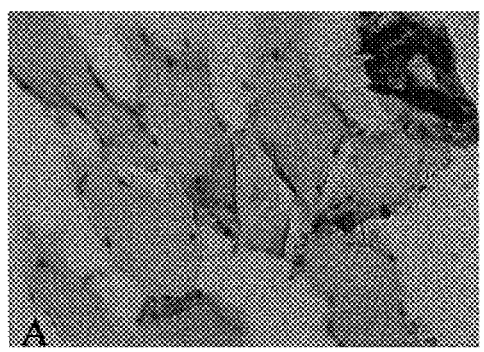
FIG. 8. Representative micrographs showing the binding pattern obtained with 11BD-2E11-2 (A), anti-actin (B) and the isotype control antibody (C) on tissues sections of skeletal muscle from a frozen normal human tissue array. 11BD-2E11-2 did not stain skeletal muscle but there is staining to the smooth muscles of blood vessels (arrow). Magnification is 200×.
Figure 8:
Figure 8:
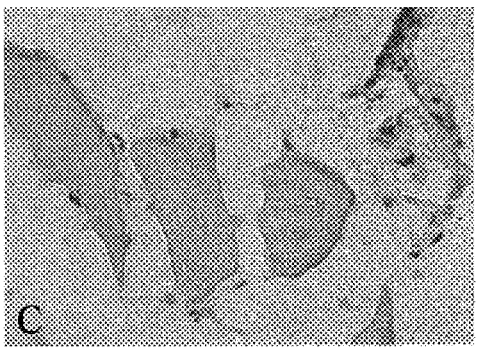

Table 6 presents a summary of the results of 11BD-2E11-2 staining of an array of normal human tissues. From the table, there were 2 main categories of tissue staining. A group of tissues was completely negative. These tissues included normal thyroid, bronchus and cardiac muscle of the left ventricle (FIG. 7). The second group of tissues included tissues in which staining was positive in the tissue section, but was limited to smooth muscle fibers of blood vessels and/or the epithelium (FIG. 8). These results suggested that the antigen for 11BD-2E11-2 was not widely expressed on normal tissues, and that the antibody would bind only to a limited number of tissues in humans. The normal human tissue staining of 11BD-2E11-2 resembles that previously reported for an anti-MCSP antibody; B5. B5 was previously shown to bind to skin keratinocytes, lung alveolar epithelium and capillary endothelium.

TABLE 6

11BD-2E11-2 IHC on Frozen Human Normal Tissue

| | Data sheet | | | IHC Score | | |
|---|---|---|---|---|---|---|
| S. No. | Tissues | Age | Sex | 11BD-2E11-2 | Actin | IgG negative control |
| 1 | Bronchus | 61 | M | – (PD) | +++ SMF & Myoepithelium of mucus acini | CD |
| 2 | Diaphragm | 61 | M | +++ SMF of blood vessels +/– Skeletal muscle fibers | +++ Skeletal muscle fibers & SMF of blood vessels | — |
| 3 | Pectoral muscle (Skeletal muscle) | 61 | M | +++ SMF of blood vessels | +++ Skeletal muscle fibers & SMF of blood vessels | — |
| 4 | Lung | 61 | M | +++ Alveolar epithelium & SMF of blood vessels | CD | – (F) |
| 5 | Aorta | 61 | M | ++ SMF (F) | CD | — |
| 6 | Left ventricle (Cardiac muscle) | 61 | M | — | +++ SMF of blood vessels + Cardiac muscle fibers | — |
| 7 | Esophagus | 61 | M | +++ SMF (PD) | CD | – (F) |
| 8 | Trachea | 61 | M | – (PD) | +++ SMF & myoepithelium of mucus acini | — |
| 9 | Kidney | 61 | M | +++ SMF of blood vessels | +++ SMF of blood vessels | — |
| 10 | Adrenal | 61 | M | +++ SMF of blood vessels | +++ SMF of blood vessels | — |
| 11 | Pancreas | 61 | M | +++ SMF of blood vessels + Acinar epithelium | +++ SMF of blood vessels | — |
| 12 | Spleen | 61 | M | +++ SMF of blood vessels & Polymorphs (F) | +++ SMF of blood vessels, reticular fibers & polymorphs (F) | Bg (polymorphs) |
| 13 | Liver | 61 | M | +++ SMF of blood vessels | – (PD) | — |
| 14 | Skin | 61 | M | +++ SMF of blood vessels +/– Keratinocytes | +++ SMF of blood vessels | Bg (Stroma) |
| 15 | Colon | 61 | M | +++ SMF of blood vessels | +++ SMF | — |
| 16 | Thyroid | 61 | M | – (PD) | – (PD) | — |
| 17 | Prostate | 61 | M | ++ SMF of blood vessels +/– Glandular epithelium | CD | CD |
| 18 | Testicle | 61 | M | ++ SMF of blood vessels | +++ stromal cells | — |
| 19 | Breast | 61 | M | +/– Ductal epithelium +++ SMF of blood vessels | +++ SMF of blood vessels | — |
| 20 | Ovary | 80 | F | ++ SMF of blood vessels & Stroma | F | CD |

Abbreviations:
SMF: smooth muscle fiber,
Bg: background staining,
PD: partially detached,
F: folded,
CD: completely detached.

EXAMPLE 7

Human Breast Tumor Tissue Staining

An IHC study was undertaken to determine the cancer association of the 11BD-2E11-2 antigen with human breast pattern, from 11BD-2E11-2, showed that in patient samples, the antibody was highly specific for malignant cells thereby making it an attractive druggable target. The breast tumor tissue staining of 11BD-2E11-2 resembles that previously reported for the anti-MCSP antibody B5. B5 was previously shown to bind to 60 percent of breast carcinoma tumor tissue.

TABLE 7

11BD-2E11-2 IHC on Frozen Human Normal and Breast Tumor Tissue

| | Data Sheet | | | | IHC Score | | |
|---|---|---|---|---|---|---|---|
| S. NO. | Tissue | Age | Sex | Diagnosis | 11BD-2E11-2 | Actin | IgG negative control |
| 1 | Breast | 61 | F | Infiltrating Ductal Carcinoma | CD | CD | CD |
| 2 | Breast | 74 | F | Infiltrating Ductal Carcinoma | – (PD) | – Tumor +++ SMF of blood vessels | — |
| 3 | Breast | 60 | F | Infiltrating Ductal Carcinoma | CD | PD | CD |
| 4 | Breast | 69 | F | Infiltrating Ductal Carcinoma | NR | NR | — |
| 5 | Breast | 64 | F | Infiltrating Ductal Carcinoma | CD | — | CD |
| 6 | Breast | 65 | F | Medullary Carcinoma | +++ (Tumor cells) | — | — |
| 7 | Breast | 75 | F | Infiltrating Ductal Carcinoma | +++ (Tumor cells) | CD | — |
| 8 | Breast | 48 | F | Infiltrating Ductal Carcinoma | ++ (Tumor cells) | – Tumor ++ Stroma | — |
| 9 | Breast | 87 | F | Infiltrating Ductal Carcinoma | +/– (Tumor cells) | – Tumor +++– SMF of blood vessels | CD |
| 10 | Breast | 75 | F | Infiltrating Ductal Carcinoma | NR (+/– SMF of blood vessels) | CD | — |
| 11 | Breast | 76 | F | Infiltrating Ductal Carcinoma | — | – Tumor +++ SMF of blood vessels & stroma | — |
| 12 | Breast | 66 | F | Infiltrating Ductal Carcinoma | CD | CD | — |
| 13 | Breast | 58 | F | Infiltrating Ductal Carcinoma | +++ (Tumor cells) | CD | CD |
| 14 | Breast | 37 | F | Infiltrating Ductal Carcinoma | CD | – Tumor +++ Stroma | — |
| 15 | Breast | 70 | F | Infiltrating Ductal Carcinoma | — | – Tumor +++ Myoepithelium & SMF of blood vessels | CD |
| 16 | Breast | 48 | F | Normal | – (PD) | CD | CD |
| 17 | Breast | 60 | F | Normal | — | – (PD) | — |
| 18 | Breast | 30 | F | Normal | CD | – Tumor +++ Myoepithelium & SMF of blood vessels | — |
| 19 | Breast | 34 | F | Normal | CD | – Tumor ++ Myoepithelium (PD) | — |
| 20 | Breast | 43 | F | Normal | — | – Tumor + SMF of blood vessels | — |

Abbreviations:
SMF: smooth muscle fiber,
PD: partially detached,
F: folded,
CD: completely detached.

cancers (disclosed in Ser. No. 10/810,744). A comparison was made for actin (positive control), and an antibody directed towards *Aspergillus niger* glucose oxidase, an enzyme which is neither present nor inducible in mammalian tissues (negative control). A breast cancer tissue array derived from 15 breast cancer patients and 5 samples derived from non-neoplastic breast tissue in breast cancer patients were used (Clinomics, Watervliet, N.Y.). The following information was provided for each patient: age, sex, and diagnosis. The procedure for IHC from Example 6 was followed.

Figure 9:
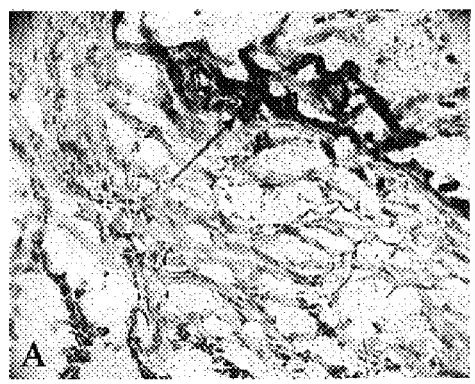
FIG. 9. Representative micrograph of 11BD-2E11-2 (A) and isotype control antibody (B) binding to breast cancer tumor (infiltrating duct carcinoma). The black arrow in panel A points to tumor cells. Magnification is 200×.
Figure 9:
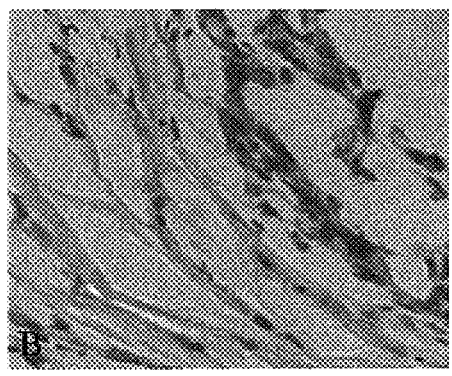

Table 7 provides a binding summary of 11BD-2E11-2 antibody staining of a breast cancer tissue array. Each array contained tumor samples from 15 individual patients. Overall, 62 percent of the 8 (7 of the tissue samples were either completely detached or not representative) patients tested were positive for the 11BD-2E11-2 antigen. Also for 11BD-2E11-2, 0 out of 3 (again 2 of the tissue samples were completely detached) normal breast tissue samples from breast cancer patients were positive (FIG. 9). For the 11BD-2E11-2 antigen there did not appear to be a trend to greater positive expression with higher tumor stage. However, this result was limited due to the small sample size. The 11BD-2E11-2 staining was specific for cancerous cells (FIG. 9). The staining

EXAMPLE 8

An IHC study was undertaken to determine the cancer association of the 11BD-2E11-2 antigen with human melanoma cancers. A comparison was made for an anti-CD63 antibody (NIK-C3; MEDICORP, Montreal QC); positive control), and an antibody directed towards *Aspergillus niger* glucose oxidase, an enzyme which is neither present nor inducible in mammalian tissues (negative control). A melanoma cancer tissue array derived from 35 melanoma cancer patients and 10 samples derived from normal skin tissue in melanoma cancer patients was used (TriStar Technology Group, LLC, Bethesda, Md.). The procedure for IHC from Example 6 was followed except for the following modifications. The color reaction developed by adding AEC (Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were cleared with distilled water.

Figure 10:
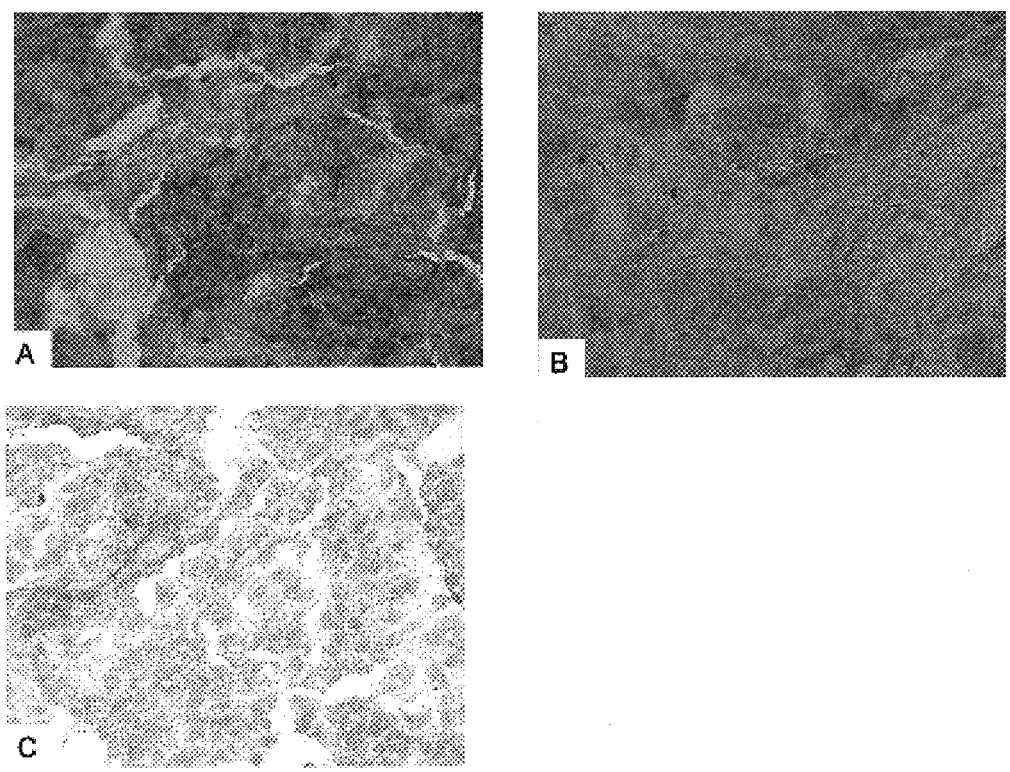
FIG. 10. Representative micrographs showing the binding pattern obtained with 11BD-2E11-2 (A), positive control anti-CD63 (NKI-C3) (B) and the negative isotype control antibody (C) on tissues sections of malignant melanoma from a frozen melanoma human tissue array. Magnification is 200×.
Figure 11:
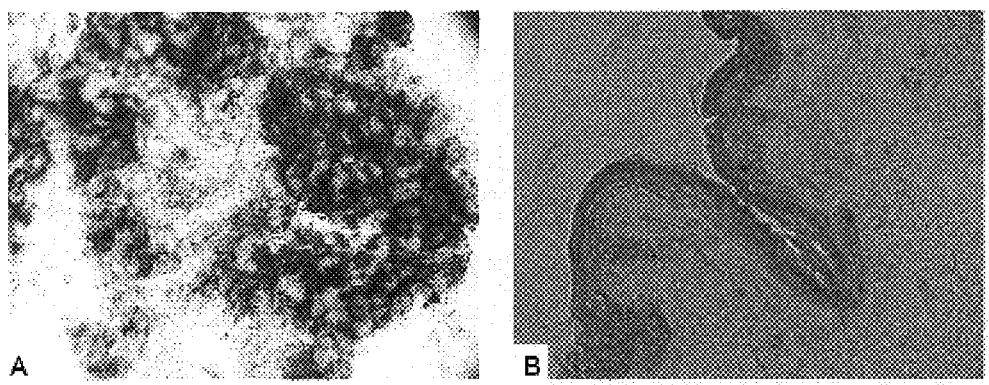
FIG. 11. Representative micrographs showing the binding pattern obtained with 11BD-2E11-2 on malignant melanoma (A) and normal skin (B) tissues sections from a frozen melanoma human tissue array. There is strong staining of 11BD-2E11-2 to the malignant melanoma but not to the normal skin. Magnification is 200×.

Table 8 provides a binding summary of 11BD-2E11-2 antibody staining of a melanoma cancer tissue array. Each array contained tumor samples from 35 individual patients and normal skin from 10 patients. Overall, 67 percent of the 33 (2 of the tissue samples were completely pigmented) patients tested were positive for the 11BD-2E11-2 antigen (FIG. 10). In addition, 0 out of 6 (4 of the tissue samples were non representative or not available) normal skin tissue samples from melanoma cancer patients were positive (FIG. 11). The 11BD-2E11-2 staining was specific for cancerous cells (FIG. 11). The staining pattern, from 11BD-2E11-2, showed that in patient samples, the antibody was highly specific for malignant cells thereby making it an attractive druggable target and demonstrating the utility of 11BD-2E11-2 as a potential drug.

TABLE 8

11BD-2E11-2 IHC on Frozen Human Normal Skin and Melanoma Tumor Tissue

| | | | IHC observations | | |
| --- | --- | --- | --- | --- | --- |
| Coordinates | Primary/meta | Organ | 11B-2E11-2 | NKI-C3 | IgG negative control |
| A1a | meta | lymph node | Completely Pigmented | Completely Pigmented | Completely Pigmented |
| A1b | meta | lymph node | — | + | — |
| A1c | meta | spleen | +++ | +++ | — |
| A1d | primary | skin | + | ++ | — |
| A1e | primary | esophagus | +/− | +++ | — |
| A1f | meta | lymph node | +++ | ++ | — |
| A1g | primary | skin | + | +++ | — |
| A1h | meta | lung | ++ | +++ | — |
| A1i | meta | lymph node | +/− | — | cd |
| A1k | meta | lymph node | ++ | ++ | — |
| A2a | primary | skin | Completely Pigmented | Completely Pigmented | Completely Pigmented |
| A2b | meta | skin | — | — | — |
| A2c | primary | skin | +++ | — | — |
| A2d | meta | soft tissue | +++ | ++ | — |
| A2e | meta | lymph node | +++ | +++ | — |
| A2f | meta | lymph node | +++ | +++ | cd |
| A2g | primary | skin | — | +++ | — |
| A2h | meta | lymph node | + | — | — |
| A2i | meta | lymph node | +++ | + | — |
| A2k | meta | soft tissue | — | — | cd |
| A3a | primary | skin | +++ | ++ | — |
| A3b | primary | skin | +++ | +++ | — |
| A3c | meta | lymph node | — | — | — |
| A3d | meta | lymph node | + | +/− | — |
| A3e | meta | lymph node | +/− | +++ | — |
| A3f | meta | lymph node | +/− | ++ | — |
| A3g | meta | lymph node | — | — | — |
| A3h | meta | lymph node | — | — | — |
| A3i | meta | lymph node | — | — | — |
| A3k | meta | lymph node | — | — | — |
| A4a | meta | lymph node | — | +/− | — |
| A4b | meta | lymph node | +++ | +++ | — |
| A4c | primary | skin | + | +++ | — |
| A4d | meta | soft tissue | +++ | +++ | — |
| A4e | meta | lymph node | — | ++ | — |
| A5a | normal | skin | — | — | — |
| A5b | normal | skin | — | — | — |
| A5c | normal | skin | NR | NR | NR |
| A5d | normal | skin | — | — | — |
| A5e | normal | skin | — | — | — |
| A5f | normal | skin | — | — | — |
| A5g | normal | skin | NA | NA | NA |
| A5h | normal | skin | — | — | — |
| A5i | normal | skin | NR | NR | NR |
| A5k | normal | skin | NR | NR | cd |

Abbreviations:
meta: metastatic,
NR: section is not representative,
cd: section is completely detached,
NA: section is not available.

EXAMPLE 9

In Vivo MDA-MB-468 Established Tumor Experiment

As disclosed in Ser. No. 10/810,744 and with reference to FIG. 12, 6 to 8 week old female SCID mice were implanted with 2 million MDA-MB-468 human breast cancer cells in 100 microlitres saline injected subcutaneously in the scruff of the neck. Tumor growth was measured with calipers every week. When the majority of the cohort reached a tumor volume of 100 mm$^3$, 5-6 mice were randomized into each of 2 treatment groups. 11BD-2E11-2 or buffer control was administered intraperitoneally with 10 mg/kg/dose at a volume of 300 microliters after dilution from the stock concentration with a diluent that contained 2.7 mM KCl, 1 mM KH$_2$PO$_4$, 137 mM NaCl and 20 mM Na$_2$HPO$_4$. The antibodies were then administered 3 times per week for a total of 10 doses in the same fashion until day 66 post-implantation. Tumor growth was measured about every seventh day with calipers for the duration of the study or until individual animals reached CCAC end-points. Body weights of the animals were recorded for the duration of the study. At the end of the study all animals were euthanised according to CCAC guidelines.

Figure 12:
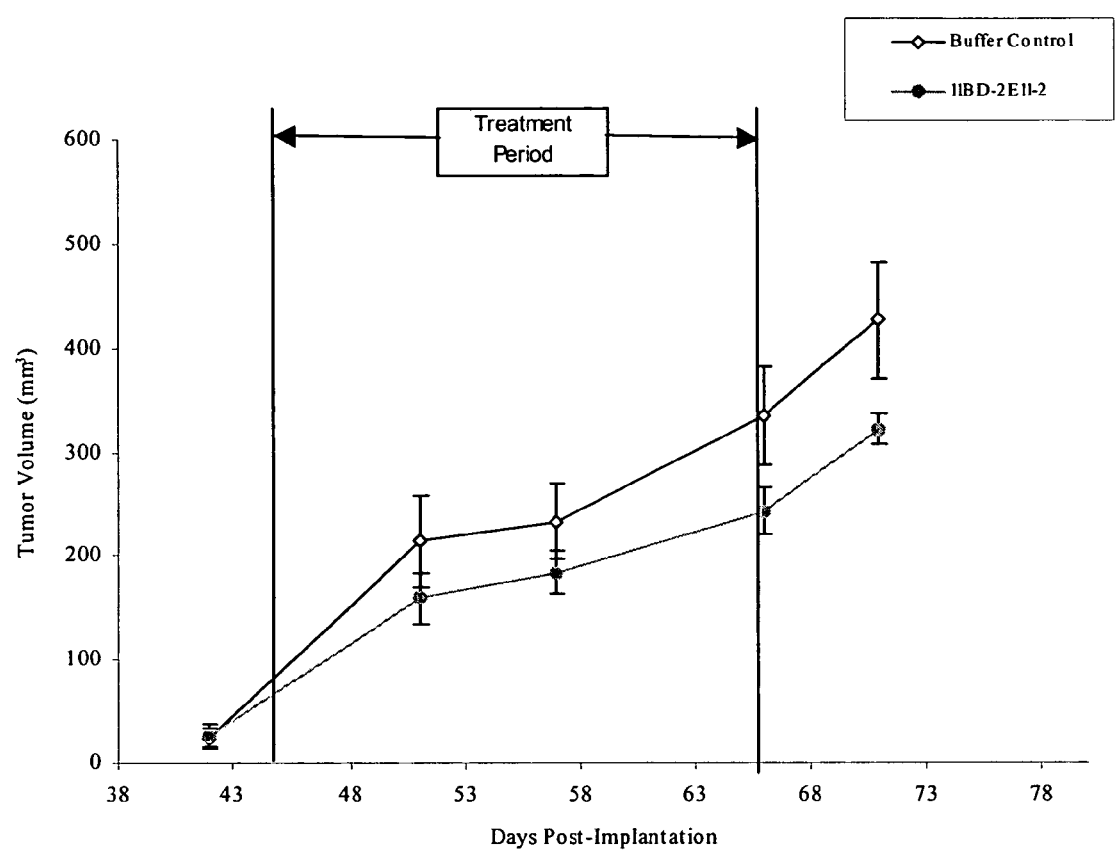
FIG. 12. Effect of 11BD-2E11-2 or buffer control on tumor growth in a preventative MDA-MB-468 breast cancer model. The dashed line indicates the period during which the antibody was administered. Data points represent the mean+/−SEM.

At the time of randomization the mean tumor volumes and the standard deviations in each group were similar. Statistically there was no difference in body weight between the groups. This indicated that true randomization had occurred. As shown in FIG. 12, the antibody 11BD-2E11-2 suppressed tumor growth by 25 percent in comparison to buffer control at the end of the 3-week treatment period (p=0.52). Although this was not a significant difference, a trend towards reduced tumor volume in comparison to the buffer control was observed throughout the study. Therefore, 11BD-2E11-2 has shown efficacy in an established breast cancer model.

EXAMPLE 10

In Vivo ES-2+SEAP Established Tumor Experiment

As disclosed in Ser. No. 10/810,744 and with reference to FIGS. 13 and 14, 6 to 8 week old female athymic nude mice were intraperitoneally implanted with 10 million ES-2+SEAP human ovarian cancer cells stably transfected to express human placental secreted alkaline phosphatase (SEAP). The 10 million ovarian cancer cells were resuspended in 500 microlitres serum-free α-MEM. Tumor growth was confirmed with the sacrifice of 3 mice on day 7. Following the confirmation of tumor growth on day 7, 8 mice were randomized into each of 2 treatment groups. 11BD-2E11-2 or buffer control was administered intraperitoneally with 10 mg/kg/dose at a volume of 250 microliters after dilution from the stock concentration with a diluent that contained 2.7 mM KCl, 1 mM KH$_2$PO$_4$, 137 mM NaCl and 20 mM Na$_2$HPO$_4$. The antibodies were then administered once per day for 5 doses and then once every other day for another 5 doses for a total of 10 doses. Tumor burden was extrapolated by measuring circulating SEAP levels and assessed visually upon necropsy for the duration of the study or until individual animals reached CCAC end-points. Body weights of the animals were recorded for the duration of the study. At the end of the study all animals were euthanised according to CCAC guidelines.

Figure 13:
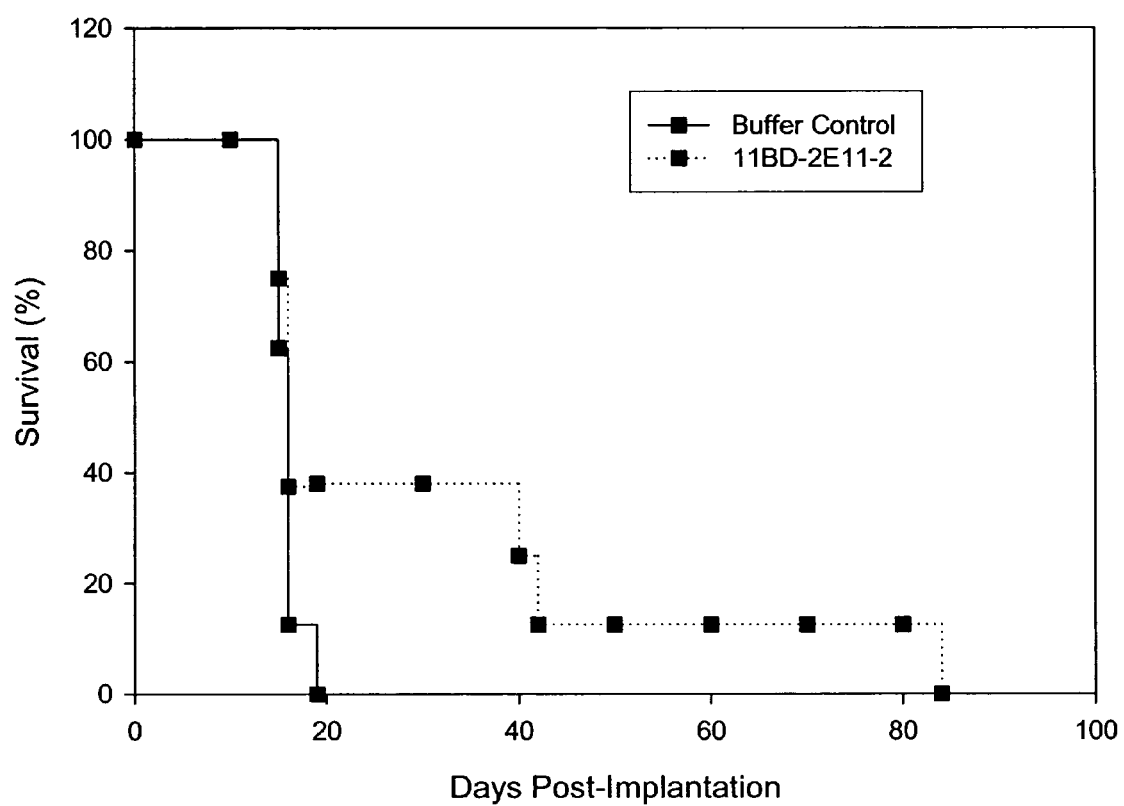
FIG. 13. Survival of tumor-bearing mice after treatment with 11BD-2E11-2 or buffer control antibody in an established ES-2 xenograft study.
Figure 14:
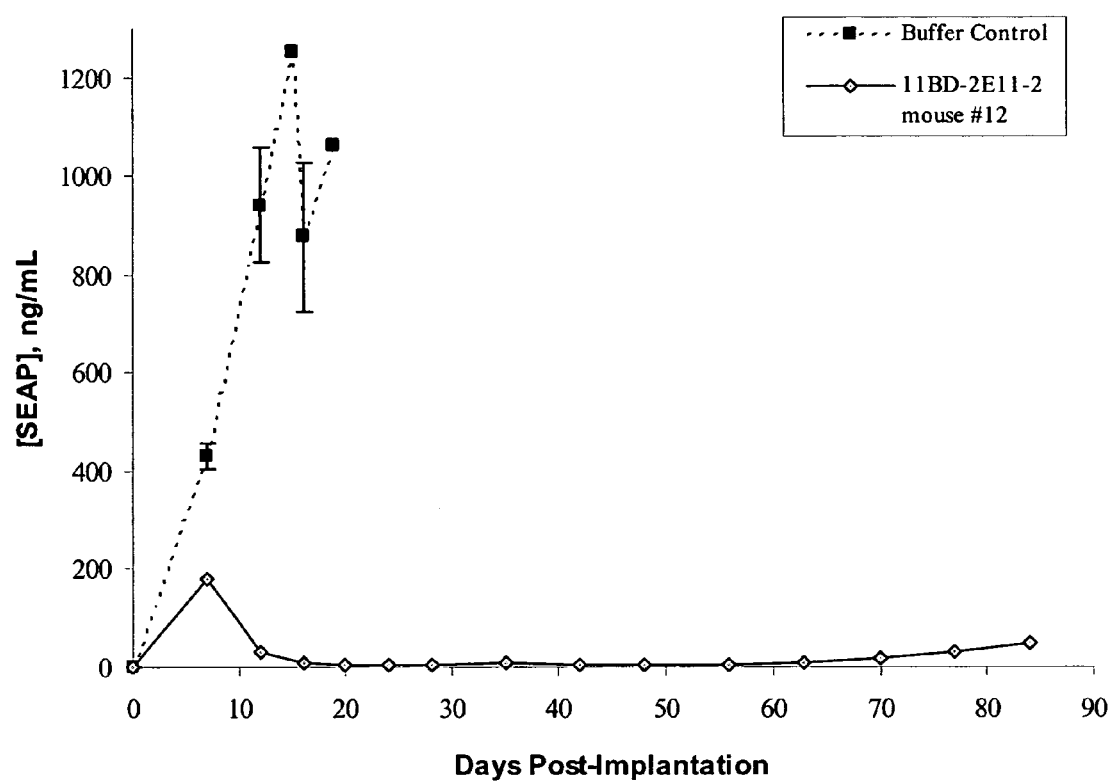
FIG. 14. SEAP levels of tumor-bearing mice before, during and after treatment with 11BD-2E11-2 or buffer control in an established ES-2 xenograft study.

At the time of randomization circulating plasma SEAP levels (indicative of tumor burden) were analyzed. There was not a significant difference in the average SEAP level between the 11BD-2E11-2 and buffer control treatment group. However, within groups there was variable tumor take-rate. As shown in FIG. 13, the antibody 11BD-2E11-2 displayed a trend for improved survival in a cohort of the treatment group. As illustrated in FIG. 14, one animal receiving 11BD-2E11-2 treatment had a decreased amount of circulating SEAP to nearly negligible levels. The low level of circulating SEAP continued on until approximately 60 days post-implantation.

EXAMPLE 11

In Vivo A2058 Human Melanoma Preventative Tumor Experiment

With reference to the data shown in FIG. 15, 4 to 8 week old, female SCID mice were implanted with 0.75 million A2058 human melanoma cancer cells in 100 microliters saline injected subcutaneously in the scruff of the neck. The mice were randomly divided into 2 treatment groups of 5. On the day after implantation 20 mg/kg of 11BD-2E11-2 test antibody or buffer control was administered intraperitoneally at a volume of 300 microliters after dilution from the stock concentration with a diluent that contained 2.7 mM KCl, 1 mM KH$_2$PO$_4$, 137 mM NaCl and 20 mM Na$_2$HPO$_4$. The antibody or buffer control was then administered once per week for a period of 7 weeks in the same fashion.

Tumor growth was measured about every 7th day with calipers for up to 10 weeks or until individual animals reached the Canadian Council for Animal Care (CCAC) end-points. Body weights of the animals were recorded for the duration of the study. At the end of the study all animals were euthanised according to CCAC guidelines.

Figure 15:
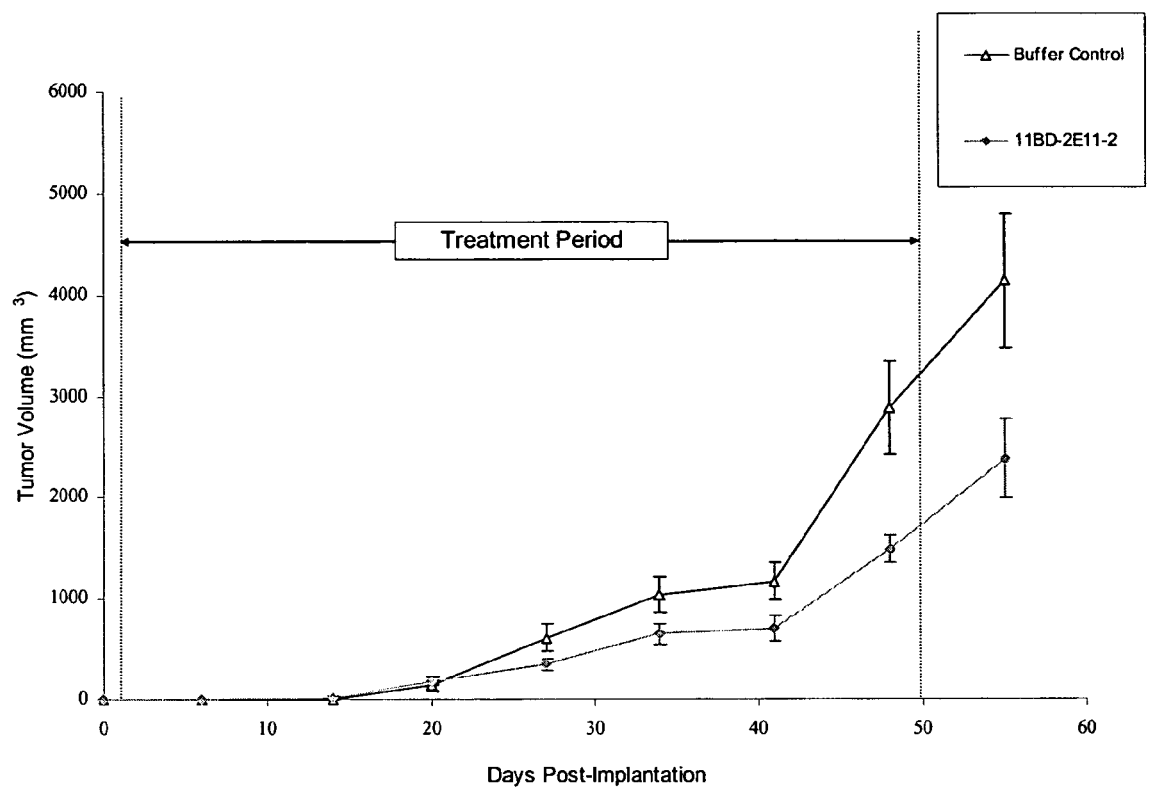
FIG. 15. Effect of 11BD-2E11-2 or buffer control on tumor growth in a preventative A2058 melanoma cancer model. The dashed line indicates the period during which the antibody was administered. Data points represent the mean+/−SEM.
Figure 16:
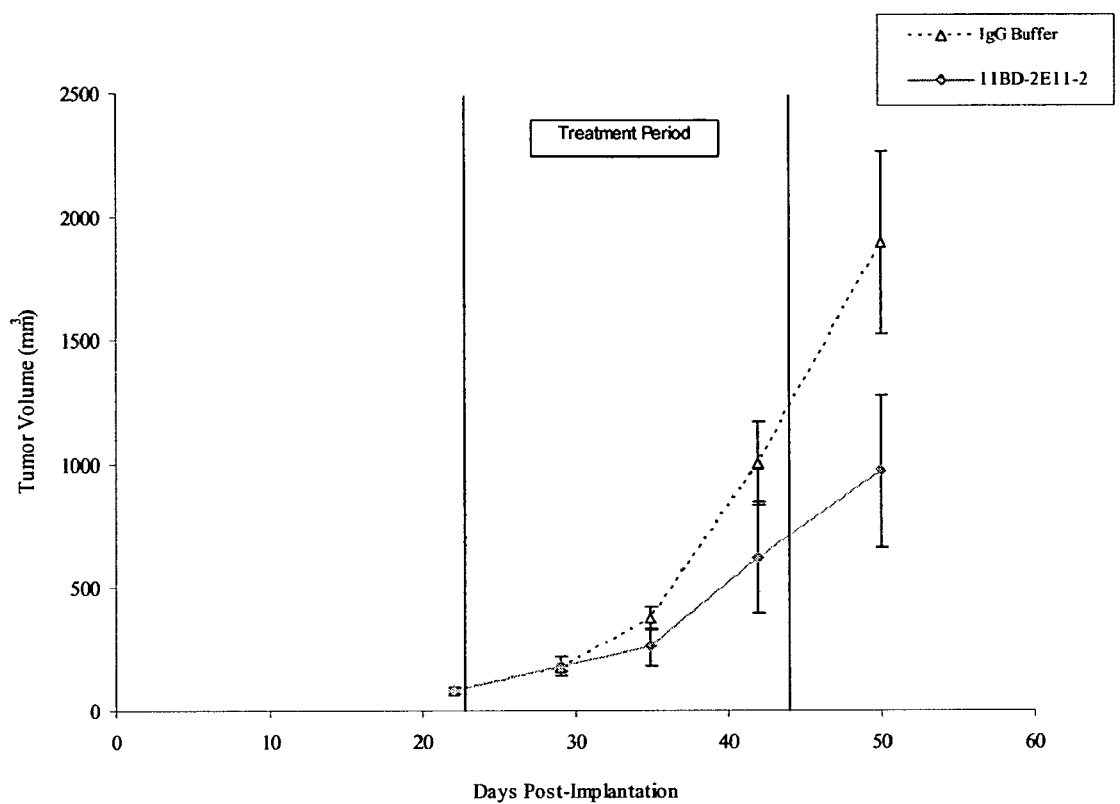
FIG. 16. Effect of 11BD-2E11-2 or buffer control on tumor growth in an established A2058 melanoma cancer model. The dashed line indicates the period during which the antibody was administered. Data points represent the mean+/−SEM.

As shown in FIG. 15, 11BD-2E11-2 treatment resulted in decreased tumor growth compared to treatment with the buffer control. On day 55 (5 days after the end of treatment), the mean tumor volume in the 11BD-2E11-2 treated group was 58 percent of the buffer control (p=0.046, unpaired t-test). Therefore, 11BD-2E11-2 displayed efficacy in the treatment of breast, ovarian and melanoma in vivo models of human cancer and reduced tumor burdens in comparison to controls in those same cancers.

EXAMPLE 12

In Vivo A2058 Human Melanoma Established Tumor Experiment

With reference to FIG. 16, 6 to 8 week old female SCID mice were implanted with 0.5 million A2058 human melanoma cancer cells in 100 microlitres saline injected subcutaneously in the scruff of the neck. Tumor growth was measured with calipers every week. When the majority of the cohort reached a tumor volume of 100 mm$^3$, 5 mice were randomized into each of 2 treatment groups. 11BD-2E11-2 or buffer control was administered intraperitoneally with 20 mg/kg/dose at a volume of 300 microliters after dilution from the stock concentration with a diluent that contained 2.7 mM KCl, 1 mM KH$_2$PO$_4$, 137 mM NaCl and 20 mM Na$_2$HPO$_4$. The antibodies were then administered 3 times per week for a total of 10 doses in the same fashion until day 44 post-implantation. Tumor growth was measured about every seventh day with calipers for the duration of the study or until individual animals reached CCAC end-points. Body weights of the animals were recorded for the duration of the study. At the end of the study all animals were euthanised according to CCAC guidelines.

At the time of randomization the mean tumor volumes and the standard deviations in each group were similar. Statistically there was no difference in body weight between the groups. This indicated that true randomization had occurred.

As shown in FIG. 13, the antibody 11BD-2E11-2 suppressed tumor growth by 49 percent in comparison to buffer control after the treatment period (p=0.1272; unpaired t-test). Although this was not a significant difference, a trend towards reduced tumor volume in comparison to the buffer control was observed throughout the study. Therefore, 11BD-2E11-2 has shown efficacy in both an established breast, ovarian and melanoma cancer model. In all, these results in which 11BD-2E11-2 produced benefits (improved survival and/or decreased tumor burden in comparison to control treatment) in mulitple models of human cancer suggest pharmacologic and pharmaceutical benefits of this antibody for cancer therapy in mammals, including man.

The preponderance of evidence shows that 11BD-2E112 mediates anticancer effects through ligation of an epitope present on MCSP. For the purpose of this invention, said epitope is defined as a "MCSP antigenic moiety" characterized by its ability to bind with a monoclonal antibody encoded by the hybridoma cell line 11BD-2E11-2, antigenic binding fragments thereof or antibody conjugates thereof. It has been shown, in Example 3, 11BD-2E11-2 antibody can be used to immunoprecipitate the cognate antigen from expressing cells such as MDA-MB-231 cells. Further it could be shown that the 11BD-2E112 antibody could be used in detection of cells and/or tissues which express a MCSP antigenic moiety which specifically binds thereto, utilizing techniques illustrated by, but not limited to FACS, cell ELISA or IHC.

Thus, it could be shown that the immunoprecipitated 11BD2E11-2 antigen can inhibit the binding of 11BD-2E11-2 to such cells or tissues using FACS, cell ELISA or IHC assays. Further, as with the 11BD-2E11-2 antibody, other anti-MCSP antibodies could be used to immunoprecipitate and isolate other forms of the MCSP antigen, and the antigen can also be used to inhibit the binding of those antibodies to the cells or tissues that express the antigen using the same types of assays.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A binding essay to determine a presence of cells which express the melanoma-associated chondroitin sulfate proteoglycan epitope which specifically binds to the isolated monoclonal antibody produced from the hybridome deposited with the ATCC as PTA-5643, or an antigen binding fragment thereof comprising:
   providing a cell sample;
   providing an isolated monoclonal antibody of antigen binding fragment thereof which binds to the same melanoma-associated chondroitin sulfate proteoglycan epitope as the monoclonal antibody produced from said hybridoma;
   contacting said isolated monoclonal antibody of antigen binding fragment thereof with said cell sample; and
   determining binding of said isolated monoclonal antibody or antigen binding fragment thereof with said cell sample;
   whereby the presence of cells which express said melanoma-associated chondroitin sulfate proteoglycan epitope is determined.

2. The binding assay of claim 1, wherein the cell sample is obtained from a tumor originating in a tissue selected from the group consisting of breast, and melanoma tissue.

3. A process of isolating or screening for cells in a sample which express the melanoma-associated chondroitin sulfate proteoglycan epitope which specifically binds to the isolated monoclonal antibody or antigen binding fragment thereof produced from the hybridoma deposited with the ATCC as PTA-5643 comprising:
   providing a cell sample;
   providing an isolated monoclonal antibody or antigen binding fragment thereof which binds to the same melanoma-associated chondroitin sulfate proteoglycan epitope as the monoclonal antibody produced from said hybridoma;
   contacting said isolated monoclonal antibody or antigen binding fragment thereof with said cell sample; and
   determining binding of said isolated monoclonal antibody of antigen binding fragment thereof with said cell sample;
   whereby said cells which express said melanoma-associated chondroitin sulfate proteoglycan epitope are isolated by said binding and their presence in said cell sample is confirmed.

4. The process of claim 3 wherein the cell sample is obtained from a tumor originating in a tissue selected from the group consisting of breast, and melanoma tissue.

* * * * *